(12) United States Patent
Seedhom et al.

(10) Patent No.: US 12,310,840 B2
(45) Date of Patent: May 27, 2025

(54) IMPLANT ASSEMBLY AND ASSOCIATED METHODS OF MANUFACTURING

(71) Applicant: Xiros Limited, Leeds (GB)

(72) Inventors: Bahaa Botros Seedhom, Leeds (GB); Corey James Robinson, Leeds (GB); Michal Piotrowski, Leeds (GB)

(73) Assignee: Xiros Limited, Leeds (GB)

( * ) Notice: Subject to any disclaimer, the term of this patent is extended or adjusted under 35 U.S.C. 154(b) by 900 days.

(21) Appl. No.: 17/298,519

(22) PCT Filed: Nov. 29, 2019

(86) PCT No.: PCT/GB2019/053385
§ 371 (c)(1),
(2) Date: May 28, 2021

(87) PCT Pub. No.: WO2020/109817
PCT Pub. Date: Jun. 4, 2020

(65) Prior Publication Data
US 2022/0047377 A1 Feb. 17, 2022

(30) Foreign Application Priority Data
Nov. 29, 2018 (GB) .................................... 1819426

(51) Int. Cl.
*A61F 2/08* (2006.01)
*A61B 17/04* (2006.01)

(52) U.S. Cl.
CPC ..... *A61F 2/0811* (2013.01); *A61F 2002/0852* (2013.01); *A61F 2002/0858* (2013.01);
(Continued)

(58) Field of Classification Search
CPC ................................................ A61F 2002/0882
See application file for complete search history.

(56) References Cited

U.S. PATENT DOCUMENTS 5,306,301 A * 4/1994 Graf ...................... A61F 2/0805
623/13.12
5,921,986 A * 7/1999 Bonutti ................ A61B 17/683
606/57
(Continued)

FOREIGN PATENT DOCUMENTS

EP 2581047 A1 4/2013
EP 2883518 A1 6/2015
(Continued)

OTHER PUBLICATIONS

Search Report from the United Kingdom Intellectual Property Office for corresponding Great Britain Application No. GB1819426.6, May 10, 2019, 4 pages.
(Continued)

*Primary Examiner* — Ann Hu
(74) *Attorney, Agent, or Firm* — Klarquist Sparkman, LLP

(57) ABSTRACT

An implant assembly for use in tissue repair having an adjustable length and comprising: a fixation device comprising a bone facing surface, an outer surface, a first and at least one further aperture extending through the fixation device from the outer surface to the bone facing surface; and a flexible elongate element secured to the fixation device and having first and second free ends.

46 Claims, 41 Drawing Sheets

(52) U.S. Cl.
CPC ................ *A61F 2002/0882* (2013.01); *A61F 2250/0007* (2013.01)

(56) References Cited

U.S. PATENT DOCUMENTS

| | | | |
|---|---|---|---|
| 6,972,027 B2* | 12/2005 | Fallin ................. | A61B 17/0401 606/232 |
| 8,628,573 B2 | 1/2014 | Roller et al. | |
| 9,149,267 B2* | 10/2015 | Norton ............... | A61B 17/0401 |
| 9,192,372 B2* | 11/2015 | Bentley .............. | A61B 17/0482 |
| 9,351,720 B2* | 5/2016 | Seedhom ............ | A61B 17/0401 |
| 9,561,027 B2* | 2/2017 | Perriello ............ | A61B 17/0401 |
| 9,757,113 B2 | 9/2017 | Pasquali et al. | |
| 9,801,625 B2* | 10/2017 | Dooney, Jr. ............. | A61B 17/80 |
| 10,631,845 B2* | 4/2020 | Burkhart ............. | A61B 17/0401 |
| 11,272,920 B2* | 3/2022 | Gustafson ........ | A61B 17/06166 |
| 11,497,484 B2* | 11/2022 | Lund ...................... | A61L 31/048 |
| 11,642,120 B2* | 5/2023 | Burkhart ............... | A61F 2/0811 606/232 |
| 11,684,468 B2* | 6/2023 | Hernandez ................ | A61F 2/08 606/232 |
| 11,723,645 B2* | 8/2023 | Bachmaier ......... | A61B 17/0401 606/232 |
| 2002/0173788 A1* | 11/2002 | Bojarski ............ | A61B 17/0401 606/60 |
| 2009/0182335 A1* | 7/2009 | Struhl ................... | A61F 2/0811 606/228 |
| 2010/0125297 A1* | 5/2010 | Guederian ......... | A61B 17/0401 606/232 |
| 2010/0256677 A1* | 10/2010 | Albertorio ............ | A61F 2/0811 606/232 |
| 2012/0065732 A1 | 3/2012 | Roller et al. | |
| 2012/0310279 A1 | 12/2012 | Sikora et al. | |
| 2013/0197580 A1 | 8/2013 | Perriello et al. | |
| 2014/0257346 A1 | 9/2014 | Sengun et al. | |
| 2015/0196385 A1 | 7/2015 | Kam et al. | |
| 2016/0157851 A1* | 6/2016 | Spenciner ............. | A61F 2/0811 606/232 |
| 2017/0049434 A1 | 2/2017 | Dooney, Jr. et al. | |
| 2018/0140416 A1* | 5/2018 | Prandi ................ | A61B 17/0401 |
| 2018/0256155 A1 | 9/2018 | Burkhart et al. | |
| 2020/0015804 A1* | 1/2020 | Bachmaier ............ | A61F 2/0811 |

FOREIGN PATENT DOCUMENTS

| | | |
|---|---|---|
| KR | 1020160087580 | 7/2016 |
| WO | WO2018/169961 A1 | 9/2018 |

OTHER PUBLICATIONS

Invitation to Pay Additional Fees and, Where Applicable, Protest Fee (Communication Relating to the Results of the Partial International Search) of the International Preliminary Examining Authority, Form PCT/ISA/206 (including Annex), mailed Feb. 27, 2020, for corresponding International Application No. PCT/GB2019/053385, 16 pages.

International Search Report and Written Opinion of the International Searching Authority, mailed Mar. 25, 2020, for corresponding International Application No. PCT/GB2019/053385, 30 pages.

Written Opinion of the International Preliminary Examining Authority, mailed Nov. 19, 2020, for corresponding International Application No. PCT/GB2019/053385, 15 pages.

Written Opinion of the International Preliminary Examining Authority, mailed Mar. 11, 2021, for corresponding International Application No. PCT/GB2019/053385, 6 pages.

International Preliminary Report on Patentability of the International Searching Authority, mailed Jun. 1, 2021, for corresponding International Application No. PCT/GB2019/053385, 34 pages.

* cited by examiner

IMPLANT ASSEMBLY AND ASSOCIATED METHODS OF MANUFACTURING

CROSS REFERENCE TO RELATED APPLICATIONS

This is the U.S. National Stage of International Application No. PCT/GB2019/053385, filed Nov. 29, 2019, which in turn claims the benefit of and priority to Great Britain Patent Application No. 1819426.6, filed Nov. 29, 2018.

The present invention relates to an implant assembly for use in tissue repair, the implant assembly having an adjustable length. In particular, but not exclusively, the present invention relates to an implant assembly for use in tissue repair comprising a fixation device and a flexible elongate element secured to the fixation device, at least part of the elongate element being for location within a bone tunnel. The present invention also relates to a method of manufacturing such an implant assembly, and a method of carrying out tissue repair involving the use of such an implant assembly. The present invention further relates to an implant construction device for forming such an implant assembly, and associated methods.

Ligament damage, including anterior cruciate ligament (ACL) ruptures, are common in many sports. In the past, one way in which reconstruction of an ACL was carried out was by harvesting two hamstring tendons from a patient, and implanting the tendons in a position where they perform the function of the damaged ACL. More recently, synthetic implants have been used in the reconstruction of damaged ligaments.

A variety of techniques have been employed by surgeons to anchor the hamstring tendons (or synthetic implant) to the knee bones. The most common technique involves the use of a fixation assembly comprising a fixation device which is used to suspend the hamstring tendon/synthetic implant from the bone, most often from the femur bone. The fixation devices employed in such prior synthetic fixation assemblies often take the form of an elongate button, which comprises a pair of apertures through which a continuous loop is passed, the loop serving for suspending the implant in the bone tunnel. One such prior assembly is disclosed in the International Patent Publication no. WO-98/12992 of Neoligaments Limited. The assembly disclosed in this document comprises a fixation device which is drawn along a bone tunnel trailing an implant, the implant being coupled to the fixation device via a continuous loop. On emerging from an opening of the bone tunnel, the fixation device is flipped so that it overlies the tunnel mouth, so that it contacts the outer surface of the bone surrounding the mouth. The implant can then be tensioned, and secured within the tunnel by inserting a fixation component into the bone at the opposite end of the tunnel. Many different fixation devices have been employed, including interference screws that are inserted into the opposite tunnel mouth so as to clamp the implant against an internal wall of the tunnel, and staples which are inserted into the outer surface of the bone adjacent the opposite tunnel mouth so as to clamp the implant against the bone surface.

It has been recognised that it would be advantageous if the loop which is secured to the fixation device could be adjustable, so that a length of the loop can be varied. This would enable a distance between the fixation device and the implant suspended from the device to be adjusted. Such would provide numerous benefits, including an ability to adjust the device during a surgical procedure in which the implant is secured in the bone tunnel, for example to account for anatomical differences from patient-to-patient, and deviations from a surgical plan which might involve the bone tunnel opening in a different location on the bone surface than had originally been intended.

The issues discussed above are not restricted to ACL (or other ligament/tendon repair). Other surgical techniques involve the location of an implant in a tunnel in a bone, including but not restricted to in syndesmotic joint repair, such as to the distal tibiofibular syndesmosis between the distal tibia and the fibula in a human leg. The distal tibia and fibula bones in the joint are connected by the interosseous ligament (IOL), the anterior-inferior tibiofibular ligament (AITFL), the posterior-inferior tibiofibular ligament (PITFL) and the transverse tibiofibular ligament (TTFL). Distraction of the bones in a syndesmotic joint can cause damage to the connective tissue (ligaments) in the joint, causing significant loss of mobility and pain. In the case of the distal tibiofibular syndesmosis, distraction of the fibula relative to the distal tibia can cause damage to the ligaments of the joint, resulting in a permanent dislocation of the fibula from the distal tibia. Such injuries are common in high energy sports such as skiing, rugby and American football. In this case, the ability to adjust a length of the loop would facilitate a procedure for repairing distracted joints, as it would again enable adjustment of the assembly to suit the patient in question.

A number of prior techniques of adjusting a length of a loop of an implant assembly of the type discussed above have been proposed, exemplified by U.S. Pat. No. 8,460, 379, 9,700,403, 9,757,113 and 8,936,621, and US Patent Publication Nos. US-2015/0112385 and US-2017/0231752. There is a desire to improve upon the techniques and assemblies disclosed in these documents.

According to a first aspect of the present invention, there is provided an implant assembly for use in tissue repair, the implant assembly having an adjustable length and comprising:

a fixation device comprising a bone facing surface, an outer surface opposite the bone facing surface, a first aperture extending through the fixation device from the outer surface to the bone facing surface, and at least a second aperture extending through the fixation device from the outer surface to the bone facing surface;

a flexible elongate element secured to the fixation device, the flexible elongate element having a first free end and a second free end, in which the flexible elongate element passes through apertures of the fixation device so that:

at least two bone-side loops are formed which each extend from at least one of the apertures at the bone facing surface of the fixation device, at least one of the bone-side loops forming a support loop adapted to be located at least partly within a bone tunnel;

at least one fixation loop is formed which extends from one of the apertures at the outer surface of the fixation device to another one of the apertures at the outer surface of the fixation device; and an adjustable knot arrangement is formed comprising an adjustable knot which is positionable on the outer surface of the fixation device, a first leg extending from the knot to the first free end of the elongate element and a second leg extending from the knot to the second free end of the elongate element;

in which the flexible elongate element is securable to the fixation device by the fixation loop, the fixation loop passing over at least part of the adjustable knot arrangement to clamp the knot arrangement to the fixation device when the bone-side loops are tensioned relative to the fixation device;

and in which a length of each of the bone-side loops is adjustable, and/or so as to allow a length of each of the bone-side loops to be adjusted.

The implant assembly of the present invention may provide the advantage that the lengths of the bone-side loops can easily be adjusted. This is facilitated by the arrangement of bone-side loops, fixation loop and adjustable knot, all of which are formed by the flexible elongate element. The ability to easily adjust the lengths of the bone-side loops provides greater flexibility during a surgical procedure, in comparison to prior techniques and assemblies.

The adjustable knot assembly may be an overhand knot assembly, comprising an overhand knot. Reference is made to an overhand knot, which should take its standard form and definition. As is well known, formation of an overhand knot may involve taking a portion of the flexible elongate element having the first free end and a portion of the flexible elongate element having the second free end, crossing one of said portions behind the other to form an eye, and then directing one of said portions around the other portion and through the eye to form a loop. In the context of the present invention, the loop that is formed may be bound by the outer surface of the fixation device.

The support loop may be adapted to support an implant within the bone tunnel. The support loop may form or define at least part of an implant. Each of the bone-side loops may form a support loop adapted to be located in the bone tunnel.

Advantageously, by appropriate cooperation with the fixation device, the bone-side loops, fixation loop and adjustable knot arrangement may be capable of being formed from a single element or component (the flexible elongate element), and in particular from a single length of the flexible elongate element.

Where the fixation device comprises a first aperture and a second aperture (for accommodating the flexible elongate element):

said bone-side loops may extend from one of the apertures at the bone facing surface of the fixation device to the other one of the apertures at the bone facing surface; and said fixation loop may extend from one of the apertures at the outer surface of the fixation device to the other one of the apertures at the outer surface of the fixation device.

The fixation device may comprise the first aperture, the second aperture, and at least one further aperture, for accommodating the flexible elongate element. The fixation device may comprise four apertures, and optionally more than four. At least one of the bone-side loops may extend from different apertures at the bone facing surface of the fixation device in comparison to at least one other bone-side loop. At least one bone-side loop may extend from a first aperture at the bone facing surface to a second aperture at the bone facing surface. At least one further bone side-loop may extend from a third aperture at the bone facing surface to a fourth aperture at the bone facing surface.

One or more of the bone-side loops that are formed may extend from one of the apertures at the bone facing surface of the fixation device to another one of the apertures at the bone facing surface.

One or more of the bone-side loops that are formed may extend from a same aperture at the bone facing surface of the fixation device. In other words, the flexible elongate element forming said loop may extend from an aperture of the fixation device on the bone-facing surface side of the fixation device, and may then follow a path which forms the bone-side loop before passing back through the fixation device to the outer surface side through the same aperture.

Reference is made to a bone-facing surface and an outer surface of the fixation device. Reference may also be made to a first and a second (opposite surface), and/or to inner surfaces and outer surfaces (which may be taken during use), respectively.

Reference is made to a number of different loops which are formed by the flexible elongate element. It will be understood that the loops that are formed may be defined by the flexible elongate element in conjunction with the fixation device (so that at least part of the loop is defined or bordered by the fixation device).

Some prior adjustable length implant assemblies comprise a flexible elongate element having a tubular braided construction, in which a part of the element is fed back on itself (into and along an internal cavity of the elongate element) to form a 'braid-in-braid' construction. Adjustment of such constructions can be challenging, as openings defined between transversely oriented fibres forming an outer part of the construction tend to elongate under tensile loading, reducing a diameter of the internal cavity so that the outer part clamps down on an inner part of the elongate element disposed in the cavity.

The flexible elongate element may be arranged so that it follows a path which extends continuously through the apertures in the fixation device to form the at least two bone-side loops, the at least one fixation loop, and the adjustable knot. The flexible elongate element may be arranged so that it successively forms a first one of the bone-side loops, the fixation loop, a second one of the bone-side loops, and the adjustable knot.

The adjustable knot, and the fixation loop (and optionally also a bone-side loop), may together form a self-locking knot assembly. The self-locking knot assembly may self-lock under load, which may be a tensile load imparted on the bone-side loops. A length of the bone-side loops may therefore be automatically locked or fixed when the bone-side loops are placed under tension. This may be achieved because tensioning the bone-side loops may both bring the adjustable knot on to the outer surface of the fixation device, and cause the fixation loop to lock said part of the adjustable knot arrangement.

The bone-side loops may be adjustable in length by manipulation of the fixation loop and the adjustable knot. In particular, adjustment of the length of the bone-side loops may be achieved by releasing tension applied to the bone-side loops, releasing the fixation loop from said part of the adjustable knot arrangement, adjusting a location of the knot along a length of the flexible elongate element, and then re-tensioning the bone-side loops. Adjusting the location of the knot along the length of the flexible elongate element may increase or decrease lengths of each of the first and second legs, thereby providing less material in the bone-side loops (to decrease their length), or more material in the bone-side loops (to increase their length), respectively.

The adjustable knot may be positioned between the outer surface of the fixation device and the fixation loop. In this way, tension applied to the bone-side loops may draw the knot towards the outer surface and the fixation loop towards the knot, to clamp said part of the adjustable knot arrangement. The knot may be held in position by a combination of tension in the bone-side loop extending from the knot on the bone facing surface of the fixation device, and tension in the bone-side loop extending from the fixation loop.

The implant assembly may comprise at least one further bone-side loop which extends from one of the apertures at the bone facing surface of the fixation device to another one of the apertures at the bone facing surface. The further bone-side loop may form a support loop adapted to be located within a bone tunnel. The assembly may therefore comprise first, second and third bone-side loops, which may each be support loops.

The implant assembly may comprise at least one further fixation loop which extends from one of the apertures at the outer surface of the fixation device to another one of the apertures at the outer surface of the fixation device. The fixation loop may be a first fixation loop and the further fixation loop may be a second fixation loop. The further fixation loop may pass over at least part of the adjustable knot arrangement. The first and at least one further fixation loop may act together to clamp the adjustable knot arrangement to the fixation device when the bone-side loops are tensioned relative to the fixation device. At least one fixation loop may extend from a first aperture at the outer surface to a second aperture at the outer surface. At least one further fixation loop may extend from a third aperture at the outer surface to a fourth aperture at the outer surface.

The implant assembly may be an implant fixation assembly for fixing an implant within a tunnel in a bone. The implant assembly may comprise an implant, which may be a graft. The fixation device may be for securing the implant relative to the bone, the implant being suspended from the fixation device within the bone tunnel. The implant may therefore be indirectly coupled to the fixation device. The implant assembly may comprise a captive and/or continuous loop for supporting the implant, which loop may be disposed through at least one of the bone-side loops. The or each bone-side loop which forms a support loop may be an implant support loop adapted to receive the implant, for suspending the implant in the bone tunnel from the fixation device. The implant may serve to replicate the function of damaged tissue, for example at least one ligament or tendon. Coupling of the implant to the support loop(s) may enable tensioning of the implant, supported by contact between the bone facing surface of the fixation device and bone surrounding an opening of the bone tunnel. Suitable implants include synthetic implants, and may be fabric implants, particularly implants comprising or formed of a woven material. Woven fabrics have good tensile strength (in a direction along warp fibres of the fabric), whilst facilitating tissue ingrowth into apertures between the warp and weft fibres.

The or each bone-side loop which forms a support loop may form an implant, which may be a graft. The implant may serve to replicate the function of damaged tissue, for example at least one ligament or tendon. The implant that is formed by the support loop(s) may therefore be directly coupled to the fixation device. The support loop(s) may serve for repairing a distracted bone joint (such as bones of a syndesmotic joint or of an acromioclavicular joint or ACJ), by holding distracted bones in their proper position.

The bone-side loops may each have a first loop portion extending from one of the apertures to an apex of the loop, and a second loop portion extending from said other aperture to the apex of the loop.

The fixation loop may have a first loop portion extending from one of the apertures to an apex of the loop, and a second loop portion extending from said other aperture to the apex of the loop.

The adjustable knot may have a first knot portion extending from one side (or end) of the knot to one of the apertures, and a second knot portion extending from the other side (or end) of the knot to said other the aperture.

The first loop portion of one of the bone-side loops may extend from one side of the knot, and the second loop portion of the bone-side loops may extend from one of the first and second loop portions of the fixation loop. The first loop portion of the other bone-side loop may extend from the other side of the knot, and the second loop portion of the other bone-side loop may extend from the other one of the first and second loop portions of the fixation loop.

The fixation device of the implant assembly may be a first fixation device, and the assembly may comprise a second fixation device comprising a bone facing surface, an outer surface opposite the bone facing surface, a first aperture extending through the fixation device from the outer surface to the bone facing surface, and at least a second aperture extending through the fixation device from the outer surface to the bone facing surface. The first and second fixation devices may cooperate to restore bones of a syndesmotic joint or ACJ to their proper position, the first fixation device adapted to be secured relative to a surface of a first bone of the joint and the second fixation device relative to a surface of a second bone of the joint. At least one of the bone-side loops may extend along a bone tunnel between the fixation devices to maintain the bones in their proper position, a length of the loop(s) being selected to define a desired distance between the two fixation devices.

The flexible elongate element may also pass through the apertures of the second fixation device, and may suitably pass through one of the apertures and then back through another one of the apertures of the second fixation device. The second fixation device may be arranged so that its bone facing surface faces towards the bone facing surface of the first fixation device. The second fixation device may be disposed on one or more of the bone-side loops. The second fixation device may be located at a position which is spaced along a length of said bone-side loop from the first fixation device. Portions of said bone-side loop extending between the bone facing surfaces of the first and second fixation devices may define an implant, for location in the bone tunnel. Adjustment of the lengths of said bone-side loop may adjust a length of the implant that is formed, and may adjust a distance between the first and second fixation devices. This may enable adjustment of the implant assembly to account for anatomical differences from patient-to-patient.

Where one or more of the bone-side loops form an implant, the implant may be a first implant and the implant assembly may comprise a separate, further implant. The further implant may be coupled directly to the fixation device and may be tensionable independently of the first implant (said bone-side loop). The fixation device may comprise at least one further aperture extending through the fixation device from the outer surface to the bone facing surface, and may comprise third and fourth such apertures. The further implant may be directly coupled to the fixation device by passing the implant through the at least one further aperture. Suitably, the further implant may extend from the third aperture at the bone facing surface of the fixation device to the fourth aperture at the bone facing surface, to form a further bone-side loop. Where the implant assembly comprises a further fixation device, the further implant may be coupled to the further fixation device. The further implant may be secured to the further fixation device by the flexible elongate element, for example by looping the flexible elongate element over the further implant to clamp it to the outer surface of the further fixation device. Suitable implants include synthetic implants, for example fabric implants, particularly implants comprising or formed of a woven material.

The implant assembly may comprise a tubular sheath, which may be positioned around the bone-side loop or loops adapted to be located in the bone tunnel. The tubular sheath may be synthetic, and may be of a fabric, particularly a fabric comprising or formed of a woven material. The tubular sheath may promote tissue ingrowth. Providing a sheath which is tubular may facilitate fitting of the sheath around the bone-side loop or loops. Providing the sheath of a fabric, particularly woven material, may enable the sheath to easily decrease in length (and increase in width), or increase in length (and decrease in width) according to the desired lengths of the bone-side loops. This may help to fill the bone tunnel, promoting tissue ingrowth.

The implant assembly may be for use in tissue repair in the human or animal body, and may for example be for use in an ACL repair procedure, a syndesmotic joint repair procedure, or an ACJ repair procedure.

The fixation loop may extend at least partly over the adjustable knot. The fixation loop may be arranged so that it passes: over the adjustable knot; over one of the first and second legs; and/or over both the first and second legs, to clamp the knot arrangement to the fixation device when the bone-side loops are tensioned.

The second aperture of the fixation device may be spaced from the first aperture. The fixation device may be elongate. The second aperture may be spaced from the first aperture along a length of the device and/or along a width of the device. Where further apertures are provided, they may be spaced along a length and/or width of the device from at least one other aperture.

The apertures may each have an opening on or in the bone facing surface of the fixation device, and an opening on or in the outer surface. The bone-side loops may each extend between openings of the apertures which are on or in the bone facing surface. The fixation loop may extend between openings which are on or in the outer surface.

At least one bone-side loop may be adapted to be drawn into contact with the bone-facing surface of the fixation device, suitably by shortening the loop, said bone-side loop cooperating with the fixation loop and the knot assembly to secure the flexible elongate element to the fixation device. Said bone-side loop may form a locking loop. Said loop may be shorter than the bone side loop forming a support loop. In the implant assembly that is thereby formed, adjustment of a length of the support loop may advantageously be achieved by applying tension to one of the first and second loop portions of the support loop, suitably the loop portion which extends from one side of the knot. Adjustment may be achieved by adjusting the knot, suitably by decreasing a length of one of the legs. Applying tension to the other loop portion, which extends from the fixation loop, may serve to lock a length of the support loop. The implant assembly may comprise a knot-adjusting element for adjusting the knot. The knot-adjusting element may be coupled to the loop portion which extends from said side of the knot. Applying tension to the knot-adjusting element may therefore adjust the length of said leg. The knot-adjusting element may be secured to the support loop, suitably by knotting, tying or bonding.

The flexible elongate element may be a suture. The flexible elongate element may be a multifilament element. The flexible elongate element may be braided, which may enhance tissue ingrowth. As is well known, a braid structure for the elongate element may comprise a first set of fibres passing in a first direction around a circumference of the elongate element, and a second set of fibres passing in a second direction around a circumference of the elongate element, the first fibres disposed transverse to the second fibres. Fibres forming the braid may be disposed transverse to a longitudinal axis of the elongate element. A braid angle may be defined between the fibres and the longitudinal axis. The braid angle may be no more than around 30°, may be no more than around 25°, may be no more than around 20°, and may be around 15°. The braid angle may be no less than around 15°. The braid angle may be between around 15° and around 30°. Providing a braid angle which is small (in the range of between around 15° and around 30°, and particularly around 15°) may provide advantages. These may include that a degree of extension of the elongate element (and so the bone-side loops) may be restricted, in comparison to prior braided implant assemblies having a similar operative length to that defined by the bone-side loops; a greater recovery in the absence of or under reduced loading (and so a behaviour more alike to native tissue); and/or that the braided structure may be relatively 'open', defining elongate generally diamond-shaped openings which promote tissue ingrowth following implantation.

The flexible elongate element may be hollow and may be tubular. The flexible elongate element may comprise filaments which are twisted together. The flexible elongate element may take the form of a cord or the like. The flexible elongate element may be a monofilament. The flexible elongate element may be a fabric element, and may comprise or be formed of a woven material. This may provide good tensile strength (in a direction along warp fibres of the fabric), whilst facilitating tissue ingrowth into apertures between the warp and weft fibres.

The free ends of the flexible elongate element may be directed from the outer surface side of the fixation device and through the fixation device, suitably through selected ones of the first and second apertures (or third/fourth apertures where provided).

The fixation device may take the form of a button, and may be an Endobutton™. A suitable fixation device is disclosed in the applicant's International Patent Publication no. WO-2016/063019, the disclosure of which is incorporated herein by this reference.

The implant assembly may comprise a plug, which may facilitate location of the implant assembly in a bone tunnel or channel. The plug may be coupled or couplable to an implant such as a prosthetic implant, which may be tubular defining a cavity which can receive the plug. The plug may comprise a passage extending through it, and at least part of at least one bone side loop may be located or locatable through the passage. The plug may be a bone plug, which may be taken from a bone of a patient (autologous bone). Other plugs, including implantable artificial ones, may be employed. Reference is made to prior International Patent Publication no. WO-89/10101, the disclosure of which is incorporated herein by this reference.

According to a second aspect of the present invention, there is provided a method of manufacturing an implant assembly for use in tissue repair, the method comprising the steps of:

providing a fixation device comprising a bone facing surface, an outer surface opposite the bone facing surface, a first aperture extending through the fixation device from the outer surface to the bone facing surface, and at least a second aperture extending through the fixation device from the outer surface to the bone facing surface;

coupling a flexible elongate element to the fixation device by passing the elongate element through apertures of the fixation device to form:

at least two bone-side loops which each extend from at least one of the apertures at the bone facing surface of the fixation device, at least one of the bone-side loops forming a support loop adapted to be located at least partly within a bone tunnel;

at least one fixation loop which extends from one of the apertures at the outer surface of the fixation device to another one of the apertures at the outer surface of the fixation device; and an adjustable knot arrangement comprising an adjustable knot, a first leg extending from the knot to a first free end of the elongate element and a second leg extending from the knot to a second free end of the elongate element;

and arranging the fixation loop so that it passes over at least part of the adjustable knot arrangement.

Where the fixation device comprises a first aperture and a second aperture (for accommodating the flexible elongate element), the method may comprise:

providing said bone-side loops extending from one of the apertures at the bone facing surface of the fixation device to the other one of the apertures at the bone facing surface; and providing said fixation loop extending from one of the apertures at the outer surface of the fixation device to the other one of the apertures at the outer surface of the fixation device.

One or more of the bone-side loops that are formed may extend from one of the apertures at the bone facing surface of the fixation device to another one of the apertures at the bone facing surface.

One or more of the bone-side loops that are formed may extend from a same aperture at the bone facing surface of the fixation device. In other words, the flexible elongate element forming said loop may extend from an aperture of the fixation device on the bone-facing surface side of the fixation device, and may then follow a path which forms the bone-side loop before passing back through the fixation device to the outer surface side through the same aperture.

The method may comprise directing the flexible elongate element through the first aperture of the fixation device and through another, optionally a second, aperture, so that a portion of the flexible elongate element including the first free end and a portion of the flexible elongate element including the second free end both extend from the apertures on an outer surface side of the fixation device, to form one of the bone-side loops (which may form a step A of the method). The bone-side loop that is formed is on a bone facing surface side of the fixation device.

The method may comprise directing the portion of the flexible elongate element which extends from the first aperture on the outer surface side of the fixation device through another, optionally a second, aperture, so that said portion extends from the other aperture on the bone facing surface side of the fixation device, to form the fixation loop (which may form a step B of the method). The fixation loop that is formed in on the outer surface side of the fixation device.

The method may comprise directing the portion of the flexible elongate element which extends from the other, optionally second, aperture on the bone facing surface side of the fixation device through the first aperture, so that the portions of the flexible elongate element including the first and second free ends both extend from the apertures on the outer surface side of the fixation device, to form the other one of the bone-side loops (which may form a step C of the method). The other bone-side loop that is formed is on the bone facing surface side of the fixation device.

The method may comprise manipulating the portions of the flexible elongate element to form the adjustable knot (which may form a step D of the method).

The method may comprise manipulating the adjustable knot so that it is positioned between the outer surface of the fixation device and the fixation loop (which may form a step E of the method). This may be achieved by directing one or both of the portions of the flexible elongate element through the fixation loop, suitably through an eye of the fixation loop.

The method may comprising manipulating the fixation loop to clamp the adjustable knot arrangement to the fixation device and thereby secure the flexible elongate element to the fixation device (which may together form a step F of the method).

Steps E and F of the method may be carried out by tensioning the bone-side loops.

The steps A to F may be carried out sequentially.

The method may comprise, following step C, directing the portion of the flexible elongate element which extends from the first aperture on the outer surface side of the fixation device back through another, optionally the second, aperture, so that said portion extends from the other aperture on the bone facing surface side of the fixation device, to form a further fixation loop (which may form a step C2 of the method).

The method may comprise, following step C2, directing the portion of the flexible elongate element which extends from the other aperture of the fixation device on the bone facing surface side through the first aperture, so that the portions of the flexible elongate element including the first and second free ends again both extend from the apertures on the outer surface side of the fixation device, to form a further bone-side loop (which may form a step C3 of the method).

Where the method comprises steps C2 and C3, step E may involve directing said portion(s) of the flexible elongate element through both of the fixation loops, suitably through eyes of the fixation loops. Step F may involve manipulating both of the fixation loops to clamp the adjustable knot arrangement to the fixation device and thereby secure the flexible elongate element to the fixation device.

The fixation device may be a first fixation device, and the method may comprise providing a further fixation device comprising a bone facing surface, an outer surface opposite the bone facing surface, a first aperture extending through the further fixation device from the outer surface to the bone facing surface, and at least a second aperture extending through the further fixation device from the outer surface to the bone facing surface. The method, in step A, and optionally also in step C, may comprise directing the flexible elongate element through the first aperture and another, suitably a second aperture, of the further fixation device so that the further fixation device is disposed on the bone-side loop that is formed in step A, and optionally also the bone-side loop that is formed in step C. The method may comprise arranging the further fixation device so that its bone facing surface faces towards the bone facing surface of the first fixation device.

The method may comprise drawing one of the bone-side loops into contact with the bone-facing surface of the fixation device, suitably by shortening the loop, said bone-side loop cooperating with the fixation loop and the knot assembly to secure the flexible elongate element to the fixation device. The support loop may comprise a first loop portion extending from one of the apertures to an apex of the loop, and a second loop portion extending from the other one of the apertures to the apex of the loop. The method may comprise adjusting a length of the support loop by applying tension to one of the first and second loop portions, suitably the loop portion which extends from one side of the knot. Adjustment may be achieved using a knot-adjusting element coupled to the loop portion which extends from said side of the knot.

The method may comprise directing free ends of the flexible elongate element from the outer surface side of the fixation device and through the fixation device, suitably through selected ones of the first and second apertures (or further, e.g. third/fourth apertures where provided). This may have a particular use in a syndesmotic joint repair procedure, as it may enable adjustment of the knot (and so a length of the support loop and thus the implant assembly) from an end of a bone tunnel which is opposite to the end at which the knot is located. For example, the knot may be located on a medial end of a tunnel in a syndesmotic ankle joint, and the knot adjusted from the lateral end of the tunnel. This may be achieved by arranging the flexible elongate element so that it extends along the tunnel from the fixation device, with the free ends protruding from the tunnel at the end which is opposite to the fixation device.

The method may comprise positioning a tubular sheath around the bone-side loops. The tubular sheath may promote tissue ingrowth.

The method may comprise the step of positioning a plug on at least part of at least one bone side loop. The plug may be of the type described above. The plug may comprise a passage extending through it, and the method may comprise locating at least part of at least one bone side loop through the passage.

Further features of the method of the second aspect of the present invention may be derived from the text set out elsewhere in this document, in particular in or with reference to the first aspect of the invention.

According to a third aspect of the present invention, there is provided a method of carrying out tissue repair involving the fixation of an implant within a tunnel in a bone, the method comprising use of the implant assembly of the first aspect of the invention to locate an implant in a tunnel in a bone.

According to a fourth aspect of the present invention, there is provided a method of surgical implantation of a prosthetic implant in a boney joint requiring repair, in which the implant is introduced in a bone channel formed in at least one bone forming part of the boney joint, and optionally in which the bone channel is formed in at least two bones which together form the boney joint, the method comprising the steps of:
  providing an implant assembly according to the first aspect of the invention;
  locating the fixation device of the implant assembly adjacent a surface of a bone of the boney joint comprising at least part of the bone channel, so that at least part of at least one of the bone-side loops is positioned in said channel; and
  tensioning the bone-side loops to lock a length of the loops and so a length of the implant assembly.

The bone-side loops may define the implant. Alternatively, the method may comprise coupling a separate implant to the bone-side loops.

The method may be a method of repairing damaged connective tissue, which may comprise a ligament or tendon. The method may be a method of repairing a damaged ACL, a damaged syndesmotic joint or a damaged ACJ. Methods of repairing a damaged ACJ which may employ the implant assembly of the present invention are disclosed in prior International Patent Publication no. WO-2017/013431, in which the present applicant is a joint applicant, and the disclosure of which is incorporated herein by this reference.

Further features of the method of the third and fourth aspects of the present invention may be derived from the text set out elsewhere in this document, in particular in or with reference to the first and/or second aspect of the invention.

According to a fifth aspect of the present invention, there is provided an implant construction device for forming an implant assembly adapted to be used in tissue repair, the implant construction device comprising:
  a fixation device comprising a bone facing surface, an outer surface opposite the bone facing surface, a first aperture extending through the fixation device from the outer surface to the bone facing surface, and at least a second aperture extending through the fixation device from the outer surface to the bone facing surface;
  a flexible elongate element coupled to the fixation device; and
  a manipulating element for use in constructing the implant assembly, the manipulating element being flexible and elongate and comprising a first end forming at least part of a capturing loop and a second end, the manipulating element extending through an aperture of the fixation device so that a portion of the manipulating element comprising its first end extends from the aperture at the bone facing surface of the fixation device and a portion of the manipulating element comprising its second end extends from the aperture at the outer surface of the fixation device; and
  an adjustable knot which is positionable on the outer surface of the fixation device;
  in which the flexible elongate element has a first end and a second end, and the flexible elongate element passes through apertures of the fixation device so that:
  a bone-side loop is formed which extends from at least one of the apertures at the bone facing surface of the fixation device;
  a knot fixation loop is formed which extends from one of the apertures at the outer surface of the fixation device to another one of the apertures at the outer surface of the fixation device; and
  a portion of the flexible elongate element comprising the first end extends from one of the apertures at the outer surface of the fixation device and a portion of the flexible elongate element comprising the second end extends from one of the apertures at the bone facing surface of the fixation device;
  and in which the adjustable knot is formed by the portion of the manipulating element extending from said aperture of the fixation device and comprising its second end, and the portion of the flexible elongate element extending from said aperture of the fixation device and comprising its first end.

According to a sixth aspect of the present invention, there is provided an implant construction device for forming an implant assembly adapted to be used in tissue repair, the implant construction device comprising:
  a fixation device comprising a bone facing surface, an outer surface opposite the bone facing surface, a first aperture extending through the fixation device from the outer surface to the bone facing surface, and at least a second aperture extending through the fixation device from the outer surface to the bone facing surface;

a flexible elongate element coupled to the fixation device; and first and second manipulating elements for use in constructing the implant assembly, the manipulating elements being flexible and elongate and each comprising a first end forming at least part of a capturing loop and a second end, the manipulating elements each extending through an aperture of the fixation device so that portions of the manipulating elements comprising their first ends extend from said aperture at the bone facing surface of the fixation device and portions of the manipulating elements comprising their second ends extend from said aperture at the outer surface of the fixation device; and an adjustable knot which is positionable on the outer surface of the fixation device;

in which the flexible elongate element has a first end and a second end, and the flexible elongate element passes through apertures of the fixation device so that:

a bone-side loop is formed which extends from at least one of the apertures at the bone facing surface of the fixation device;

a first knot fixation loop is formed which extends from one of the apertures at the outer surface of the fixation device to another one of the apertures at the outer surface of the fixation device;

a second knot fixation loop is formed which extends from one of the apertures at the outer surface of the fixation device to another one of the apertures at the outer surface of the fixation device;

a portion of the flexible elongate element comprising the first end, and a portion of the flexible elongate element comprising the second end, each extend from one of the apertures at the bone facing surface of the fixation device;

and in which the adjustable knot is formed by a portion of the first manipulating element extending from said aperture of the fixation device and comprising its second end, and a portion of the second manipulating element extending from said aperture of the fixation device and comprising its second end.

The implant construction devices of the fifth and sixth aspects of the invention may have a use in forming any of the implant assemblies disclosed in this document. The implant construction devices may provide the advantage that the implant assemblies which are formed using the construction devices can be adapted to the particular needs of a patient and/or a surgical procedure, such as by a surgeon or other skilled operator. Parts of the implant construction device which are common to parts of the implant assembly formed employing the device may have any of the further features or characteristics described in this document.

In relation to the implant construction devices disclosed in this document, reference is made to a manipulating element. The terms construction element, sacrificial element and transient element may be used interchangeably with the term manipulating element.

Optional further features of the implant construction devices of the fifth and sixth aspects of the invention are as follows.

One or more of the bone-side loops that are formed may extend from one of the apertures at the bone facing surface of the fixation device to another one of the apertures at the bone facing surface.

One or more of the bone-side loops that are formed may extend from a same aperture at the bone facing surface of the fixation device. In other words, the flexible elongate element forming said loop may extend from an aperture of the fixation device on the bone-facing surface side of the fixation device, and may then follow a path which forms the bone-side loop before passing back through the fixation device to the outer surface side through the same aperture.

The portion of the manipulating element(s) comprising the first end and extending from said aperture at the bone facing surface of the fixation device may define the entire capturing loop.

The capturing loop(s) may be defined partly by the portion of the manipulating element comprising the first end and extending from said aperture at the bone facing surface of the fixation device, and partly by the portion of the manipulating element comprising the second end and extending from said aperture at the outer surface of the fixation device. The capturing loop may be bound at least partly by the fixation device, in particular by its bone facing surface.

The manipulating element(s) may be defined by a single elongate element which is folded at a point along its length to form the capturing loop. The manipulating element may be of a textile material, and may be woven or braided. The manipulating element may be generally tubular. A part of the manipulating element may extend through a side wall of the element and along an internal cavity, to form the capturing loop. The manipulating element may be secured to itself at a point along its length to form the capturing loop, for example by a knot.

The adjustable knot may be an overhand knot. The adjustable knot may be adapted to be positioned between the outer surface of the fixation device and the fixation loop. Where there is more than one fixation loop, the adjustable knot may be adapted to be positioned between the outer surface of the fixation device and each of the fixation loops.

The bone-side loop may form a support loop adapted to be located at least partly within a bone tunnel.

Optional further features of the implant construction device of the fifth aspect of the invention are as follows.

The second end of the flexible elongate element may be positionable through the capturing loop of the manipulating element, and the manipulating element may be manipulatable to draw the second end through the fixation device to its outer surface and through the adjustable knot, so that the portion of the knot formed by the manipulating element is replaced by the portion of the flexible elongate element comprising its second end.

The adjustable knot may form part of an adjustable knot arrangement comprising the adjustable knot, a first leg extending from the knot and a second leg extending from the knot, the portions of the manipulating element and the flexible elongate element forming the knot also forming the first and second knot legs.

The flexible elongate element may be arranged so that it follows a path which extends continuously through the apertures in the fixation device to form the bone-side loop, the at least one fixation loop, and its part of the adjustable knot.

The first end of the manipulating element may be adapted to be located through a plug, which may facilitate location of the implant assembly which is formed using the implant construction device in a bone tunnel or channel, and/or which may facilitate tissue ingrowth into the tunnel. The plug may be coupled or couplable to an implant such as a prosthetic implant, which may be tubular defining a cavity which can receive the plug. The plug may comprise a passage extending through it, and the first end of the manipulating element may be adapted to be located through the passage. Manipulation of the manipulating element may serve to draw the second end of the flexible elongate element through the plug and through the fixation device to its outer surface side, so that the plug is positioned on the bone side loop which is thereby formed. The plug may be a bone plug, which may be taken from a bone of a patient (autologous bone). Other plugs, including implantable artificial ones, may be employed.

The bone side loop may be adapted to be located through a plug of the type described in the previous paragraph, and may be adapted to be located through the passage of the plug. The second free end of the flexible elongate element may be adapted to be located through a part of the bone side loop protruding from the plug, suitably through an eye of the loop, and may then be positionable through the capturing loop of the manipulating element. Manipulation of the manipulating element to draw the second end of the flexible elongate element through the fixation device to its outer surface side may then form a second bone side loop, which may pass through and so may be coupled to the bone side loop carrying the plug, and which may secure the plug to the fixation device.

Optional further features of the implant construction device of the sixth aspect of the invention are as follows.

The first end of the flexible elongate element may be positionable through the loop of the first manipulating element. The second end of the flexible elongate element may be positionable through the loop of the second manipulating element. The manipulating elements may be manipulatable to draw the first and second ends of the flexible elongate element through the fixation device to its outer surface and through the adjustable knot, so that the portion of the adjustable knot formed by the first manipulating element is replaced by the portion of the flexible elongate element comprising its first end, and so that the portion of the adjustable knot formed by the second manipulating element is replaced by the portion of the flexible elongate element comprising its second end.

The flexible elongate element may be arranged so that it follows a path which extends continuously through the apertures in the fixation device to form one of the fixation loops, the bone-side loop, and the other fixation loop.

The adjustable knot may form part of an adjustable knot arrangement comprising the adjustable knot, a first leg extending from the knot and a second leg extending from the knot, said portions of the manipulating elements forming the first and second knot legs.

The first ends of both the first and second manipulating elements may be adapted to be located through a plug of the type described above. The first ends of the manipulating elements may be adapted to be located through the plug passage. Manipulation of the manipulating elements may serve to draw the first and second ends of the flexible elongate element through the plug and through the fixation device to its outer surface side, so that the plug is positioned on the bone side loops which are thereby formed.

According to a seventh aspect of the present invention, there is provided a method of manufacturing an implant construction device for use in forming an implant assembly adapted to be used in tissue repair, the method comprising the steps of:

providing a fixation device comprising a bone facing surface, an outer surface opposite the bone facing surface, a first aperture extending through the fixation device from the outer surface to the bone facing surface, and at least a second aperture extending through the fixation device from the outer surface to the bone facing surface;

coupling a flexible elongate element comprising a first end and a second end to the fixation device;

providing a flexible elongate manipulating element comprising a first end forming at least part of a capturing loop and a second end, and locating the manipulating element through an aperture of the fixation device so that a portion of the manipulating element comprising its first end extends from the aperture at the bone facing surface of the fixation device and a portion of the manipulating element comprising its second end extends from the aperture at the outer surface of the fixation device;

in which the step of coupling the flexible elongate element to the fixation device involves passing the flexible elongate element through apertures of the fixation device to form a bone-side loop which extends from at least one of the apertures at the bone facing surface of the fixation device, and a knot fixation loop which extends from one of the apertures at the outer surface of the fixation device to another one of the apertures at the outer surface of the fixation device, a portion of the flexible elongate element comprising the first end extending from one of the apertures at the outer surface of the fixation device and a portion of the flexible elongate element comprising the second end extending from one of the apertures at the bone facing surface of the fixation device (which may be different apertures for each portion);

and in which the method further comprises:

forming an adjustable knot using the portion of the manipulating element extending from said aperture of the fixation device and comprising its second end, and the portion of the flexible elongate element extending from said aperture of the fixation device and comprising its first end; and arranging the adjustable knot so that fixation loop passes over the knot.

The method may comprise positioning the second end of the flexible elongate element through the capturing loop of the manipulating element, and using the manipulating element to draw the second end through the fixation device to its outer surface and through the adjustable knot, so that the portion of the knot formed by the manipulating element is replaced by the portion of the flexible elongate element comprising its second end. A further bone-side loop may then be formed by the flexible elongate element. Completion of this step may form an implant assembly which is ready for implantation in a body of a patient.

The method may comprise locating the first end of the manipulating element through a plug, which may be a plug of the type described above. The first end of the manipulating element may be located through the plug passage. The method may comprise using the manipulating element to draw the second end of the flexible elongate element through the plug and through the fixation device to its outer surface side, to form a bone side loop with the plug positioned on the loop. Completion of this step may form an implant assembly which is ready for implantation in a body of a patient.

The method may comprise locating the bone side loop through a plug, which may be a plug of the type described above. The bone side loop may be located through the plug passage. The method may comprise locating the second free end of the flexible elongate element through a part of the bone side loop protruding from the plug, suitably through an eye of the loop, and then positioning the second free end through the capturing loop of the manipulating element. The method may comprise using the manipulating element to draw the second end of the flexible elongate element through the fixation device to its outer surface side, to form a further bone side loop coupled to the bone side loop carrying the plug. Completion of this step may form an implant assembly which is ready for implantation in a body of a patient.

According to an eighth aspect of the present invention, there is provided a method of manufacturing an implant construction device for use in forming an implant assembly adapted to be used in tissue repair, the method comprising the steps of:
- providing a fixation device comprising a bone facing surface, an outer surface opposite the bone facing surface, a first aperture extending through the fixation device from the outer surface to the bone facing surface, and at least a second aperture extending through the fixation device from the outer surface to the bone facing surface;
- coupling a flexible elongate element comprising a first end and a second end to the fixation device;
- providing first and second flexible elongate manipulating elements, each manipulating element comprising a first end forming at least part of a capturing loop and a second end, and locating the manipulating elements through an aperture of the fixation device (which may be different apertures for each manipulating element) so that portions of the manipulating elements comprising their first ends extend from the aperture at the bone facing surface of the fixation device and portions of the manipulating elements comprising their second ends extend from the aperture at the outer surface of the fixation device;
- in which the step of coupling the flexible elongate element to the fixation device involves passing the flexible elongate element through apertures of the fixation device to form:
- a bone-side loop which extends from at least one of the apertures at the bone facing surface of the fixation device;
- a first knot fixation loop which extends from one of the apertures at the outer surface of the fixation device to another one of the apertures at the outer surface of the fixation device; and
- a second knot fixation loop which extends from one of the apertures at the outer surface of the fixation device to another one of the apertures at the outer surface of the fixation device;
- in which a portion of the flexible elongate element comprising the first end, and a portion of the flexible elongate element comprising the second end, each extend from one of the apertures at the bone facing surface of the fixation device (which may be different apertures for each portion);
- and in which the method further comprises:
- forming an adjustable knot using the portion of the first manipulating element extending from said aperture of the fixation device and comprising its second end, and the portion of the second manipulating element extending from said aperture of the fixation device and comprising its second end; and
- arranging the adjustable knot so that the fixation loops pass over the knot.

The method may comprise positioning the first end of the flexible elongate element through the capturing loop of the first manipulating element, and using the first manipulating element to draw the first end through the fixation device to its outer surface and through the adjustable knot, so that the portion of the knot formed by the first manipulating element is replaced by the portion of the flexible elongate element comprising its first end. The method may comprise positioning the second end of the flexible elongate element through the capturing loop of the second manipulating element, and using the second manipulating element to draw the second end through the fixation device to its outer surface and through the adjustable knot, so that the portion of the knot formed by the second manipulating element is replaced by the portion of the flexible elongate element comprising its second end. Completion of these steps may form an implant assembly which is ready for implantation in a body of a patient.

The method may comprise locating the first ends of the manipulating elements through a plug, which may be a plug of the type described above. The first ends of the manipulating elements may be located through the plug passage. The method may comprise using the manipulating elements to draw the first and second ends of the flexible elongate element through the plug and through the fixation device to its outer surface side, to form first and second bone side loops with the plug positioned on the loops. Completion of these steps may form an implant assembly which is ready for implantation in a body of a patient.

In the methods of the seventh and eighth aspects of the invention, one or more of the bone-side loops that are formed may extend from one of the apertures at the bone facing surface of the fixation device to another one of the apertures at the bone facing surface. One or more of the bone-side loops that are formed may extend from a same aperture at the bone facing surface of the fixation device. In other words, the flexible elongate element forming said loop may extend from an aperture of the fixation device on the bone-facing surface side of the fixation device, and may then follow a path which forms the bone-side loop before passing back through the fixation device to the outer surface side through the same aperture.

Further features of the methods of the seventh and eighth aspects of the present invention may be derived from the text set out elsewhere in this document, including the text relating to any one of the first to sixth aspects.

In a further aspect or aspects of the invention, there is provided a method of manufacturing an implant assembly for use in tissue repair, involving a preparatory step of manufacturing an implant construction device according to the seventh and/or eighth aspect of the invention, and then carrying out further steps as specified above in order to complete the implant assembly.

In a still further aspect or aspects of the present invention, there is provided a method of carrying out tissue repair involving the fixation of an implant within a tunnel in a bone, the method comprising use of the implant construction device of the fifth or sixth aspect of the invention to form an implant assembly, and using the implant assembly to fix the implant, or to provide the implant. The implant assembly which is formed may have the features of any one of the implant assemblies disclosed in this document.

Embodiments of the present invention will now be described, by way of example only, with reference to the accompanying drawings, in which.

Figure 32:
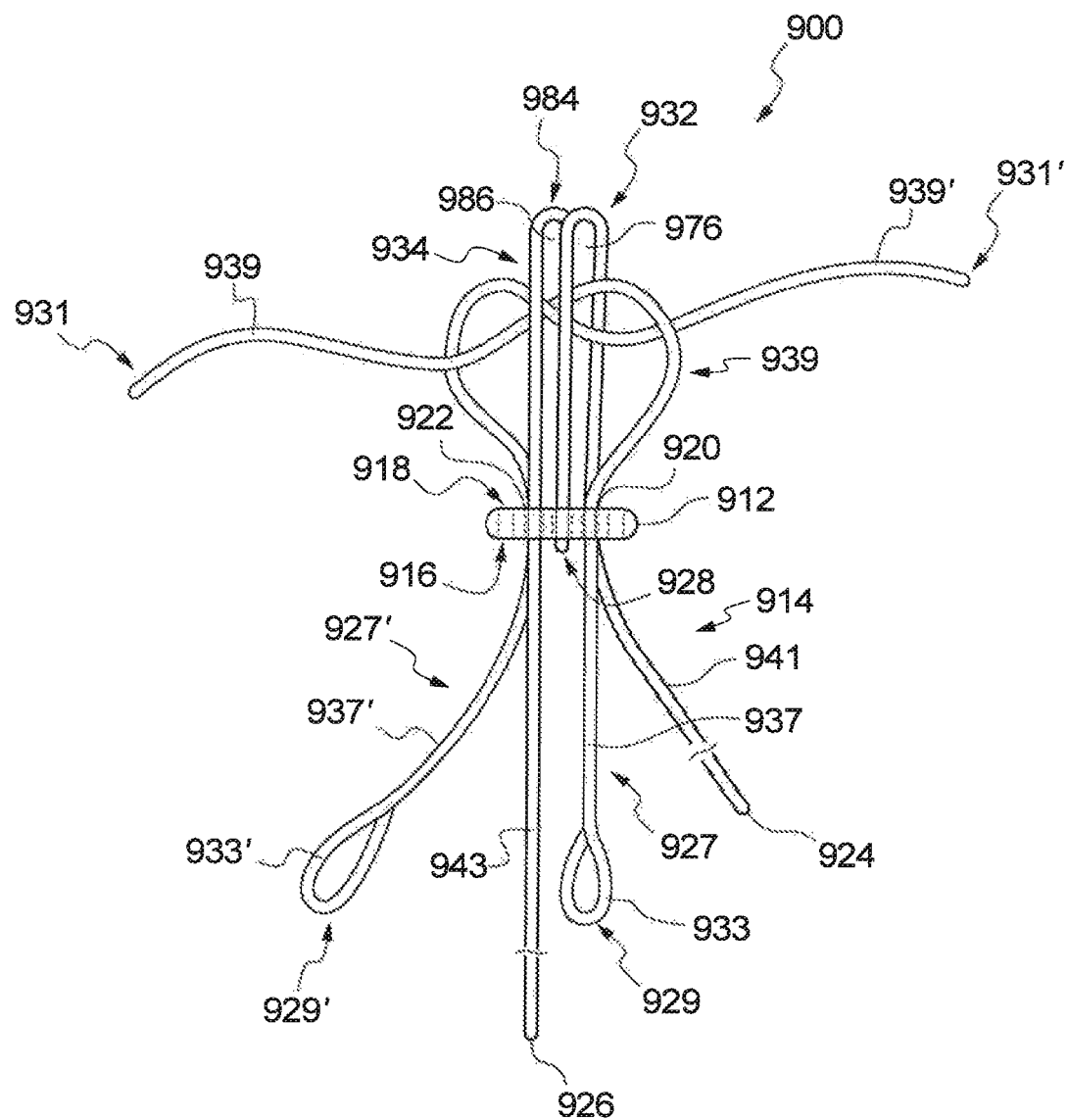
FIG. 32 is a front view of an implant construction device for forming an implant assembly adapted to be used in tissue repair, in accordance with another embodiment of the present invention, the implant construction device shown in an assembled state.
Figure 39:
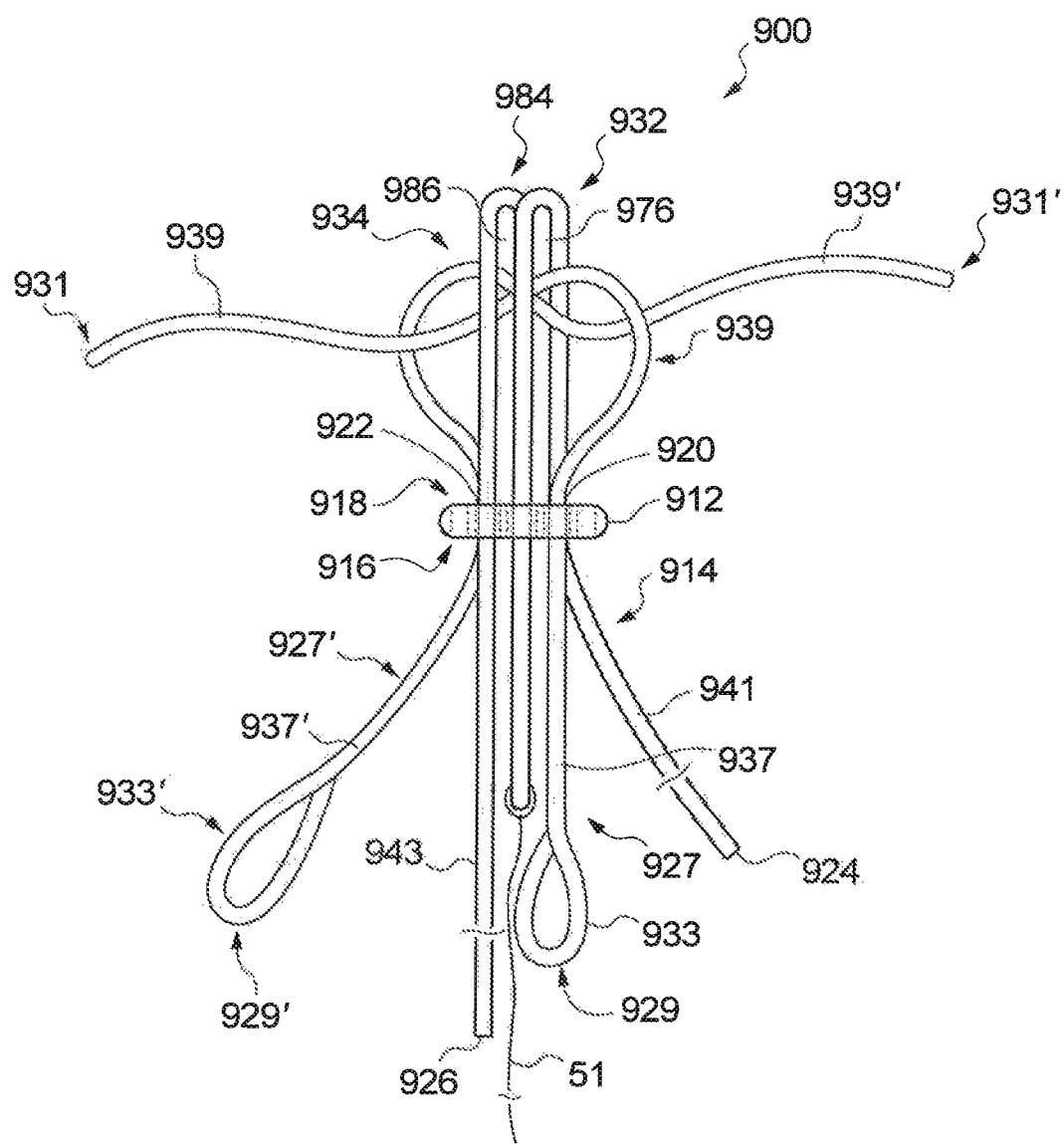
Figure 40:
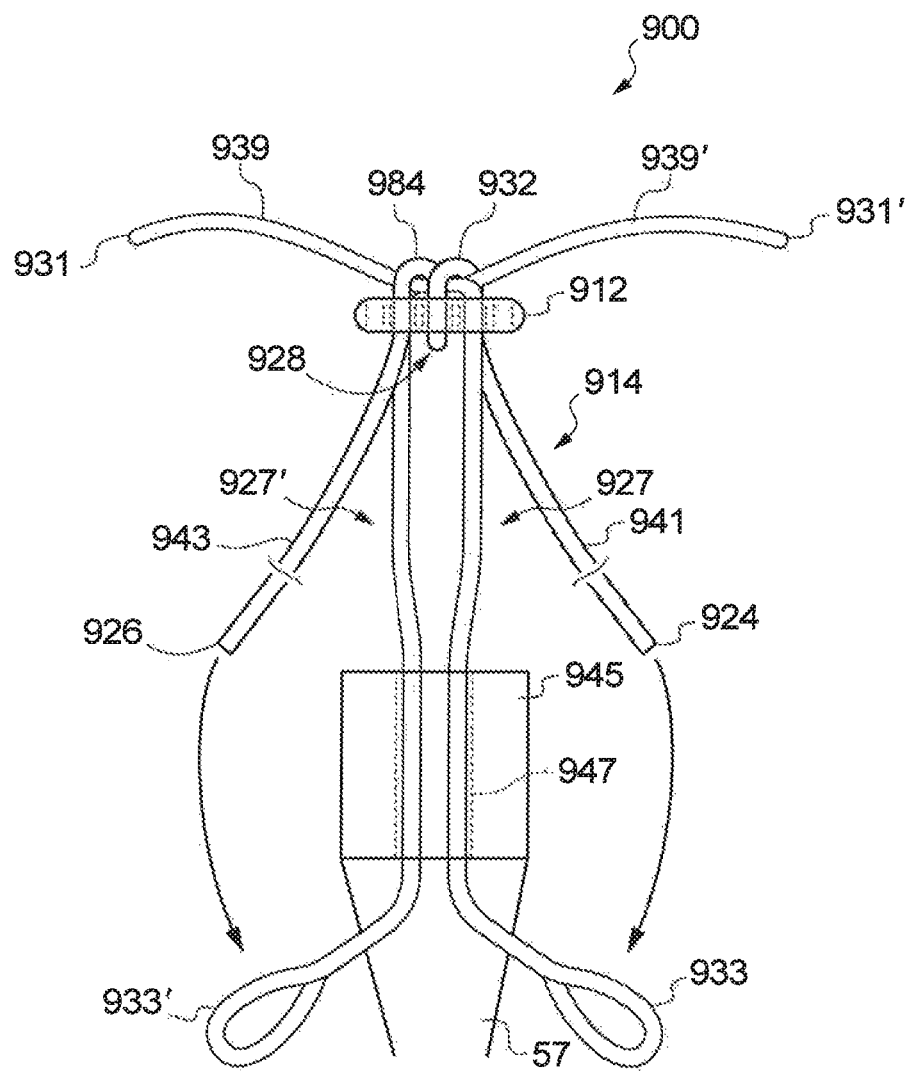
Figure 41:
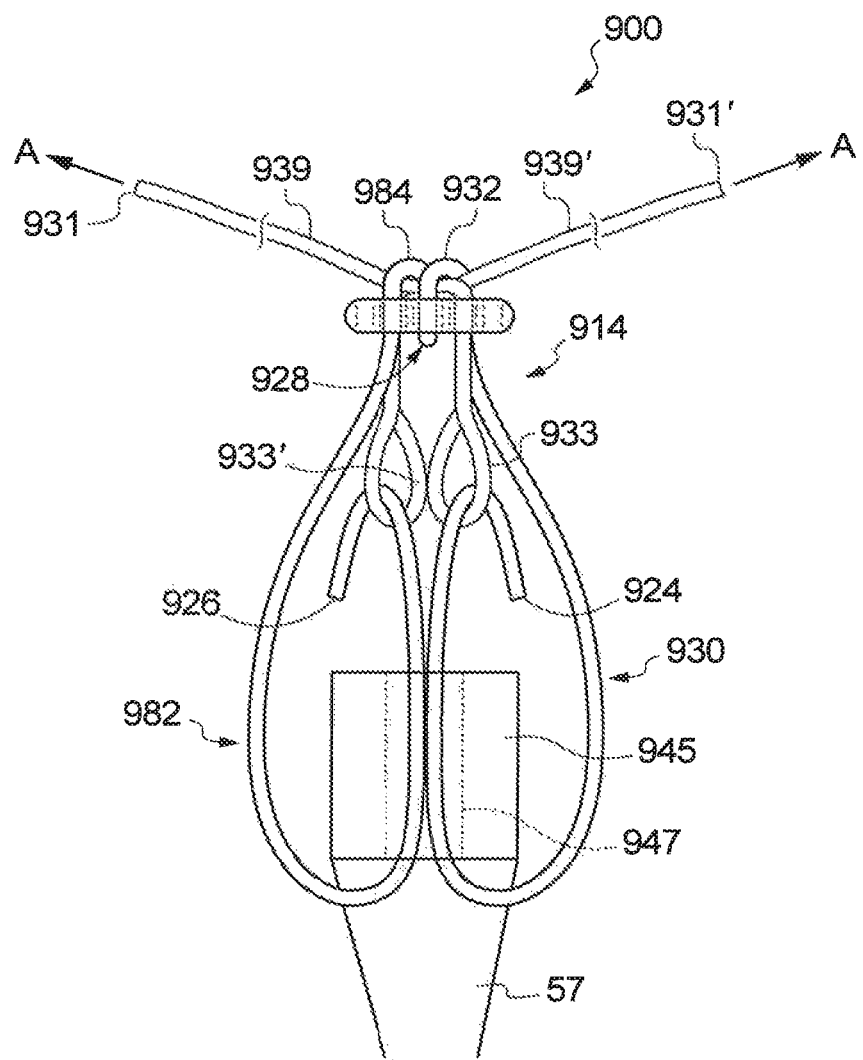
Figure 42:
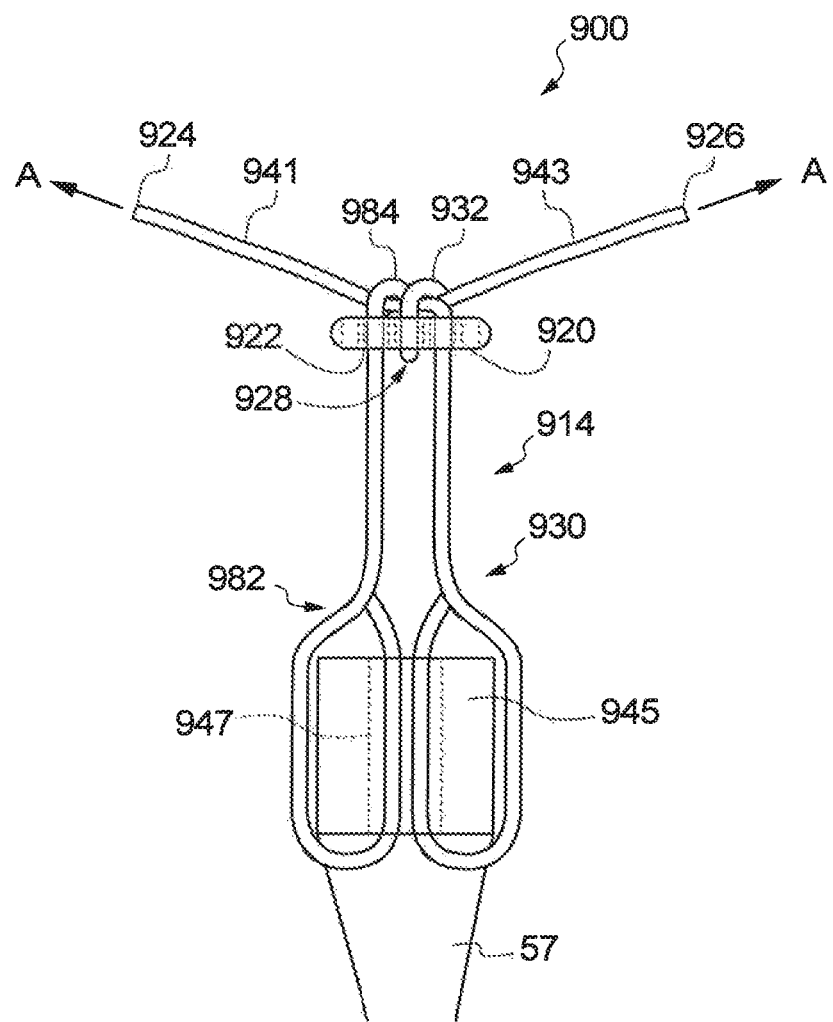

FIG. 39 a front view of a variation on the implant construction device shown in FIG. 32, shown in an assembled state; and FIGS. 40 to 42 are front views of the implant construction device shown in FIG. 32 showing steps in a procedure to form an implant assembly using the implant construction device, involving the coupling of a plug to the device.

Figure 1:
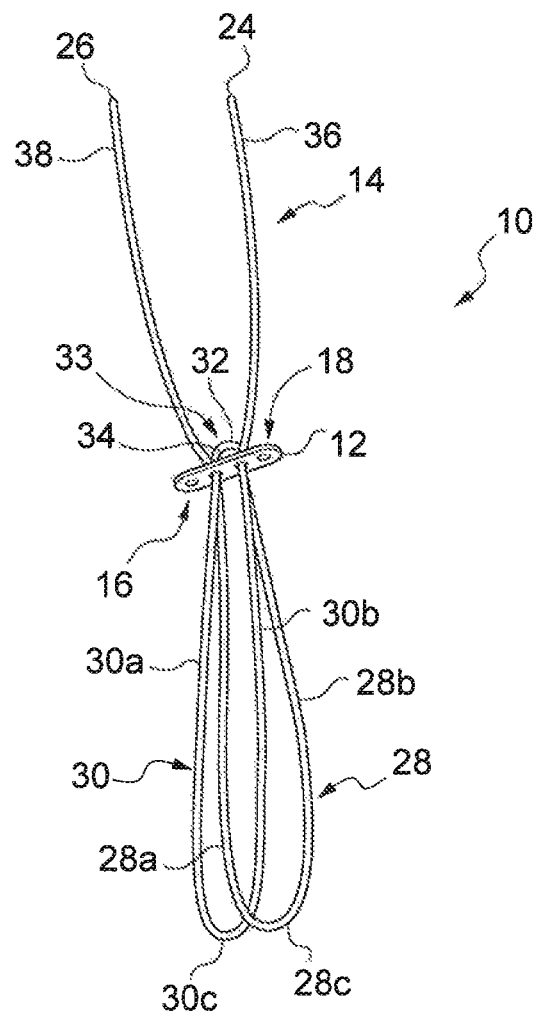
FIG. 1 is a front view of an implant assembly in accordance with an embodiment of the present invention, shown in an assembled state.
Figure 2:
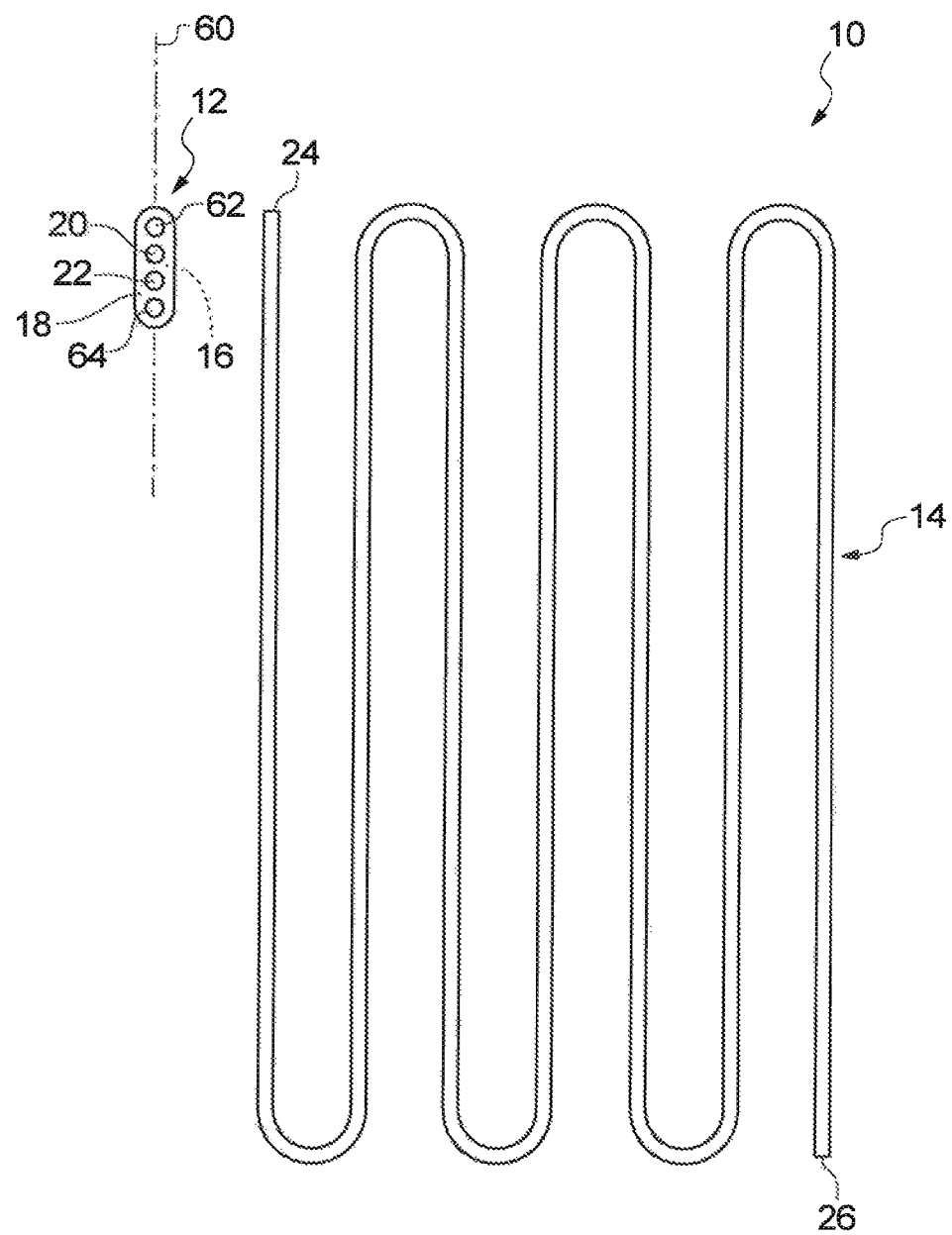
FIG. 2 is a front view of the implant assembly of FIG. 1, shown in a disassembled state.

Turning firstly to FIG. 1, there is shown a front view of an implant assembly in accordance with an embodiment of the present invention, shown in an assembled state, the implant assembly indicated generally by reference numeral 10. The implant assembly 10 is also shown in a disassembled state in the front view of FIG. 2. As will be described below, the implant assembly 10 has a use in tissue repair, which may involve: using the implant assembly to locate an implant in a tunnel in a bone in the human or animal body, the implant replicating at least part of the function of natural tissue such as a damaged ligament or tendon; and/or use of the implant assembly itself to form an implant located in a tunnel in a bone to replicate the function of such damaged tissue.

The implant assembly 10 has an adjustable length, and generally comprises a fixation device 12 and a flexible elongate element 14 secured to the fixation device. The fixation device 12 comprises a bone facing surface 16, an outer surface 18 opposite the bone facing surface, a first aperture 20 extending through the fixation device from the outer surface to the bone facing surface, and a second aperture 22 extending through the fixation device from the outer surface to the bone facing surface. The flexible elongate element 14 has a first free end 24 and a second free end 26.

The flexible elongate element 14 passes through the apertures 20 and 22 of the fixation device 12 to form two bone-side loops in the form of support loops 28 and 30, a fixation loop 32 and an adjustable knot arrangement in the form of an overhand knot arrangement 33, which comprises an adjustable knot in the form of an overhand knot 34. The two support loops 28 and 30 each extend from one of the apertures 20, 22 at the bone facing surface 16 of the fixation device 12 to the other one of the apertures at the bone facing surface. In use, and as will be described below, the support loops 28 and 30 are located within a bone tunnel. The fixation loop 32 extends from one of the apertures 20 and 22 at the outer surface 18 of the fixation device 10 to the other one of the apertures at the outer surface of the fixation device. The overhand knot 34 is positionable on the outer surface 18 of the fixation device 10, a first leg 36 of the overhand knot arrangement 33 extending from the knot 34 to the first free end 24 of the elongate element, and a second leg 38 of the overhand knot arrangement 33 extending from the knot 34 to the second free end 26 of the elongate element.

In the illustrated embodiment, and as discussed above, the support loops 28 and 30 each extend from one of the apertures 20, 22 at the bone facing surface 16 of the fixation device 12 to the other one of the apertures at the bone facing surface. However, and as will be discussed in more detail below, one or more support loop can be provided which extends from a same aperture at the bone face surface of the fixation device. Furthermore, fixation devices may be employed which comprise more than two apertures, and the support loops that are formed may extend between any desirable aperture or apertures at the bone facing surface.

The overhand knot arrangement 33 is securable to the fixation device 12 by the fixation loop 32, which passes over the knot 34 (and optionally over one or both of the first and second legs 36, 38) to clamp the knot arrangement 33 when the support loops 28, 30 are tensioned relative to the fixation device. The flexible elongate element 14 is passed through the apertures 20 and 22 of the fixation device 12 to form the support loops 28 and 30, the fixation loop 32, and the overhand knot 34 in such a way that a length of each of the support loops can easily be adjusted. The ability to easily adjust the lengths of the support loops 28 and 30 provides greater flexibility during a surgical tissue repair procedure, in comparison to prior techniques and assemblies, for example to account for anatomical differences from patient-to-patient, and deviations from a surgical plan which might involve the bone tunnel opening in a different location on the bone surface than had originally been intended.

Figure 3:
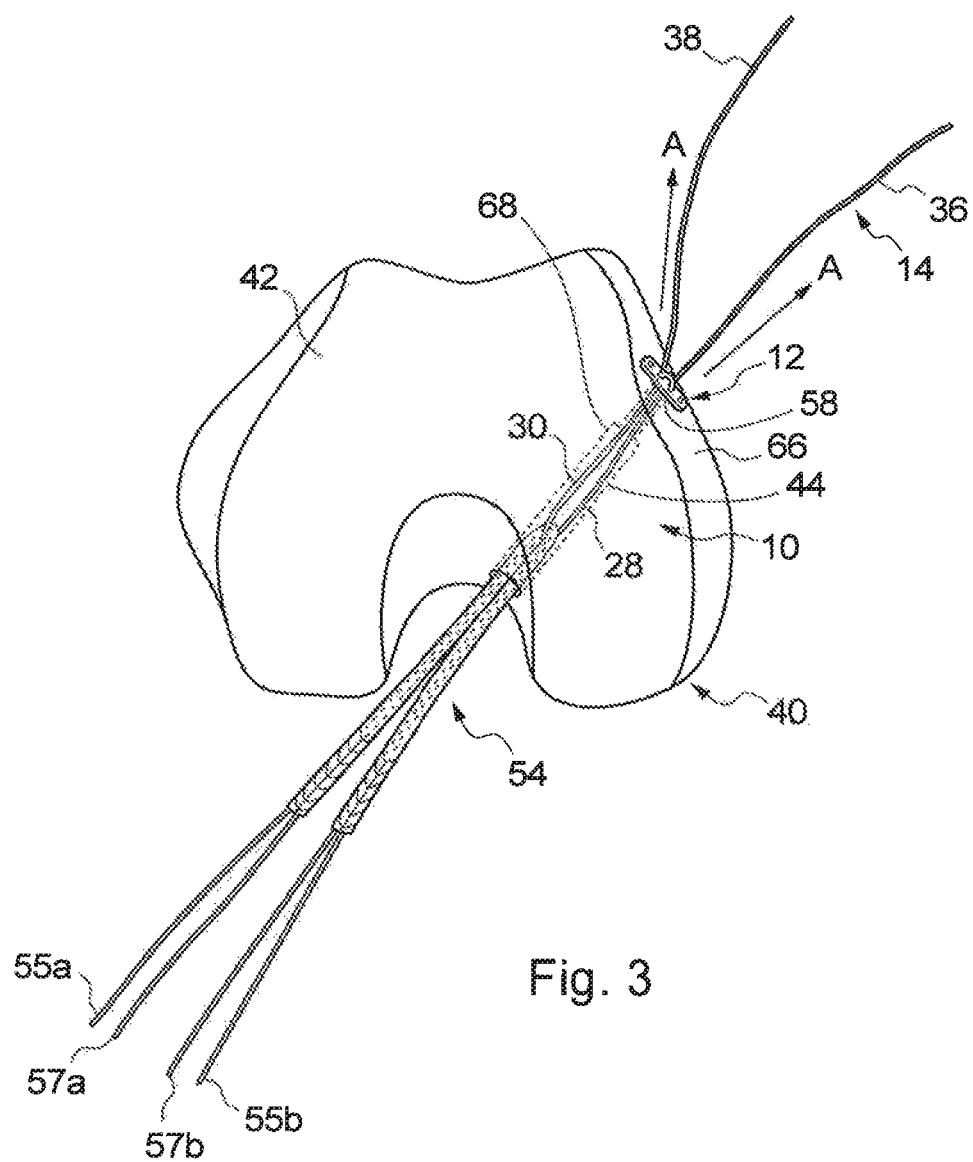
FIG. 3 is a schematic front view of a distal end portion of a femur of a patient, which forms part of a knee joint, showing the implant fixation assembly of FIG. 1 located in a femoral tunnel portion of a bone tunnel, and illustrating a step in a method of tissue repair employing the implant fixation assembly.
Figure 4:
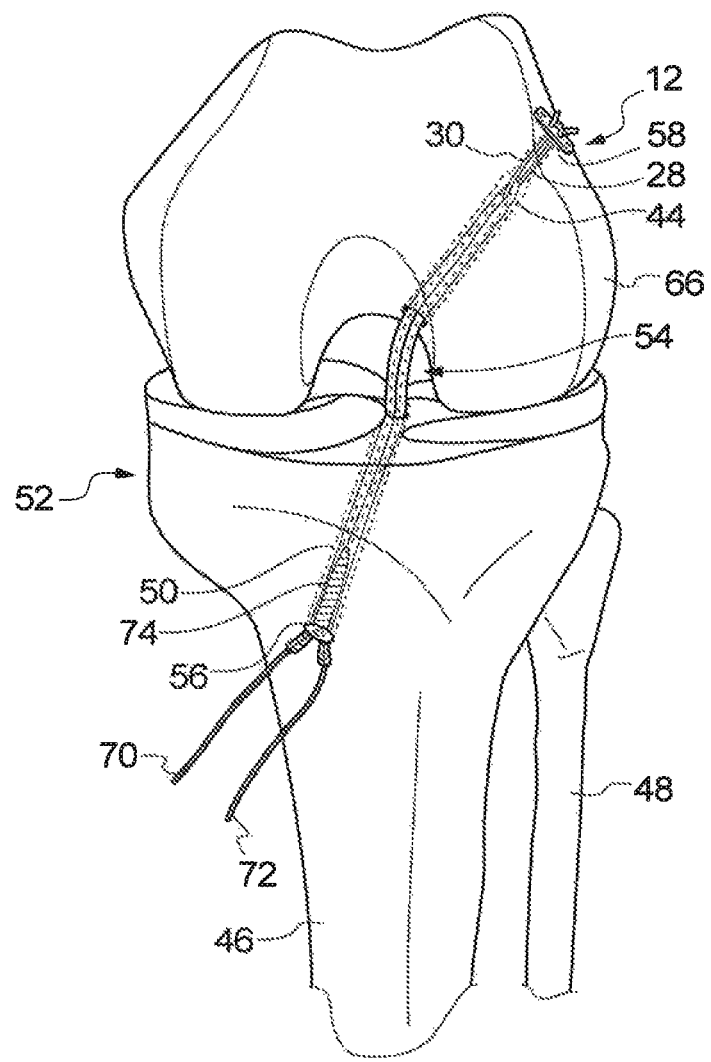
FIG. 4 is a view which is similar to FIG. 3, but which also shows a tibia and fibula of the patient and a tibial tunnel portion of the bone tunnel.

In the embodiment illustrated in FIG. 1, the implant assembly 10 takes the form of an implant fixation assembly which is used to locate an implant within a tunnel in a bone of a boney joint, and to secure or fix the implant within the tunnel. This is illustrated in FIGS. 3 and 4, in the context of a procedure to repair a damaged ACL in a human patient, in which the ACL has suffered a total rupture and is to be replaced with a synthetic implant. FIG. 3 is a schematic front view of a distal end portion 40 of a femur 42 of a patient, which forms part of a knee joint, showing the implant fixation assembly 10 of FIG. 1 located in a femoral tunnel portion 44 of a bone tunnel, and illustrating a step in a method of tissue repair employing the implant fixation assembly. FIG. 4 is a view which is similar to FIG. 3, but which also shows the tibia 46 and fibula 48 of the patient. A tibial tunnel portion 50 is formed which extends through a proximal portion 52 of the tibia 46, and which together with the femoral tunnel portion 44, forms the complete bone tunnel. The tunnel portions 44 and 50 are formed employing techniques which are well known in the field of the invention.

An implant in the form of a double hamstring graft 54 is shown coupled to the implant fixation assembly 10. Sutures 55a/b and 57a/b are whip-stitched to ends of the hamstring tendons, and used to manipulate and tension the hamstring graft 54. The implant 54 is coupled to the implant fixation assembly 10 by passing it through the two support loops 28 and 30, so as to indirectly couple the implant to the fixation device 12. In an alternative, a synthetic implant can be coupled to the implant fixation assembly 10. Many different synthetic implants are available and suitable for use in an ACL repair. One suitable implant is a fabric implant, formed of a woven material having warp fibres (not shown) extending along a length direction of the implant and weft fibres (not shown) extending transverse to the warp fibres. The warp fibres resist extension along a longitudinal axis of the implant, whilst the woven structure facilitates tissue ingrowth into apertures between the warp and weft fibres.

The fixation device 12 takes the form of an elongate button, and may be an Endobutton™ A suitable elongate button is disclosed in the applicant's International Patent Publication no. WO-2016/063019, the disclosure of which is incorporated herein by this reference. In the illustrated method, a tibial insertion technique is used to insert the implant 54 into the bone tunnel, through a tibial opening 56 of the tunnel portion 50. However, a femoral insertion technique may be employed, in which the implant is inserted through a femoral opening 58 of the tunnel portion 44.

In the illustrated embodiment, the flexible elongate element 14 takes the form of a suture, and is suitably a multifilament element, in particular a tubular braid, which can enhance tissue ingrowth. Alternatively, the filaments forming the element 14 can be twisted together, the element typically taking the form of a cord.

As is well known, the elongate button 12 is inserted into the tibial opening 56 oriented so that a longitudinal axis 60 (FIG. 2) of the button is generally aligned with an axis (not shown) of the tibial tunnel portion 50. A pulling suture (not shown) is coupled to a third aperture 62 of the button 12, to translate the button (and the trailing implant 54) along the tibial tunnel portion 50 and into the femoral tunnel portion 44. The button 12 is brought to a position where it is exposed from the femoral opening 58, and is then flipped so that it overlies the opening. Flipping of the button 12 is achieved using a flipping suture (not shown) coupled to a fourth aperture 64 of the button, which is at a trailing end during passage along the bone tunnel. FIG. 3 shows the button 12 after it has been flipped and tension applied to the implant 54 to bring the bone facing surface 16 of the button into contact with a surface 66 of the femur 42 surrounding the femoral opening 58. The legs 36 and 38 are then trimmed to a desired length, optionally following formation of a securing knot over the top of the fixation loop 32 and overhand knot 34.

As will be appreciated by those skilled in the art, anatomical differences from patient-to-patient, and deviations from a surgical plan which might involve the bone tunnel portions 44 and 50 opening in a different location on the bone surfaces than had originally been intended, can complicate the surgical procedure. For example, formation of the femoral tunnel portion 44 in an unplanned location in the femur 42 may result in the tunnel portion having a shorter length than was originally intended. This is illustrated in FIGS. 3 and 4. In this scenario, the support loops 28 and 30 are too long, with the result that the implant 54 is positioned too far down the bone tunnel, and away from a stepped diameter section 68 shaped to receive the implant.

The implant fixation assembly 10 of the present invention provides an ability to remedy this during the surgical procedure, by adjusting the lengths of the support loops 28 and 30 which couple the implant 54 to the button 12. This enables a distance between the button 12 and the implant 54 suspended from the button to be adjusted, to properly seat the implant in the tunnel adjacent the stepped section 68, as shown in FIG. 4. Shortening of the support loops 28 and 30 is achieved by pulling on the legs 36 and 38 which extend from the knot 34, as shown by the arrows A in FIG. 3. The implant 54 can then be tensioned, by pulling on ends 70 and 72 of the implant, and secured in the tunnel under tension using a locking component such as an interference screw 74. The protruding portions of the implant 54 can then be trimmed to length as required.

The implant assembly 10, and its method of manufacture, will now be described in more detail, with reference also to FIGS. 5 to 11, which are drawings showing sequential steps in the method.

The element 14 is arranged so that it follows a path which extends continuously through the first and second apertures 20 and 22 in the button 12 to form the support loops 28 and 30, the fixation loop 32 and the overhand knot arrangement 33. In particular, the element 14 is arranged so that it successively forms a first one of the support loops 28, the fixation loop 32, a second one of the support loops 30 and the overhand knot 34.

The overhand knot 34, and the fixation loop 32, together form a self-locking knot assembly. The self-locking knot assembly self-locks under load, which is a tensile load imparted on the support loops 28 and 30 during use, when the implant 54 is suspended in the bone tunnel from the support loops. A length of the support loops 28 and 30 is therefore automatically locked when the support loops are placed under tension. This is achieved because tensioning the support loops 28 and 30 both brings the overhand knot 34 on to the outer surface 18 of the button 12, and causes the fixation loop 32 to lock the knot 34 and/or either or both of the legs 36 and 38 that it passes over.

The support loops 28 and 30 are adjustable in length by manipulation of the fixation loop 32 and the overhand knot 34. In particular, adjustment of the length of the support loops 28 and 30 can be achieved by releasing tension applied to the support loops, releasing the fixation loop 32 from the overhand knot arrangement 33, adjusting a location of the knot 34 along a length of the element 14, and then re-tensioning the support loops 28 and 30. Adjusting the location of the knot 34 along the length of the element 14 increases or decreases lengths of each of the first and second legs 36 and 38, thereby providing less material in the support loops 28 and 30 (to decrease their length), or more material in the support loops (to increase their length), respectively.

The overhand knot 34 is positioned between the outer surface 18 of the button 12 and the fixation loop 32. In this way, tension applied to the support loops 28 and 30 draws the knot 34 towards the outer surface 18 and the fixation loop 32 towards the knot, to clamp the knot arrangement 33. The knot arrangement 33 is held in position by a combination of tension in the support loop 28/30 extending from the knot on the bone facing surface 16 of the button 12, and tension in the other one of the support loops 28/30 extending from the fixation loop 32.

The first and second apertures 20 and 22 of the button 10 each have an opening on or in the bone facing surface 16 of the button 12, and an opening on or in the outer surface 18. The support loops 28 and 30 each extend between openings of the apertures 20, 22 which are on or in the bone facing surface 16, whilst the fixation loop 32 extends between openings which are on or in the outer surface 18.

The support loops 28/30 each have a respective first loop portion 28a/30a (FIG. 1) extending from one of the button apertures 20 and 22 to an apex 28c/30c of the loop, and a respective second loop portion 28b/30b extending from the other one of the apertures to a respective apex 28c/30c of the loop. The fixation loop 32 has a first loop portion 32a (FIG. 6) extending from one of the button apertures 20 and 22 to an apex 32c of the loop, and a second loop portion 32b extending from the other one of the apertures to the apex of the loop. The overhand knot 34 has a first knot loop portion 34a (FIG. 10) extending from one side of the knot to one of the button apertures 20 and 22, and a second knot portion 34b extending from the other side of the knot to the other one of the apertures. The first loop portion 28a of the support loop 28 extends from the first side 34a of the knot 34, and the second loop portion 28b of the support loop 28 extends from the second loop portion 32b of the fixation loop 32. The first loop portion 30a of the support loop 30 extends from the first loop portion 32a of the fixation loop 32, and the second loop portion 30b of support loop 30 extends from the second side 34b of the knot 34. In this way, tensioning of the support loops 28 and 30 is effective both to bring the knot 34 on to the button outer surface 18, and to cause the fixation loop 32 to clamp the overhand knot arrangement 33.

Figure 8:
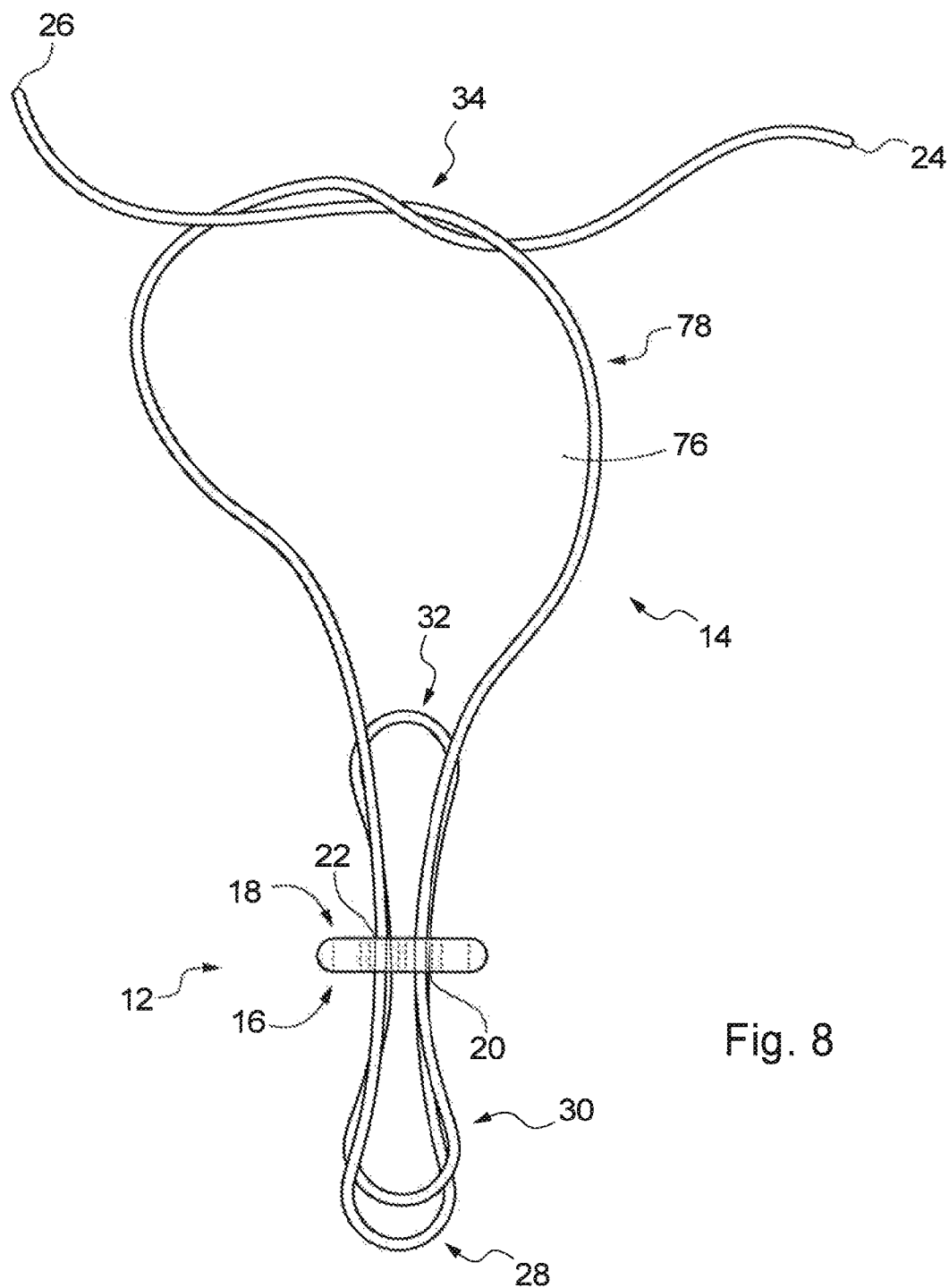

Formation of the overhand knot is shown in FIG. 8, and involves taking a portion of the element 14 having the first free end 24, and a portion of the element 14 having the second free end 26, crossing one of said portions behind the other to form an eye 76, and then directing one of said portions around the other portion and through the eye to form a knot loop 78. In the context of the present invention, the loop 78 that is formed is bound by the outer surface 18 of the button 10.

The method of manufacturing the implant assembly 10 involves the following steps.

Figure 5:
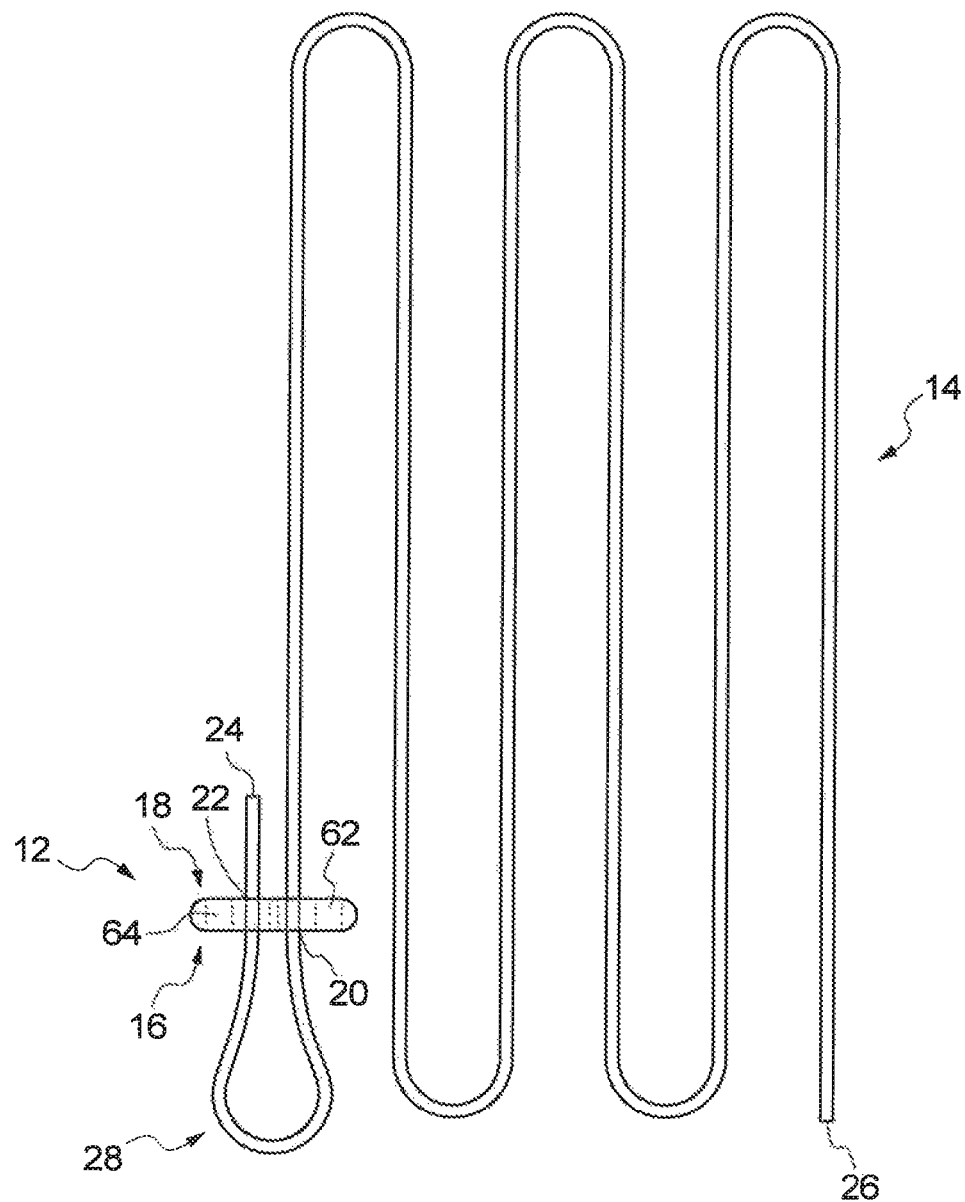
FIGS. 5 to 10 are front views of the implant assembly of FIG. 1, showing sequential steps in a method of manufacturing the implant assembly.

In a first step which is shown in FIG. 5, the element 14 is directed through the first aperture 20 of the button 12, and through the second aperture 22, so that a portion of the element including the first free end 24 and a portion of the element including the second free end 26 both extend from the button apertures 20 and 22 on the outer surface 18 side of the button. This forms the first support loop 28, which is on the bone facing surface 16 side of the button.

Figure 6:
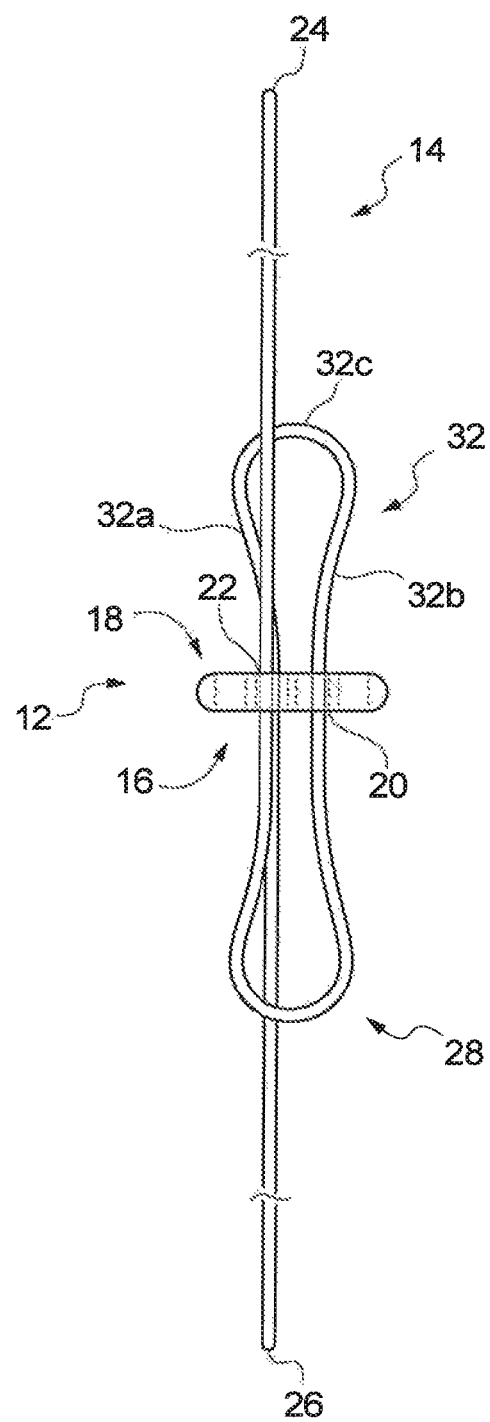

In a second step which is shown in FIG. 6, the portion of the element 14 which extends from the first aperture 20 on the outer surface 18 side of the button 12 is directed through the second aperture 22, so that the portion extends from the second aperture on the bone facing surface 16 side of the button. This forms the fixation loop 32, which is on the outer surface side 18 of the button 12.

Figure 7:
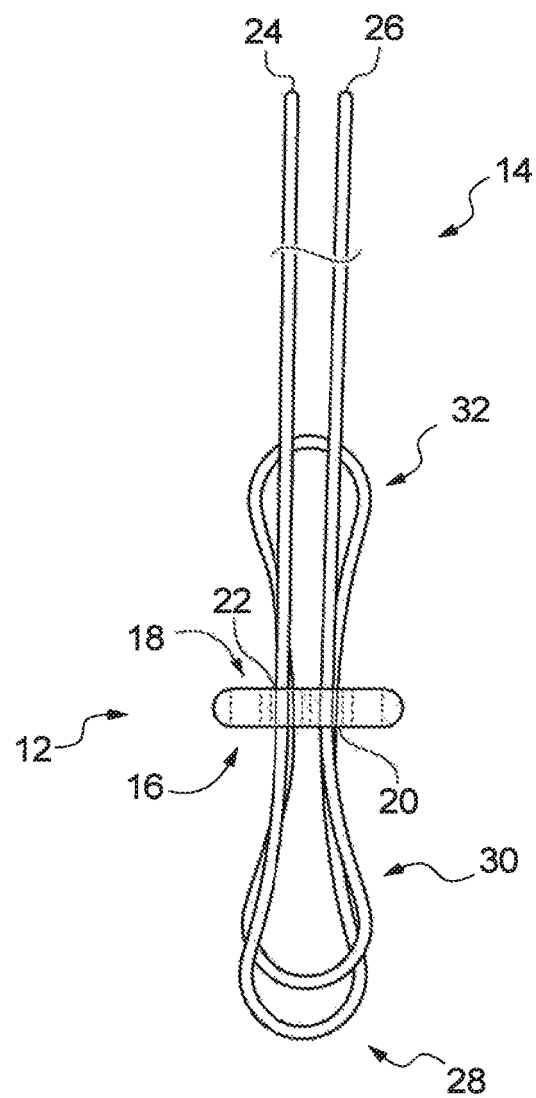

In a third step which is shown in FIG. 7, the portion of the element 14 which extends from the second aperture 22 on the bone facing surface 16 side of the button 12 is directed through the first aperture 20, so that the portions of the element including the first 24 and second 26 free ends both extend from the apertures on the outer surface 18 side of the button. This forms the second support loop 30, which is on the bone facing surface 16 side of the button. In the method illustrated in FIG. 7, the portions of the element 14 including the first 24 and second 26 free ends are both disposed on one side of the fixation loop 32. However, and as will be described below, the portions of the element 14 including the first 24 and second 26 free ends may be directed through the button 12 in such a way that one of said portions is disposed on one side of the fixation loop 32, and the other one of the portions on the other side of the fixation loop.

Figure 9:
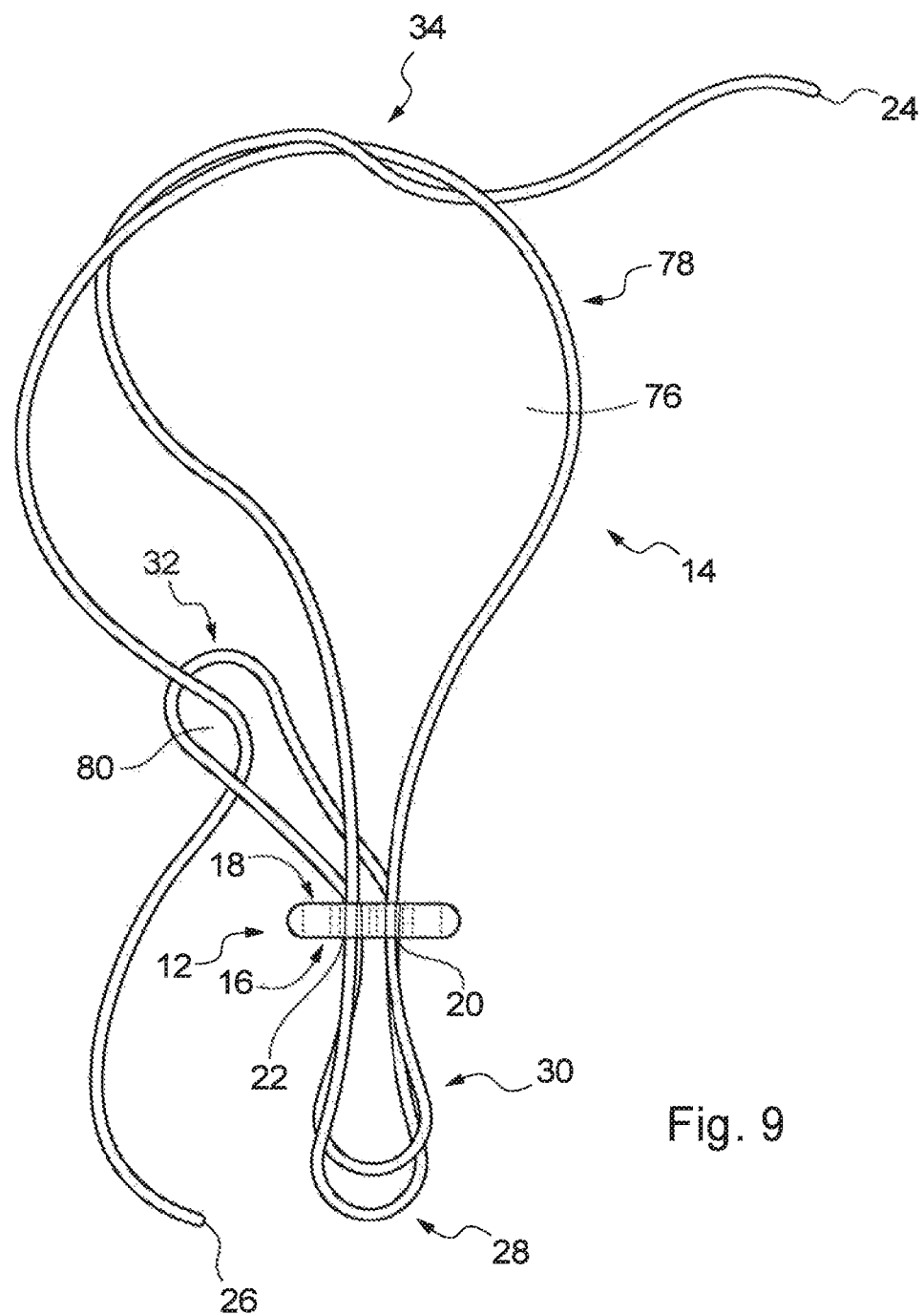
Figure 10:
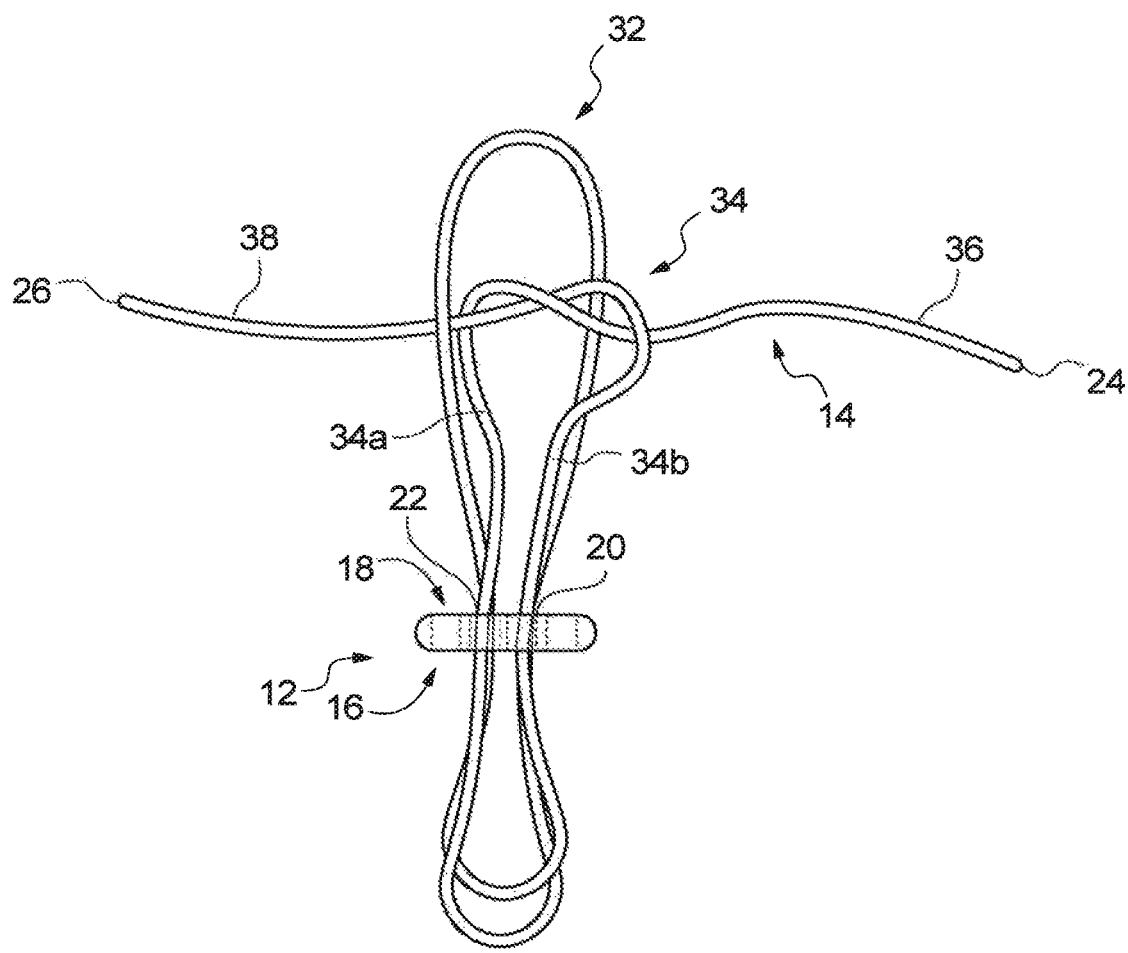

In a fourth step which is shown in FIG. 8, the portions of the element 14 including the first 24 and second 26 free ends are manipulated to form the overhand knot 34, in the fashion described above. The knot 34 is then manipulated so that it is positioned between the outer surface 18 of the button 12 and the fixation loop 32. This is achieved by directing one of the element 14 portions (suitably the portion including the second free end 26) through an eye 80 of the fixation loop 32, as shown in FIG. 9, and then pulling on both of the portions including the free ends 24 and 26 to bring the knot 34 towards the outer surface 18 of the button 12, as shown in FIG. 10.

Figure 11:
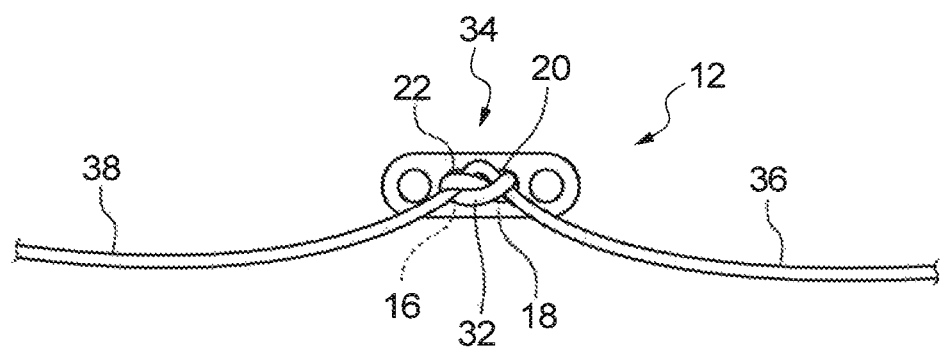
FIG. 11 is a top view of the implant assembly of FIG. 1, showing a final step in the method of manufacture of the implant assembly.

In a fifth step which is shown in the top view of FIG. 11, the fixation loop 32 is manipulated to clamp the overhand knot arrangement 33 (in particular the knot 34) to the button 12 and thereby secure the knot arrangement 33 (in particular the knot 34) and so the element 14 to the button. This is achieved by applying tension to the support loops 28 and 30. The overhand knot 34 and the fixation loop 32 together effectively form a self-locking knot assembly, which self-locks under a tensile load imparted on the support loops 28 and 30. A length of the support loops 28 and 30 is therefore automatically locked or fixed when the support loops are placed under tension. This may be achieved because tensioning the support loops 28 and 30 both brings the overhand knot 34 on to the outer surface 18 of the button, and causes the fixation loop 32 to lock the knot arrangement 33. Adjustment of the length of the support loops 28 and 30 involves releasing tension on the support loops, manipulating the fixation loop to release it from the outer surface 18 of the button 10, and then adjusting the overhand knot 34 by pulling on the legs 36 and 38 (to shorten the support loops) or by feeding material from the legs into the support loops (to lengthen the loops).

Figure 11A:
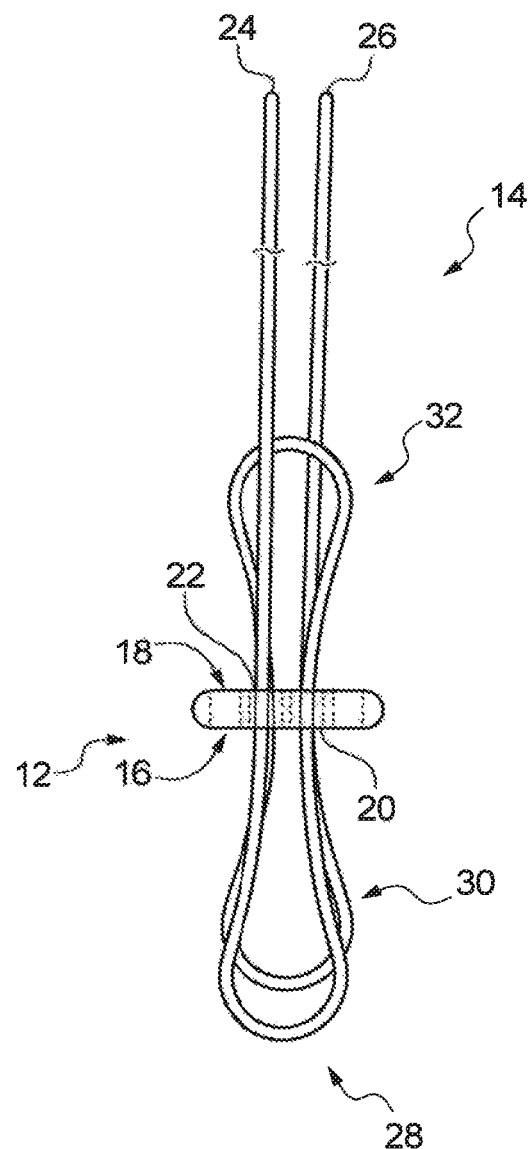
FIGS. 11A and 11B are front views of a variation on the implant assembly of FIG. 1, showing certain sequential steps in its method of manufacture.

Turning now to FIG. 11A, there is shown a variation on the method of manufacturing the implant assembly 10 outlined above. In the variation, the method initially follows the steps outlined in FIGS. 5 and 6. The variation involves passing the portion of the element 14 including the second leg 26 through the first aperture 20 from the bone facing surface 16 side of the button 12 to the outer surface 18 side in such a way that it is disposed on an opposite side of the fixation loop 32 to the portion including the first free end 24. Effectively, these two portions of the element 14 straddle the fixation loop 32, so that the loop is disposed between the portions.

Figure 11B:
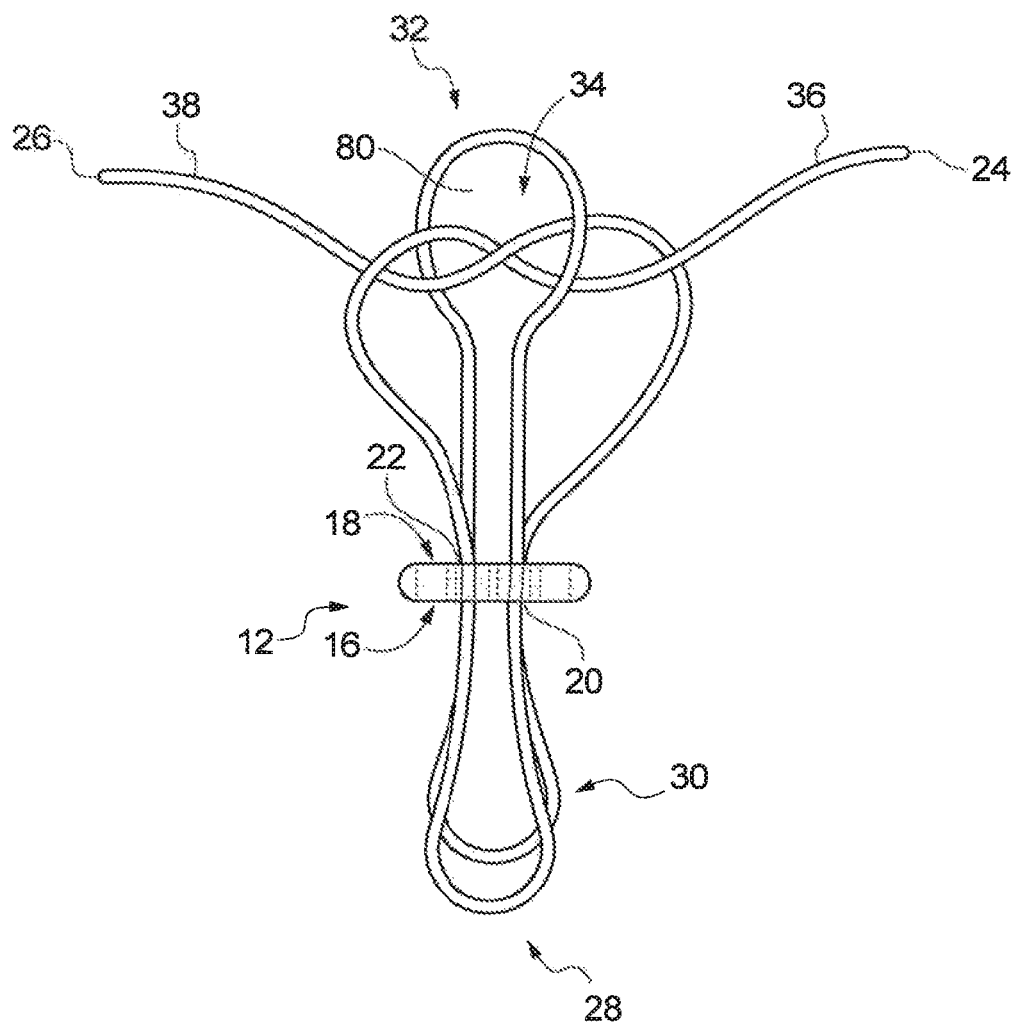

The portions of the element 14 including the first and second free ends 24 and 26 are then passed in generally opposite directions through the eye 80 of the fixation loop 32, and the knot 34 formed as described above. This is shown in FIG. 11B. These steps may be facilitated by lengthening the fixation loop 32, involving feeding element 14 material from the bone facing surface side 16 of the button 12. The knot 34 is then brought towards the outer surface 18 of the button 12, in the same way as shown in FIG. 10, and the fixation loop 32 manipulated to clamp the overhand knot arrangement 33 (in particular the knot 34) to the button, by applying tension to the support loops 28 and 30. This is shown in the enlarged top view of FIG. 11C.

Figure 11C:
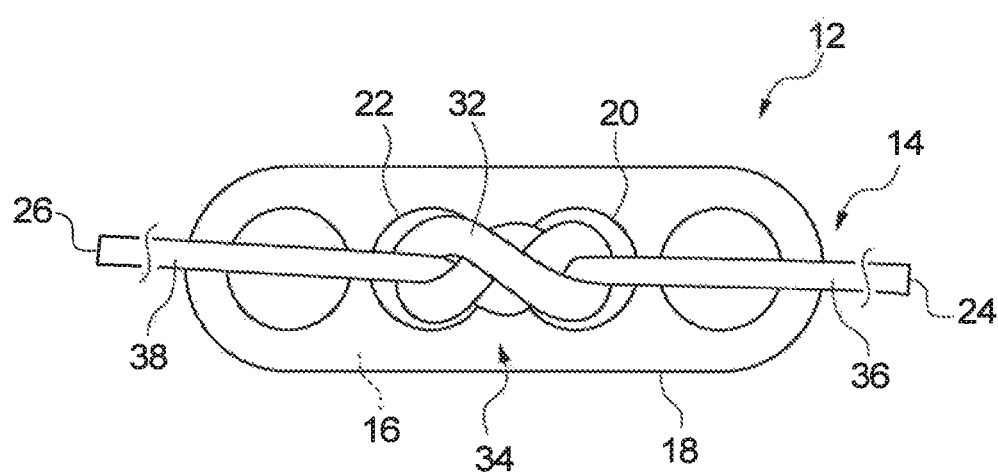
FIG. 11C is an enlarged plan view of a fixation device forming part of the implant assembly shown in FIGS. 11A and 11B, showing the assembly following completion of the manufacturing method.

As can be seen by comparing FIG. 11 with FIG. 11C, the modified method shown in FIGS. 11A to 11C may provide an enhanced clamping effect of the fixation loop 32 on the knot arrangement 33 (in particular on the knot 34), because the fixation loop is routed in such a way that it passes over the knot 34, and securely clamps both parts of the element 14 which form the knot legs 36 and 38. The combination of the knot 34 and the fixation loop 32, may together form what can be known as a 'constrictor knot'.

The variation in the method shown in FIGS. 11A to 11C can apply not only to formation of the implant assembly 10, but to any of the other implant assemblies shown and described in this document.

Figure 11D:
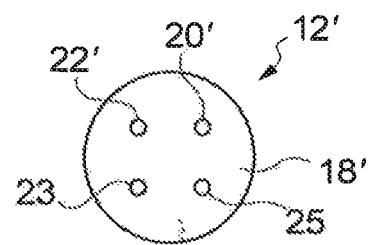
FIG. 11D is a plan view of a fixation device in accordance with another embodiment of the present invention.

Turning now to FIG. 11D, there is shown a plan view of a variation on the fixation device 12 shown in FIGS. 1 to 11, the variation of the fixation device indicated generally by reference numeral 12'. Like components of the fixation device 12' with the device 12 share the same reference numerals, with the addition of the suffix '. In this embodiment, the fixation device 12' again takes the general form of a button, but includes four apertures passing through the button from a bone-facing surface 16' to an outer surface 18', the apertures indicated by reference numerals 20', 22', 23 and 25. The button 12' may have a use in surgical procedures other than ACL repair, for example in an ACJ repair technique, such as those shown and described in WO-2017/013431, the disclosure of which is incorporated herein by this reference.

Figure 11E:
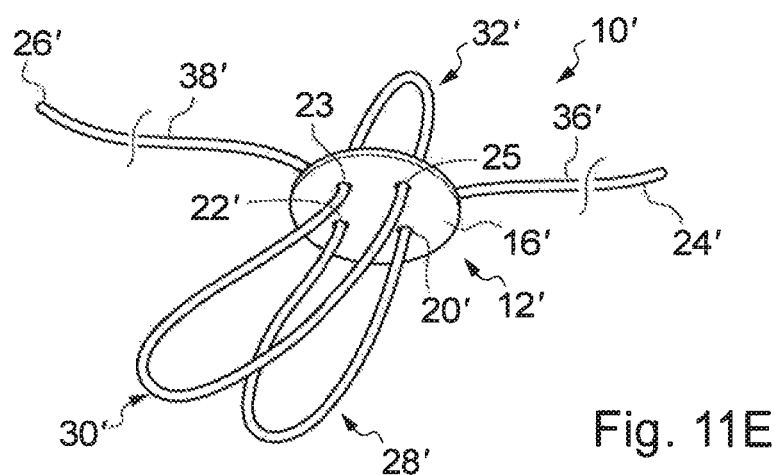
FIGS. 11E and 11F are perspective views, taken from below and from above respectively, showing an implant assembly in accordance with another embodiment of the present invention.
Figure 11F:
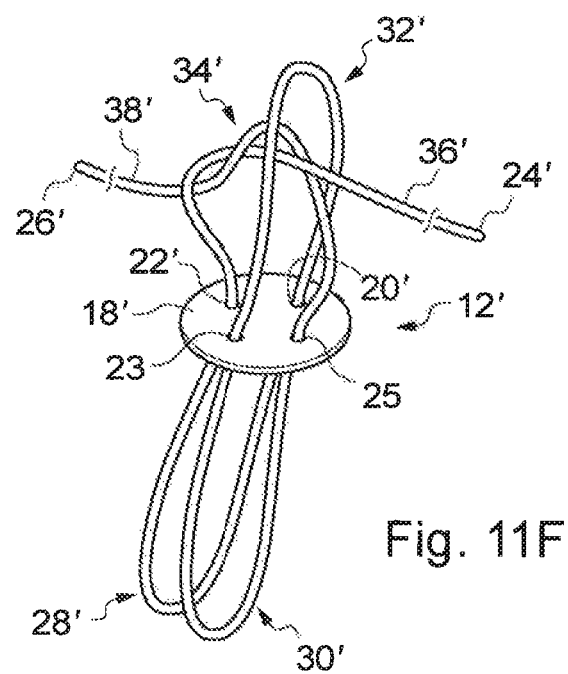

An implant assembly 10' formed employing the button 12' is shown in the bottom perspective view of FIG. 11E, and in the top perspective view of FIG. 11F. Once again, like components of the implant assembly 10' with the implant assembly 10 share the same reference numerals with the addition of the suffix '.

The method of forming the implant assembly 10' is much the same as that shown in FIGS. 1 to 11C (and can in particular includes the variation shown in FIGS. 11A to 11C), save that it involves directing the flexible elongate element 14' through all four of the apertures 20', 22', 23 and 25 in the button 12'. Specifically, and starting from a similar position to that shown in FIG. 5, the method involves taking the first free end 24' of the element 14' and passing it down from the outer surface 18' side of the button 12' through the first aperture 20'. The free end 24' is then passed up from the bone facing surface 16' side through the second aperture 22'. At this time, both of the free ends 24' and 26' reside on the outer surface 18' side. The second free end 26' of the element 14' is then passed across the button and down through the third aperture 23 to the bone facing surface 16' side. The free end 26' is then passed up from the bone facing surface 16' side through the fourth aperture 25. This forms two bone side support loops 28' and 30', as well as a fixation loop 32'. A knot 34' can then be formed in the fashion described above (particularly with reference to FIGS. 11A to 11C), and secured by tensioning the support loops 28' and 30'. It will be understood that similar results can be achieved by directing the free ends 24' and 26' of the element 14' through the apertures of the fixation device 12' in a different order.

The fixation device 12', and the variation in the method shown in FIGS. 11D to 11F can apply not only to formation of the implant assembly 10', but to any of the other implant assemblies shown and described in this document.

Figure 12:
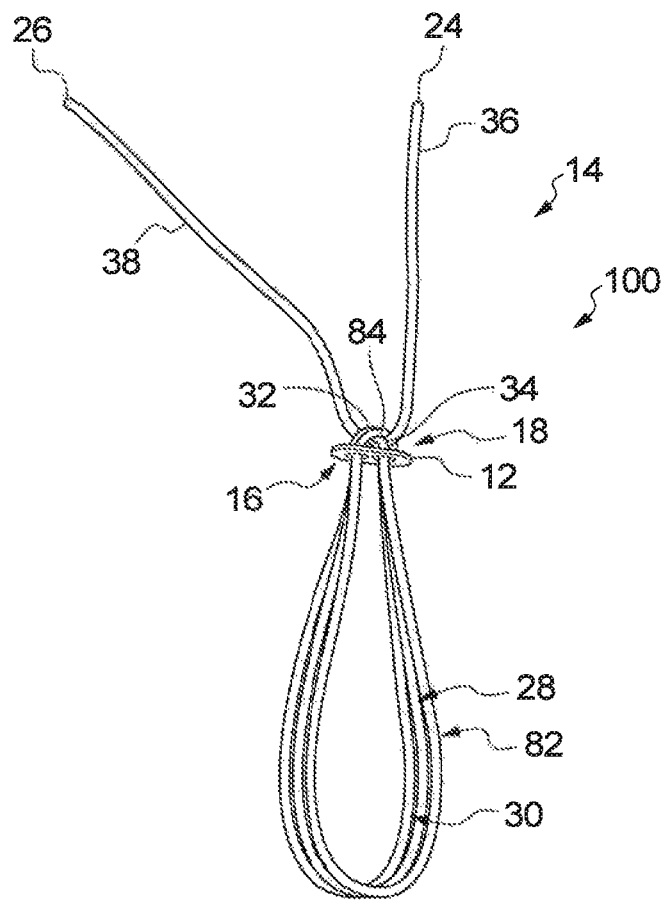
FIG. 12 is a front view of an implant assembly in accordance with another embodiment of the present invention, shown in an assembled state.

Turning now to FIG. 12, there is shown a front view of an implant assembly in accordance with another embodiment of the present invention, shown in an assembled state, the implant assembly indicated generally by reference numeral 100. Like components of the implant assembly 100 with the implant assembly 10 shown in FIGS. 1 to 11 share the same reference numerals. Only the substantive differences between the implant assembly 100 of FIG. 12 and the assembly 10 of FIGS. 1 to 11 will be described in detail.

The implant assembly 100 again takes the form of an implant fixation assembly, for securing an implant such as the implant 54 within a bone tunnel. The implant assembly 100 is of like construction to the assembly 10, and manufactured in a similar fashion, with the exception that the assembly 100 includes a further bone-side loop in the form of a support loop 82 which extends from one of the apertures 20 and 22 at the bone facing surface 16 of the button 12 to the other one of the apertures at the bone facing surface. The assembly 100 therefore comprises first, second and third support loops 28, 30 and 82. This provides additional strength under tension loading during use. In addition, the implant assembly 100 comprises a second fixation loop 84 which extends from one of the apertures 20 and 22 at the outer surface 18 of the button 12 to the other one of the apertures at the outer surface of the button. The second fixation loop 84 also passes over the overhand knot arrangement 33, in particular over the knot 34. The first and second fixation loops 32 and 84 act together to clamp the knot arrangement 33 (in particular the knot 34) to the button when the support loops 28, 30 and 82 are tensioned. This provides additional security against movement and so extension of the support loops 28, 30 and 82.

Figure 13:
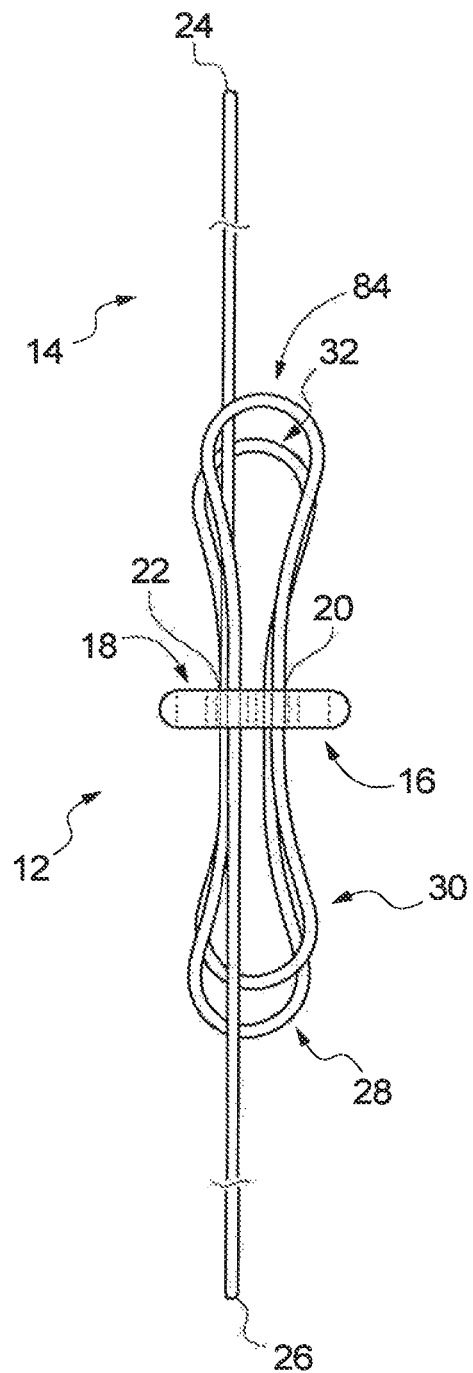
FIGS. 13 to 15 are front views of the implant assembly of FIG. 12, showing additional steps in the method which is employed to manufacture the implant assembly, beyond those shown in FIGS. 5 to 10.
Figure 14:
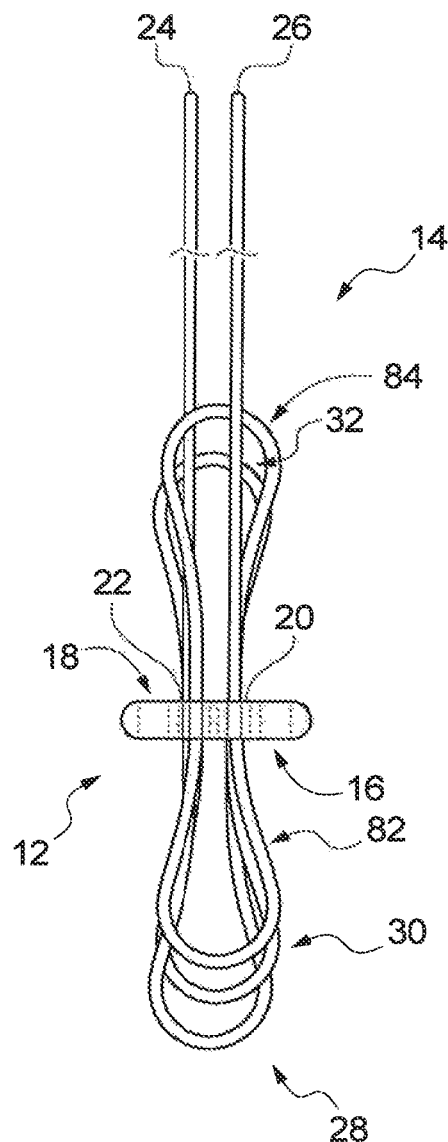

Manufacture of the implant assembly 100 is achieved by carrying out the same steps as are shown in FIGS. 5 to 7 discussed above, but then carrying out additional steps which are shown in FIGS. 13 and 14, prior to formation of the overhand knot 34.

Starting from FIG. 7, in which the portions of the element 14 including the first 24 and second 26 free ends both extend from the apertures 20 and 22 on the outer surface 18 side of the button 12, the method involves directing the portion of the element 14 which extends from the first aperture 20 on the outer surface 18 side of the button 12 back through the second aperture 22, so that said portion extends from the second aperture on the bone facing surface 16 side of the button. This step is shown in FIG. 13, and forms the second fixation loop 84.

The portion of the element 14 extending from the second aperture 22 of the button 12 on the bone facing surface 16 side is then directed through the first aperture 20, so that the portions of the element including the first and second free ends 24 and 26 again both extend from the apertures 20, 22 on the outer surface 18 side of the button. This is shown in FIG. 14, and forms the third support loop 82.

Figure 15:
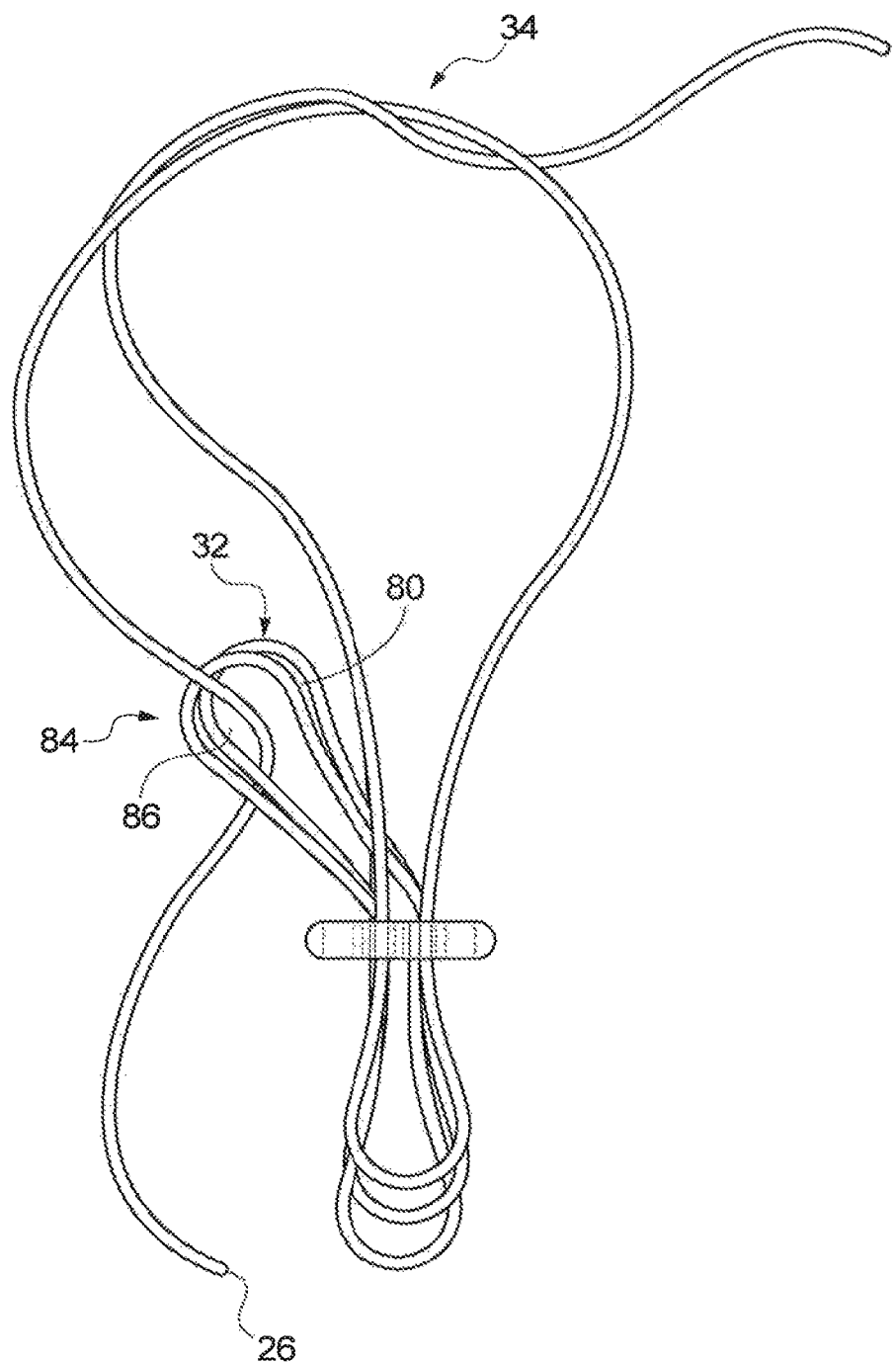
Figure 16:
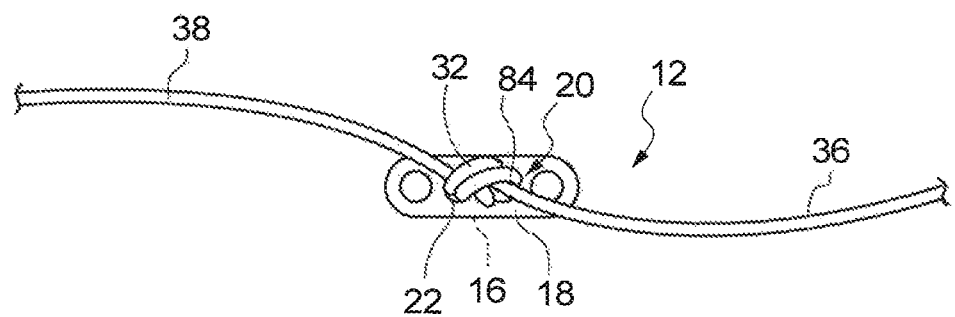
FIG. 16 is a top view of the implant assembly of FIG. 12, showing a final step in the method of manufacture of the implant assembly.

Completion of the implant assembly 100 then follows the steps shown in FIGS. 9 to 11 described above, save that the element 14 portion including the second free end 26 is directed through the eye 80 of the first fixation loop 32 and an eye 86 of the second fixation loop 84, as shown in FIG. 15. The element portions including the free ends 24 and 26 are then manipulated in a similar fashion to bring the knot 34 towards the outer surface 18 of the button 12 and the three support loops 28, 30 and 82 tensioned to lock a length of the support loops. In this way, both of the fixation loops 32 and 84 clamp the knot overhand arrangement 33 (in particular the knot 34) to the button, as shown in the top view of FIG. 16, thereby securing the element 14 to the button 12.

Figure 17:
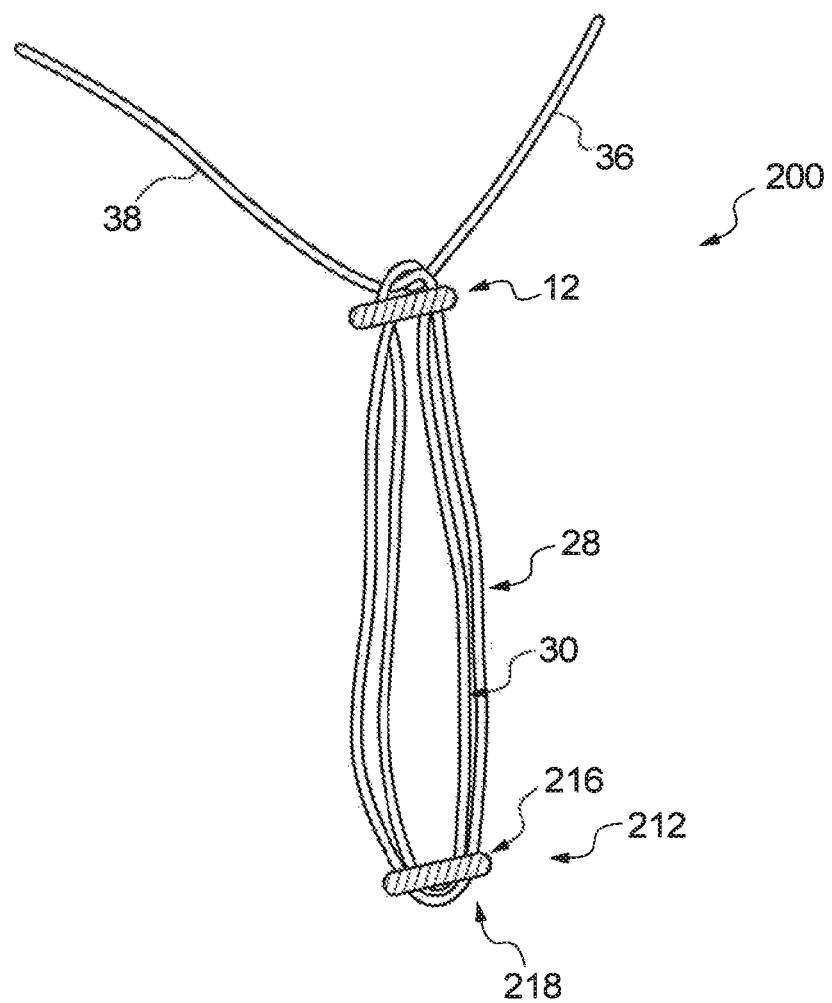
FIG. 17 is a front view of an implant assembly in accordance with another embodiment of the present invention, shown in an assembled state.

Turning now to FIG. 17, there is shown a front view of an implant assembly in accordance with another embodiment of the present invention, shown in an assembled state, the implant assembly indicated generally by reference numeral 200. Like components of the implant assembly 200 with the implant assembly 10 shown in FIGS. 1 to 11 share the same reference numerals. Only the substantive differences between the implant assembly 200 of FIG. 17 and the assembly 10 of FIGS. 1 to 11 will be described in detail.

The implant assembly 200 is essentially of the same construction as the implant assembly 10, save that it includes a second fixation device 212 which is also in the form of an elongate button comprising a bone facing surface 216, an outer surface 218 opposite the bone facing surface, and first and second apertures (not shown) extending through the button.

Figure 18:
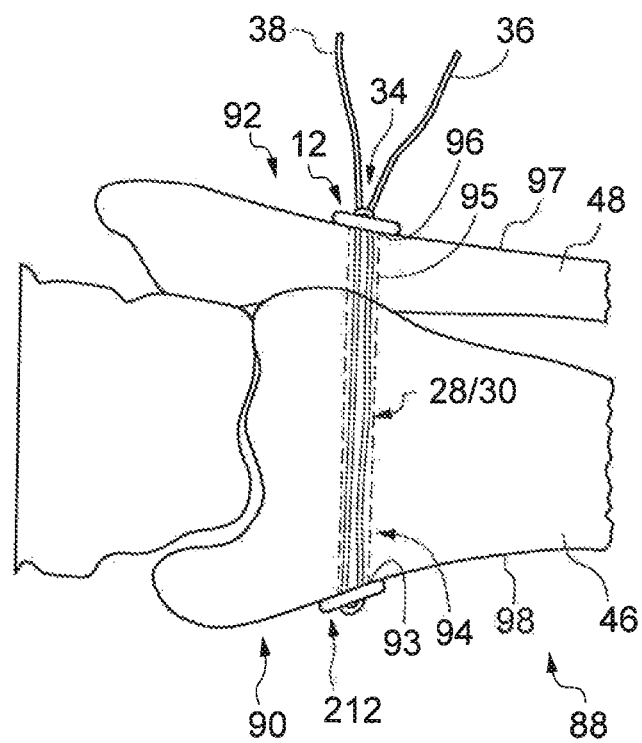
FIG. 18 is a schematic front view a syndesmotic ankle joint between a distal portion of a tibia and a distal portion of a fibula, showing the implant assembly of FIG. 17 located in a bone tunnel formed in the joint, and illustrating a step in a method of tissue repair employing the implant assembly.

The first and second buttons 12 and 212 can be used in cooperation, for example in a procedure to restore bones of a syndesmotic joint to their proper position. This is illustrated in FIG. 18, in the context of a syndesmotic ankle joint 88 between a distal portion 90 of the tibia 46 and a distal portion 92 of the fibula 48. As is well known in the field of the invention, a dislocation of the joint 88 can cause tendon damage (including to the IOL, AITFL, PITFL and/or TTFL) in which the bones 46 and 48 become distracted from their proper positions.

In a method of tissue repair using the implant assembly 200, the first button 12 is directed into an opening 93 of a tibial tunnel portion 94, and into a fibula tunnel portion, exiting through an opening 96 of the fibula tunnel portion. This is achieved in the fashion described above, employing a pulling suture. The button 12 is then flipped, employing a flipping suture, and secured relative to a surface 97 of the fibula 48.

Figure 18A:
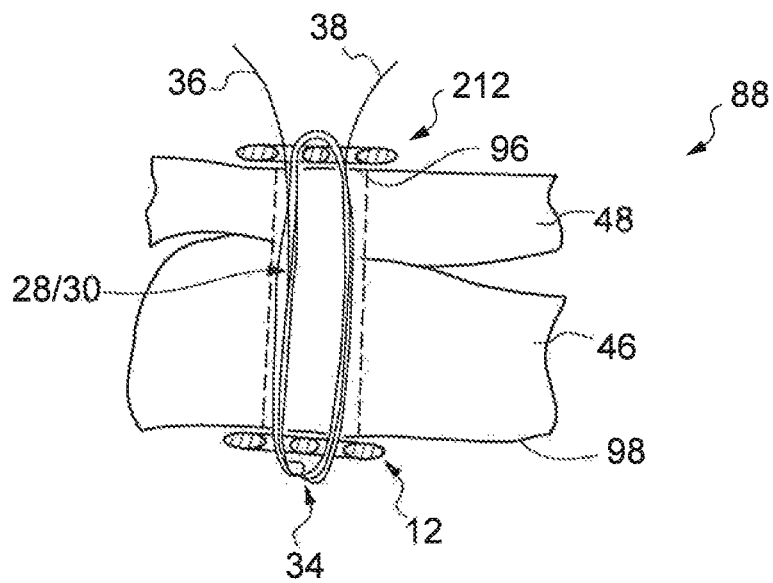
FIG. 18A is a simplified view that is similar to FIG. 18, but showing the implant assembly of FIG. 17 oriented in a reverse fashion in the bone tunnel of the syndesmotic ankle joint.

Of course, the reverse procedure may be adopted, in which the button 12 is inserted into the fibula tunnel opening 96. This is shown in the simplified view of FIG. 18A, where the button 12 is shown located on the tibial surface 98, so that the knot 34 is on the medial side of the joint 88, rather than the lateral side as shown in FIG. 18. The legs 36 and 38 have been directed down through apertures in the button 12 so that they trail behind the button as it is inserted into the tunnel through the fibula tunnel opening 96. This enables adjustment of the knot 34, and so the lengths of the support loops 28 and 30, from an end of the bone tunnel which is opposite to the end at which the knot 34 is located. This can be assist a surgeon, and may have other benefits including cosmetic and patient comfort.

The support loops 28 and 30 extend along the bone tunnel (comprising the tibia and fibula portions 94 and 95) between the buttons 12 and 212, and can be used to maintain the bones 46 and 48 in their proper position, a length of the support loops being selected to define a desired distance between the two buttons. Insertion of the implant assembly 200 involves initially spacing the two buttons 12 and 212 a sufficient distance apart to allow for manipulation of the bones to restore them from the distracted position to their proper position shown in FIG. 18. Indeed, the implant assembly 200 itself may be used to restore the bones. This involves providing the support loops 28 and 30 with a sufficient degree of slack to allow for such manipulation of the bones. Once the first button 12 has been positioned on the fibula surface 97, the support loops 28 and 30 can be shortened, following the procedure described above (by pulling on the legs 36 and 38), to bring the second button 212 into contact with a surface 98 of the tibia 46. This requires that the second button 212 be in its 'flipped' position shown in the drawing. Further tension is then applied to the legs 36 and 38, to apply sufficient tension to the support loops 28 and 30 to restore function to the ankle joint 88 and maintain the bones 46 and 48 in their proper position.

The implant assembly 200 is constructed following the method steps set out above in relation to FIGS. 2 to 11, save that the element 14 passes through the apertures of the second button 212 in the steps that are employed to form the support loops 28 and 30, so that the support loops each effectively pass through (and carry) the second button. The second button 212 is arranged so that its bone facing surface 216 faces towards the bone facing surface 16 of the first button 12. The portions of the support loops 28 and 30 extending between the bone facing surfaces 16 and 216 of the first and second buttons 12 and 212 effectively define an implant, which is located in the bone tunnel. Adjustment of the lengths of the support loops 28 and 30 adjusts a length of the implant that is formed, and a distance between the first and second buttons 12, 212. This enables adjustment of the implant assembly 200 to account for anatomical differences from patient-to-patient.

Figure 19:
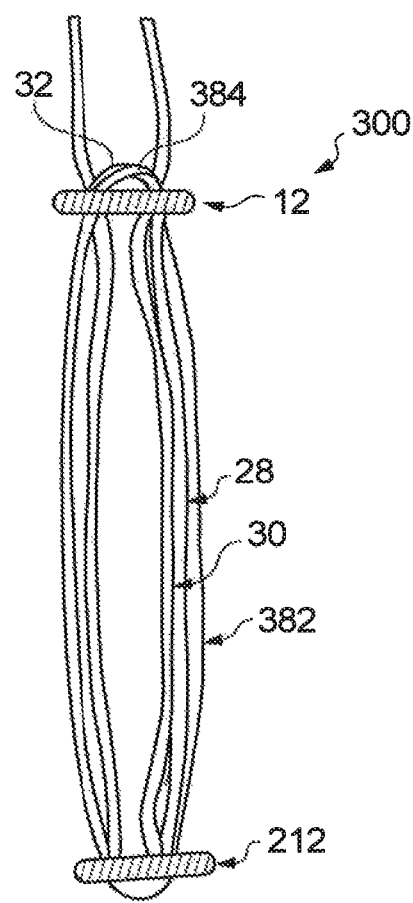
FIGS. 19 to 22 are front views of implant assemblies in accordance with further embodiments of the present invention, shown in assembled states.

FIG. 19 shows an implant assembly 300 in accordance with another embodiment of the invention, which is a variation on the implant assembly 200 shown in FIGS. 17 and 18. The implant assembly 300 is basically of the same construction as the implant assembly 200, save that it includes a third bone-side loop in the form of a support loop 382 and a second fixation loop 384, which are formed following the method set out in FIGS. 12 to 16 described above. As with the implant assembly 200, the support loops 28, 30 and 382 each effectively pass through (and carry) the second button 212.

Figure 20:
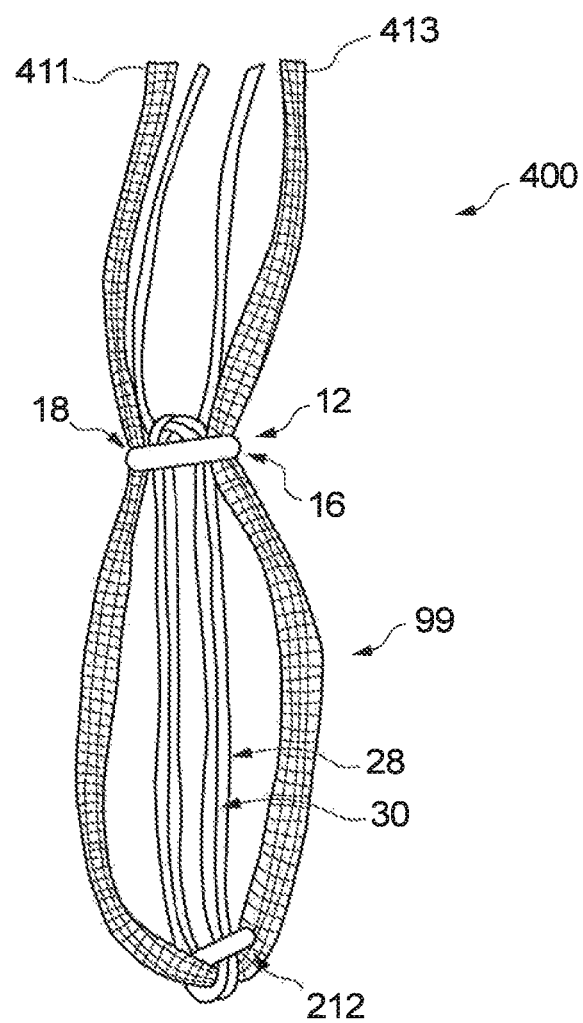

FIG. 20 shows an implant assembly 400 in accordance with another embodiment of the invention, which is a further variation on the implant assembly 200 shown in FIG. 18. The implant assembly 400 is of the same construction as the implant assembly 200, save that it includes a separate, second implant 99 which is coupled directly to the first button 12 and can be tensioned independently of the first implant formed by the support loops 28 and 30. The second implant 99 is directly coupled to the first button 12 by passing it through the third and fourth apertures 62 and 64 (FIG. 2), although it is conceivable that the implant could pass through the first and second apertures 20 and 22. The second implant 99 extends from the third aperture 62 at the bone facing surface 16 of the first button 12 to the fourth aperture 64 at the bone facing surface, to effectively form a further support loop. The second implant 99 is also coupled to the second button 212, and is secured by the element 14, by directing the loops 28 and 30 over the implant, to clamp it to the outer surface 218 of the second button.

The second implant 99 may be a synthetic implant, for example a fabric implant, particularly comprising or formed of a woven material (similar to the implant 54 discussed above). The implant assembly 400 is located in the bone tunnel of the ankle joint 88 following a similar procedure to that shown in FIG. 18 and discussed above, with the additional step of directing the legs 411 and 413 of the implant 99 out of the fibula tunnel opening 95. The implant assembly 400 may suitably be directed through the fibula opening 96 in this case, with the legs 411 and 413 of the second implant 99 trailing, in which case the second button 212 will form the lead button. The legs 411 and 413 will suitably be secured to the outer surface 97 of the fibula 48 (e.g. using staples) and cut to a desired length. The open nature of the second implant 99 helps to fill the bone tunnel and enhances tissue ingrowth.

Figure 21:
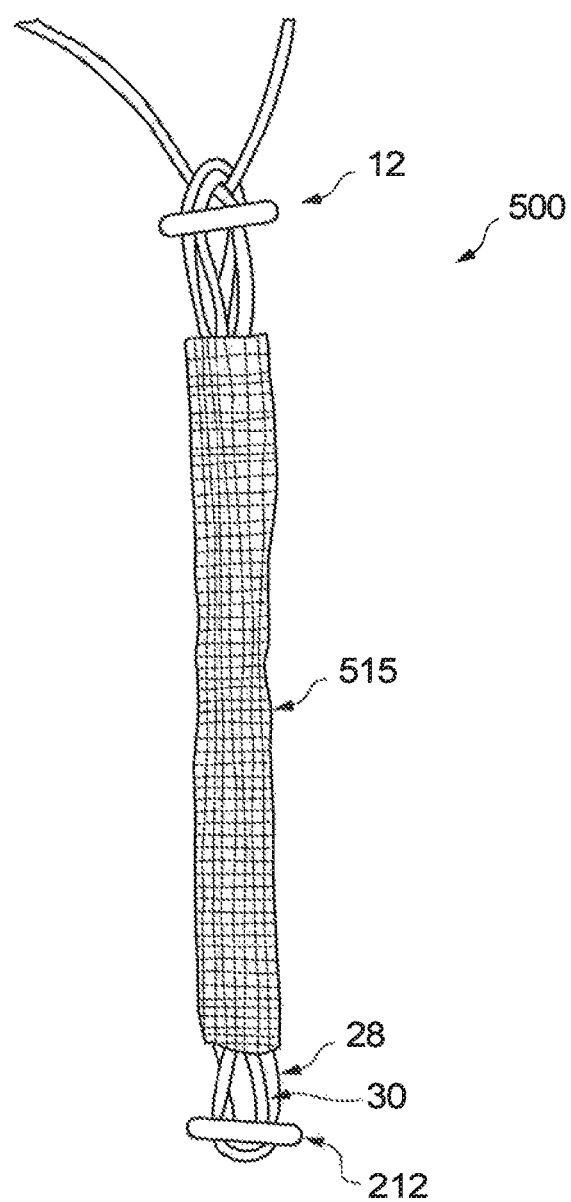

FIG. 21 shows an implant assembly 500 in accordance with another embodiment of the invention, which is a variation on the implant assembly 200 shown in FIG. 18. The implant assembly 500 is basically of the same construction as the implant assembly 200, save that it includes a tubular sheath 515 positioned around the support loops 28 and 30. The tubular sheath 515 is synthetic, of a fabric material, particularly a fabric comprising or formed of a woven material, which promotes tissue ingrowth. Providing a sheath 515 which is tubular facilitates fitting of the sheath around the support loops 28 and 30, as the sheath can simply be slid over the second button 212 and on to the support loops. Providing the sheath 515 of a fabric, particularly woven material, enables the sheath to easily decrease in length (and increase in width), or increase in length (and decrease in width) according to the desired lengths of the support loops 28 and 30. This may help to fill the bone tunnel, promoting tissue ingrowth. The method of construction and implantation of the assembly 500 is otherwise as described above.

Figure 22:
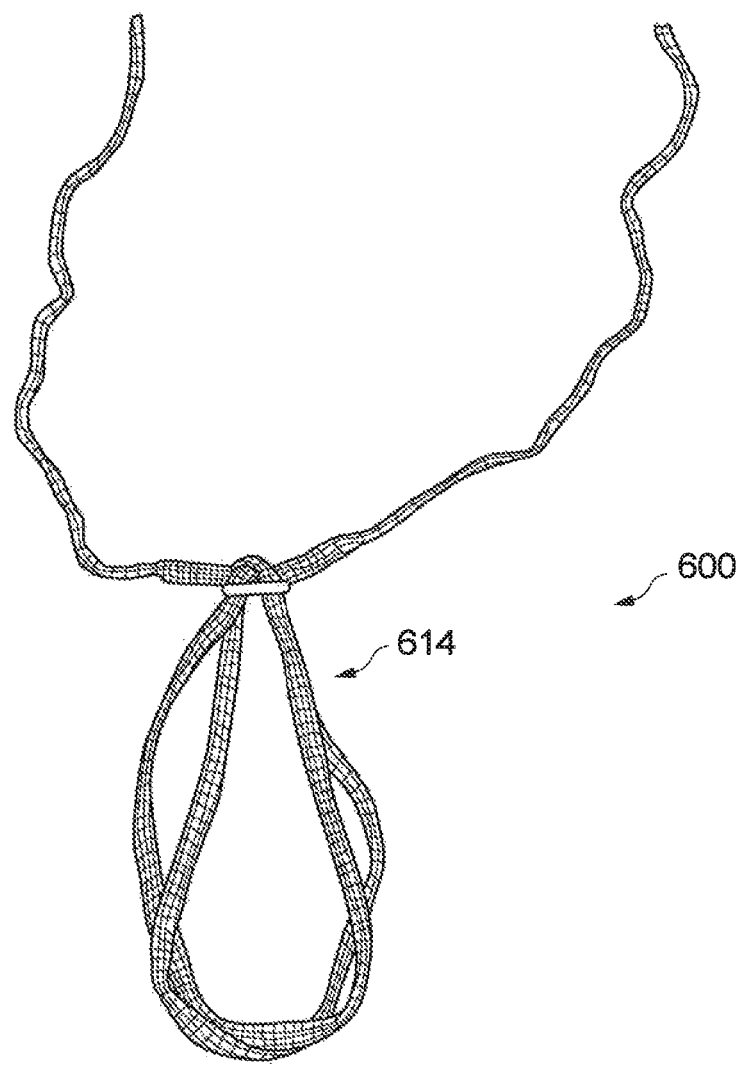

FIG. 22 shows an implant assembly 600 in accordance with another embodiment of the invention, which is a variation on the implant assembly 10 shown in FIG. 1. The implant assembly 600 is basically of the same construction as the implant assembly 10, save that it includes a flexible elongate element 614 which comprises or is formed of a woven material, similar to the implant 54 shown in FIGS. 3 and 4 and described above. This provides good tensile strength (in a direction along warp fibres of the fabric), whilst facilitating tissue ingrowth into apertures between the warp and weft fibres. The method of construction and implantation of the assembly 600 is otherwise as described above.

Figure 23:
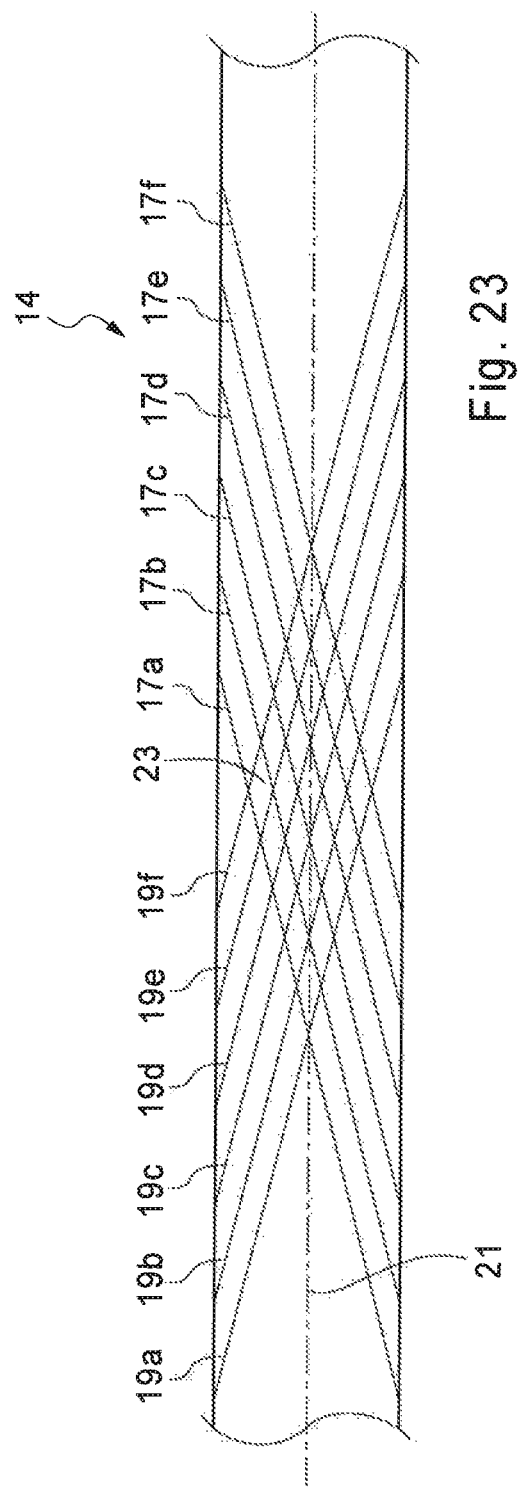
FIG. 23 is an enlarged schematic side view of a braided structure of the flexible elongate element forming part of the implant assembly shown in FIG. 1.

The implant assemblies of the present invention (with the exception of the woven assembly 600 shown in FIG. 22) may be formed of a braided material, and so may comprise a flexible elongate element which is braided. This is illustrated in FIG. 23, which is an enlarged schematic side view of a braided structure of the flexible elongate element 14 forming part of the implant assembly 10 discussed above. It will be understood that the braided structure shown in the drawing may be employed in any of the other assemblies 100 to 500 discussed above.

Figure 24:
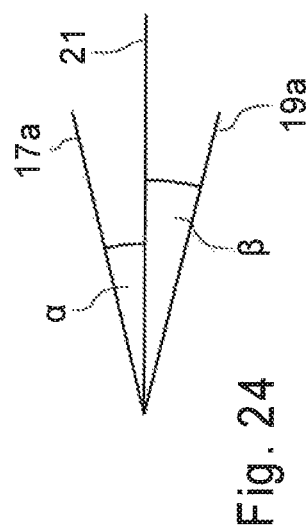
FIG. 24 is a further enlarged view of part of the braided structure shown in FIG. 23, which illustrates braid angles defined between fibres of the structure and a longitudinal axis of the flexible elongate element.

The braided structure comprises a first set of fibres (17a to 17f in the drawing) passing in a first direction around a circumference of the elongate element 14, and a second set of fibres (19a to 19f) passing in a second direction around the circumference of the elongate element. The fibres are typically yarns of a polymeric implantable material, but may be monofilaments or twisted bundles of fibres. The first fibres 17a to 17f are disposed transverse to the second fibres 19a to 19f, and transverse to a longitudinal axis 21 of the elongate element 14. Braid angles are defined between the fibres and the longitudinal axis. This is shown in the enlarged view of FIG. 24, which illustrates a braid angle $\alpha$ defined between the fibres 17a to 17f and the axis 21 (the fibre 17a shown in the drawing), and a braid angle $\beta$ defined between the fibres 19a to 19f and the axis 21 (the fibre 19a being shown).

The braid angles $\alpha$ and $\beta$ are no more than around 30°, suitably between around 15° and around 30°, and particularly around 15°. Arrangement of the fibres with such small braid angles provides numerous advantages. These include that a degree of extension of the elongate element 14 (and so the support loops 28) is restricted, in comparison to prior braided implant assemblies having a similar operative length to that defined by the support loops 28; a greater recovery in the absence of or under reduced loading (and so a behaviour more alike to native tissue); and/or that the braided construction is relatively 'open', defining elongate generally diamond-shaped openings (indicated at 23 in FIG. 23) which promote tissue ingrowth following implantation.

Figure 25:
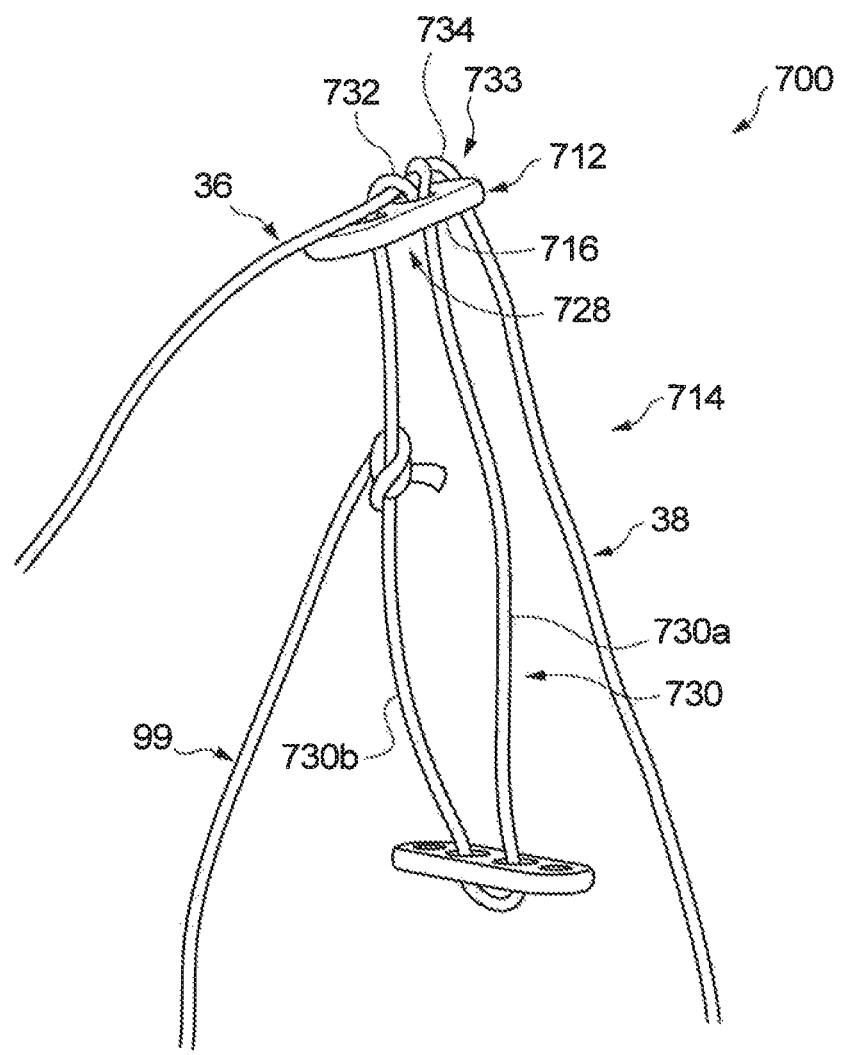
FIG. 25 is a front view of an implant assembly in accordance with another embodiment of the present invention, shown in an assembled state.
Figure 26:
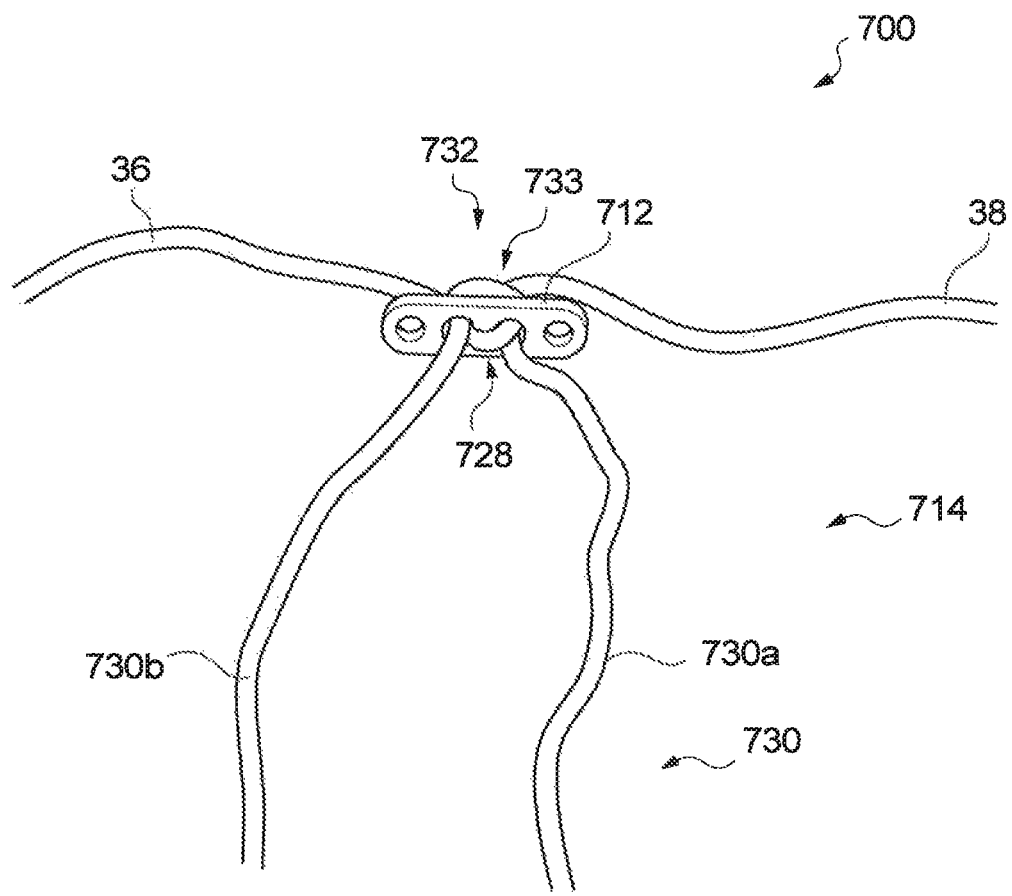
FIG. 26 is an enlarged view of the implant assembly shown in FIG. 25.

Turning now to FIG. 25, there is shown an implant assembly 700 in accordance with another embodiment of the invention, which is a variation on the implant assembly 200 shown in FIGS. 17 and 18. In this embodiment, one of two bone-side loops 728 and 730 is drawn into contact with a bone-facing surface 716 of a fixation device in the form of a button 712, suitably by shortening the loop. In the illustrated embodiment, it is the bone-side loop 728 which is drawn into contact with the bone-facing surface 716 of the button 712, the loop 728 shown in the enlarged view of FIG. 26.

The bone-side loop 728 cooperates with a fixation loop 732 and knot arrangement 733 (including knot 734) to secure flexible elongate element 714 to the button 712, forming a locking loop. The other bone-side loop 730 forms a support loop which defines an implant, although in a variation an implant assembly like that of FIG. 1 may be provided, in which case the support loop serves for locating an implant (e.g. a graft) in the bone tunnel.

Adjustment of a length of the support loop 730 can advantageously be achieved by applying tension to one of first and second loop portions 730*a* and 730*b* of the support loop, suitably the loop portion 730*b* which extends from one side of the knot 734. Adjustment may be achieved by adjusting the knot 734, suitably by decreasing a length of one of legs 36 and 38. Applying tension to the other loop portion 730*a*, which extends from the fixation loop 732, serves to lock a length of the support loop 730.

The implant assembly also comprises a knot-adjusting element 99, in the form of a cord, for adjusting the knot 734. The knot-adjusting element 99 is coupled to the loop portion 730*b* which extends from the side of the knot 734 mentioned above, suitably by knotting, tying or bonding. The application of tension to the knot-adjusting element 99 therefore adjusts the length of the leg 38. The leg 38 is shown passing down through an aperture in the button 712. The leg 36 will typically also be passed down through a button 712 aperture, such location facilitating adjustment from an opposite end of the tunnel to the knot 734 as discussed above.

Tensile loading tests carried out on implant assemblies of the type shown in the drawings, and constructed according to the principles outlined above, have shown that the implant assembly of the invention has a high resistance to slippage of the knot arrangement, and so elongation of the support loops under applied loading.

Figure 27:
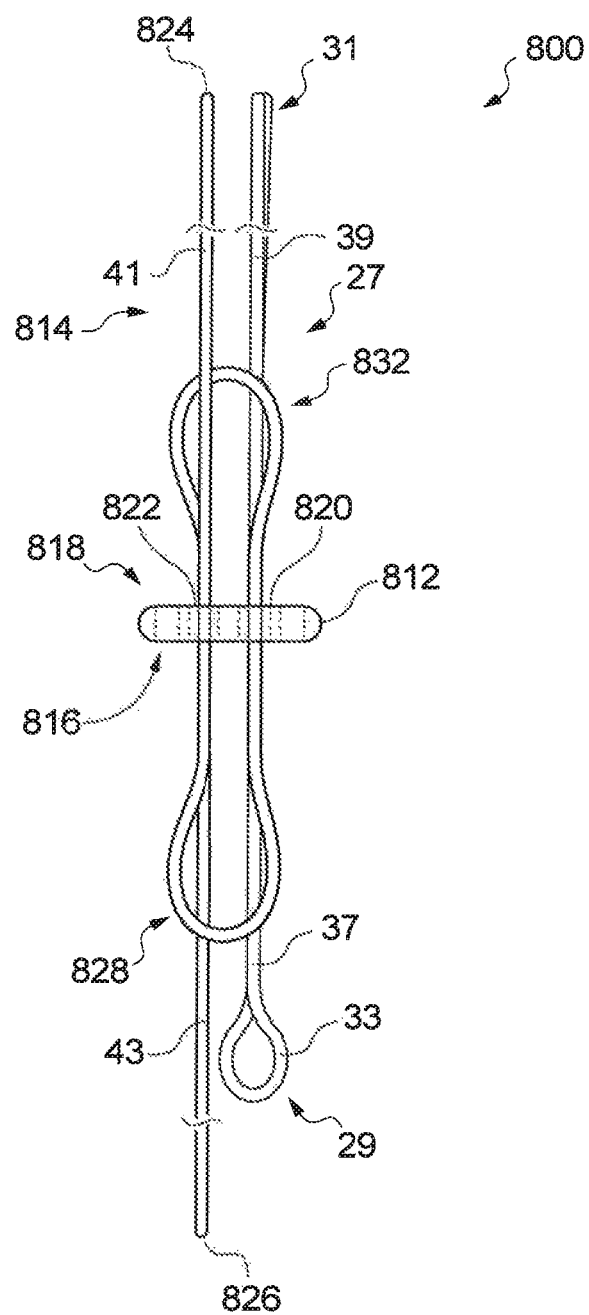
FIG. 27 is a front view of an implant construction device for forming an implant assembly adapted to be used in tissue repair, in accordance with an embodiment of the present invention, the implant construction device shown in a partially assembled state.
Figure 28:
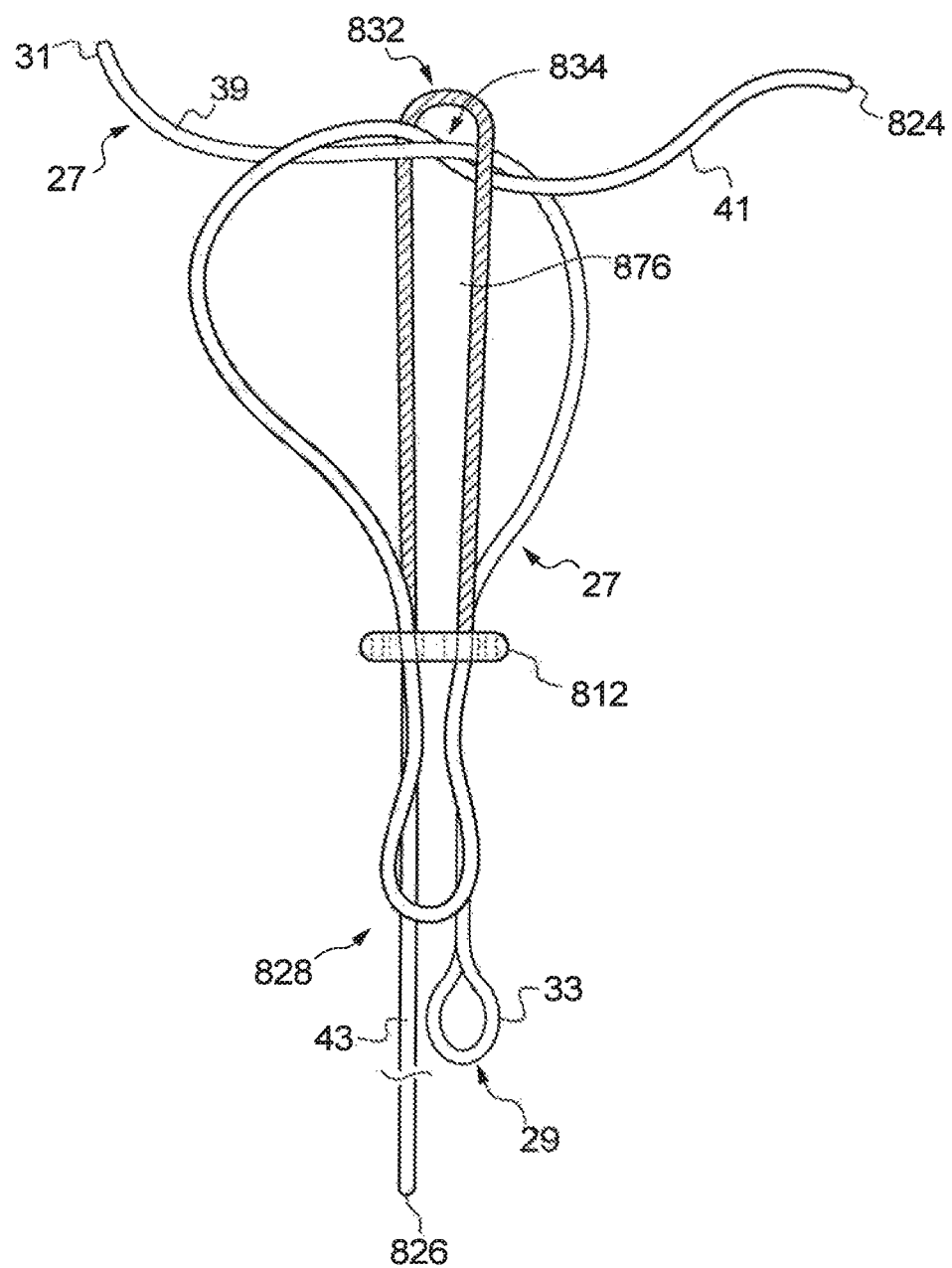
FIGS. 28 and 29 are front and plan views of the implant construction device shown in FIG. 27 in a fully assembled state.

Turning now to FIGS. 27 and 28, there are shown front views of an implant construction device in accordance with an embodiment of the present invention, the implant construction device indicated generally by reference numeral 800. FIG. 27 shows the implant construction device 800 in a partly assembled state, whilst FIG. 28 shows the device in a fully assembled state.

The implant construction device 800 has a use in forming an implant assembly adapted to be used in tissue repair, which can be any of the implant assemblies described in this document and shown in the attached drawings. In the illustrated embodiment, the implant construction device 800 has a use in forming an implant assembly which is similar to the implant assembly 10 shown in FIGS. 1 to 11C, and in particular which has the features of the variation shown in FIGS. 11A to C. Parts of the implant construction device 800 which are common to parts of the implant assembly 10 (and other implant assemblies disclosed herein) share the same reference numerals, incremented by 800.

The implant construction device 800 comprises a fixation device 812, a flexible elongate element 814 coupled to the fixation device, and a manipulating element 27 for use in constructing the implant assembly.

The fixation device 812 is of similar construction to the fixation device 12 described above, and comprises a bone facing surface 816, an outer surface 818 opposite the bone facing surface, a first aperture 820 and a second aperture 822, each aperture extending through the fixation device from the outer surface to the bone facing surface. The flexible elongate element 814 is of similar construction to the flexible elongate element 14 described above, and has a first end 824 and a second end 826.

The manipulating element 27 is flexible and elongate, comprising a first end 29 and a second end 31, the first end forming at least part of a capturing loop 33. The manipulating element 27 extends through an aperture of the fixation device 814, in this case the aperture 820, so that a portion 37 of the manipulating element comprising its first end 29 extends from the aperture at the bone facing surface 816 of the fixation device 814, and so that a portion 39 of the manipulating element comprising its second end 31 extends from the aperture at the outer surface 818 of the fixation device 814.

The implant construction device 800 also comprises an adjustable knot 834 which is positionable on the outer surface of the fixation device 814. The knot 834 is shown in FIG. 28, and takes the form of an overhand knot of the type described above.

The flexible elongate element 814 passes through apertures 820, 822 of the fixation device 814 to form a bone-side loop 828 and a fixation loop 832. The bone-side loop 828 extends from one of the apertures 820, 822 at the bone facing surface 816 of the fixation device 814 to another one of the apertures at the bone facing surface.

The fixation loop 832 extends from one of the apertures 820, 822 at the outer surface 818 of the fixation device 814 to another one of the apertures at the outer surface.

A portion 41 of the flexible elongate element 814 comprising the first end 824 extends from one of the apertures 820, 822 (in this case the aperture 822) at the outer surface 818 of the fixation device 814, and a portion 43 of the flexible elongate element comprising the second end 826 extends from one of the apertures 820, 822 (in this case the aperture 822) at the bone facing surface 816 of the fixation device.

The adjustable knot 834 is formed by the portion 39 of the manipulating element 27 extending from the aperture 820 and comprising its second end 31, and the portion 41 of the flexible elongate element 814 extending from the aperture 822 and comprising its first end 824.

The flexible elongate element 814 is arranged so that it follows a path which extends continuously through the apertures 820 and 822 in the fixation device 812 to form the bone-side loop 828, the fixation loop 832, and its part of the adjustable knot 834.

Coupling of the flexible elongate element 814 to the fixation device 812 to form the bone-side loop 828 and the fixation loop 832 essentially follows the procedure set out for the implant assembly 10 in FIGS. 5, 6 and 11A to C described above. Indeed, it will be noted that the partially assembled construction device 800 as shown in FIG. 27 is much the same as the partially assembled implant assembly 10 shown in FIG. 6, save that it additionally includes the manipulating element 27. The manipulating element 27 can be located in its position extending through the aperture 820 prior to or following the flexible elongate element 814, and can be directed down through the aperture from the outer surface 818, or up through the aperture from the bone-face surface 816. Typically, the manipulating element 27 is positioned on the other side of the fixation loop 832 from the portion 41 of the flexible elongate element 814, so that the knot 834 which is subsequently formed is clamped in a similar way to the knot 34 shown in FIGS. 11B and C. However, it will be understood that the manipulating element 27 may be located on the same side of the fixation loop 832 as the portion 41 of the flexible elongate element 814, so that the knot 834 which is formed is clamped in a similar way to the knot 34 shown in FIGURE in a similar way to FIGS. 10 and 11.

The portion 39 of the manipulating element 31, and the portion 41 of the flexible elongate element 814, are then manipulated to form the adjustable knot 834, by directing the portion 39 of the manipulating element 27 in a first direction through an eye 876 of the fixation loop 832, and the portion 41 of the flexible elongate element 814 in a second opposition direction through the eye. The knot 834 which is thus formed is positioned between the outer surface 818 of the fixation device 812 and the fixation loop 834, so that the knot is clamped in a similar way to the knot 34 shown in FIG. 11C. This is illustrated in the enlarged plan view of FIG. 29. As can be seen from FIGS. 28 and 29, a part of the flexible elongate element 814 has been cross-hatched to aid identification of the fixation loop, and the different parts of the construction device forming the knot 834.

The implant construction device 800 provides flexibility in a procedure to implant an implant assembly formed using the device, for example by enabling the implant assembly to be adapted to the particular needs of a patient and/or a surgical procedure, such as by a surgeon or other skilled operator. This can include the coupling of a plug, such as a bone plug taken from a patient, to the implant assembly which is formed employing the implant construction device 800 (which will be described in more detail below).

Formation of the implant assembly using the implant construction device 800 is completed as follows. The second end 826 of the flexible elongate element 814 is positioned through the capturing loop 33 of the manipulating element 27, which is disposed on the bone-facing surface 816 side of the fixation device 812. The manipulating element 27 is then manipulated to draw the second end 826 (and the trailing portion 42 of the element 814) through the fixation device 812 to its outer surface 818. This can be achieved simply by gripping the portion 39 of the manipulating element 27 extending on the outer surface 818 side of the fixation device 812, and pulling the manipulating element to draw the capturing loop 33 (with the second end 826 of the elongate element 814) up through the aperture 820. Continued pulling of the portion 39 draws the manipulating element 27 through the structure of the adjustable knot 834, so that the portion of the knot formed by the manipulating element is replaced by the portion 43 of the flexible elongate element 814 comprising its second end 826. This may be facilitated by the structure of the overhand knot 834. In order to achieve this, it may be necessary to impart a balancing force on knot 834 by simultaneously pulling on the portion 41 of the elongate element 814 extending from the knot.

Once the flexible elongate element 814 has been drawn through the knot 834 in this way, the manipulating element 27 can be released from the flexible elongate element (by removing its end 826 from the capturing loop 33), and the manipulating element can be discarded. An implant assembly of the type shown in FIGS. 11B and C has then been formed, which can be adjusted and tensioned as described above. These steps can all be carried out by a surgeon or other skilled operator as a preparation to, or during, a surgical procedure.

In the illustrated embodiment, the portion 37 of the manipulating element 27 comprising the first end 29 and extending from the aperture 820 at the bone facing surface 818 of the fixation device 812 defines the entire capturing loop 33. The manipulating element 27 is defined by a single elongate element which is folded at a point along its length to form the capturing loop 33. The manipulating element 27 is of a textile material, suitably woven or braided, and is generally tubular. The manipulating element 27 is fed back on itself and extends through a side wall of the element and along an internal cavity, to form the capturing loop 33.

The manipulating element 27 may, however, be of a simplified structure, for example formed from a multifilament suture or the like which is folded and secured to itself at a point along its length so as to form the capturing loop 33, for example by a knot. Also, the capturing loop 33 may be defined partly by the portion 37 of the manipulating element 27 comprising the first end 29 and extending from the aperture 820 at the bone facing surface 816 of the fixation device 812, and partly by the portion 39 of the manipulating element comprising the second end 31 and extending from the aperture 820 at the outer surface 818 of the fixation device 812.

Figure 29:
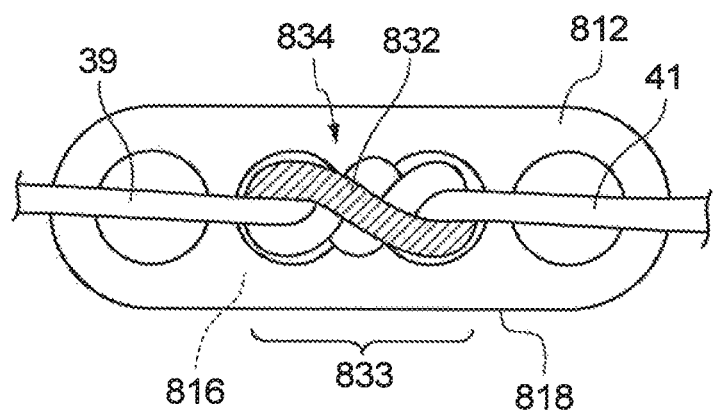

The adjustable knot 834 forms part of an adjustable knot arrangement 833 comprising the adjustable knot, a first leg extending from the knot and a second leg extending from the knot. The portion 39 of the manipulating element 27 and the portion 41 of the flexible elongate element 814 forming the knot also form the first and second knot legs. When the completed implant assembly is tensioned (via the bone side loop 828 and a further bone-side loop that is formed during assembly), the fixation loop 832 securely clamps the knot arrangement 833 to the fixation device 812, passing across the leg 39, knot 834 and leg 41, as shown in FIG. 29.

Mention is made above of the implant assembly carrying a plug, which can be coupled to the implant assembly by making use of the implant construction device 800. This can be achieved in different ways.

Figure 30:
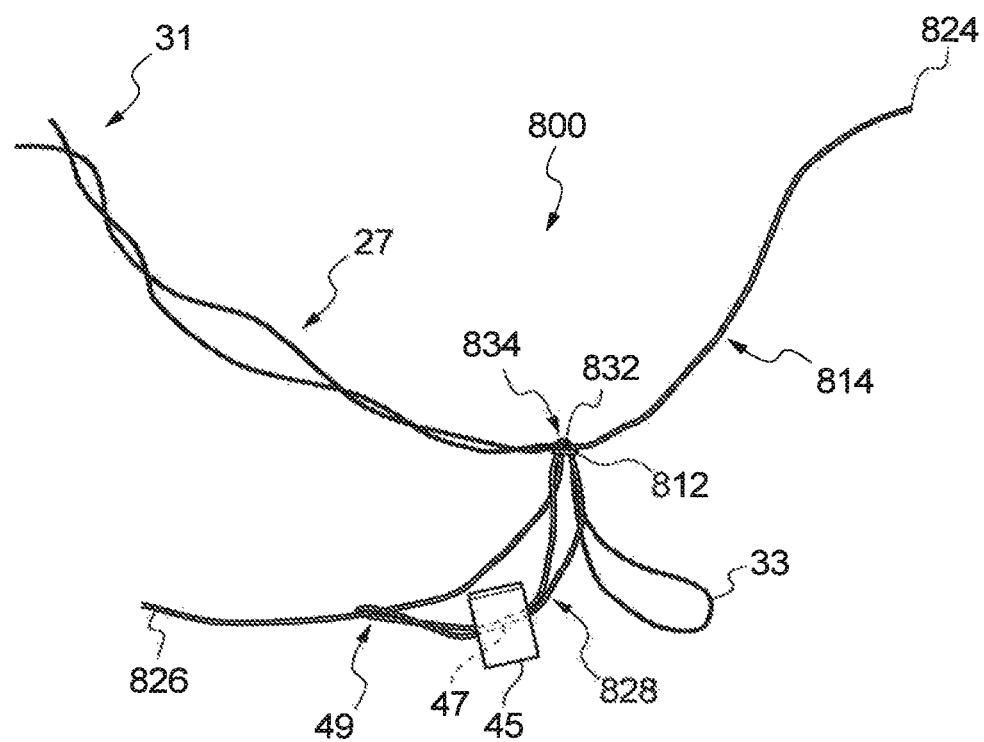
FIGS. 30 and 31 are front views of the implant construction device shown in FIG. 27 showing steps in a procedure to form an implant assembly using the implant construction device, involving the coupling of a plug to the device.
Figure 31:
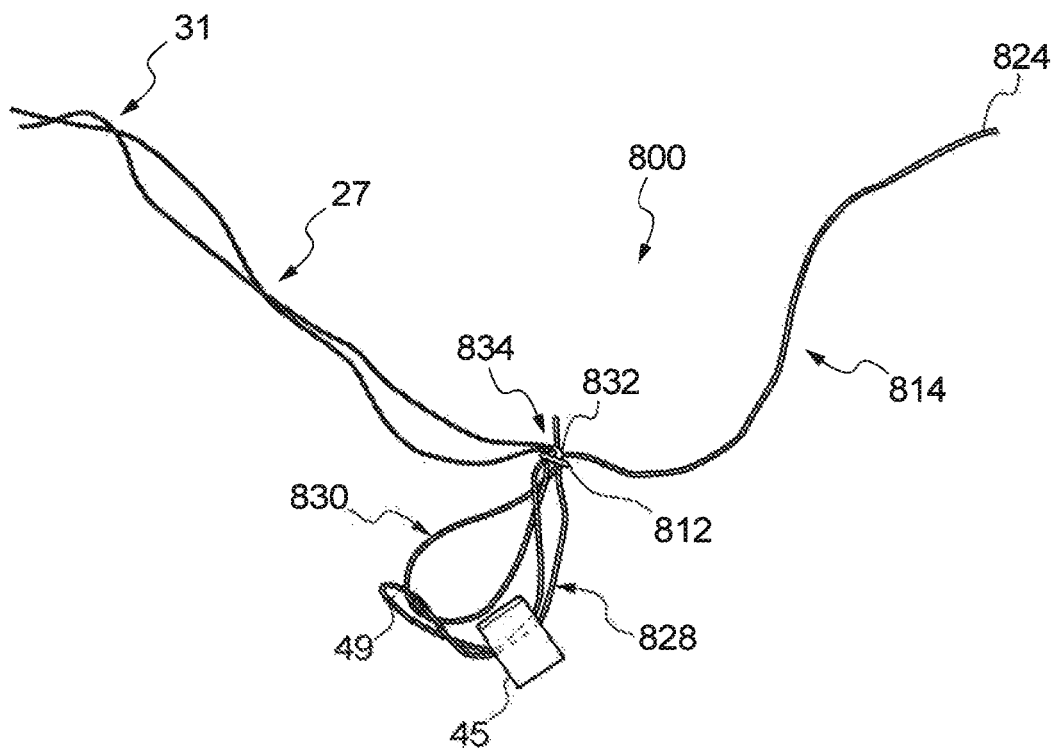

A first option is shown in the front views of FIGS. 30 and 31. The implant construction device shown in these drawings is actually a slight variation on that shown in FIGS. 27 to 29, employing a manipulating element 27 which is a simple length of material (e.g. a medical suture) that has been folded, and secured at a point along its length by knotting to form the capturing loop 33.

In this example, a plug in the form of a bone plug or block 45 is to be secured to the implant assembly which is being constructed using the implant construction device 800. The bone plug 45 is typically autologous, taken from a patient undergoing a surgical procedure to implant the implant assembly. The bone plug 45 shown in the drawings is generally cuboid, but can be any shape, and will often be generally cylindrical, taken from a patient's bone using a coring tool or the like. The bone plug 45 includes a passage 47 extending through it, which is shown in broken outline in FIG. 30.

In the illustrated embodiment, the bone side loop 828 is located through the bone plug passage 47, so that a part of the bone side loop protrudes from the plug 45. The second free end 826 of the flexible elongate element 814 is then located through the part of the bone side loop 828 protruding from the plug 45, suitably through an eye 49 of the loop. This is shown in FIG. 30. The second free end 826 is then directed through the capturing loop 33 of the manipulating element 27, and the manipulating element is used to draw the second free end up through the fixation device 812 to the outer surface 818 side, as described above. This forms a second bone-side loop 830, which passes through (and so is coupled to) the first bone-side loop 828, as shown in FIG. 31. The bone plug 45 is thus coupled to the implant assembly that is then formed, via the connected bone-side loops 828 and 830.

The bone block 45 may facilitate location of the implant assembly which is formed using the implant construction device 800 in a bone tunnel or channel, such as the femoral bone tunnel portion 44 shown in FIG. 3 and described above, in the case of an ACL repair procedure. The bone plug 45 may facilitate tissue ingrowth into the tunnel, and may locate the implant assembly by being seated against a ledge in the tunnel, for example at an interface between a larger dimension portion (which can accommodate the bone plug 45) and a smaller dimension portion (which can accommodate an implant coupled to the bone plug). To this end, the plug may be coupled or couplable to an implant such as a prosthetic implant, which may be tubular defining a cavity which can receive the plug. Reference is made to the techniques disclosed in prior International Patent Publication no. WO-89/10101, the disclosure of which is incorporated herein by this reference. Other plugs, including implantable artificial ones, may be employed.

In a variation on this procedure, the first end 29 of the manipulating element 27 may alternatively be directed through the bone plug passage 47, and used to draw the second end 826 of the flexible elongate element 814 through the plug 45, and then through the fixation device to its outer surface side as described above. The bone plug 45 may then be positioned on the bone side loop 830 which is thereby formed. Optionally, the second end 826 of the flexible elongate element 814 may be directed through the eye 49 of the first bone-side loop 828 before being passed through the capturing loop 33, so that the bone-side loop 830 which is formed is again coupled to the first bone-side loop 828.

In a variation on the implant construction device 800, the manipulating element 27 can be fed through the same aperture 822 of the fixation device 812 as the portion 43 of the flexible elongate element 814 having the second free end 826. Manipulation of the manipulating element 27 to draw said end 826 up through the fixation device 814 would then have the effect of forming a bone-side loop which extends from a single aperture of the fixation device.

Turning now to FIG. 32, there is shown a front view of an implant construction device in accordance with another embodiment of the present invention, the implant construction device indicated generally by reference numeral 900. Like components of the implant construction device 900 with the device 800 shown in FIGS. 27 to 31 and described above share the same reference numerals, incremented by 100 or 900 as appropriate.

The implant construction device 900 again has a use in forming an implant assembly adapted to be used in tissue repair, which can be any of the implant assemblies described in this document and shown in the attached drawings. In the illustrated embodiment, the implant construction device 900 has a particular use in forming an implant assembly which is similar to the implant assembly 100 shown in FIGS. 12 to 16, modified to employ the different knot forming technique shown in FIGS. 11A to C, and optionally having a bone-side loop drawn up into contact with a fixation device of the implant assembly that is formed, in a similar fashion to the assembly 700 shown in FIG. 26.

The implant construction device 900 comprises a fixation device 912, a flexible elongate element 914 coupled to the fixation device, a first manipulating element 927 for use in constructing the implant assembly and a second manipulating element 927'.

Figure 33:
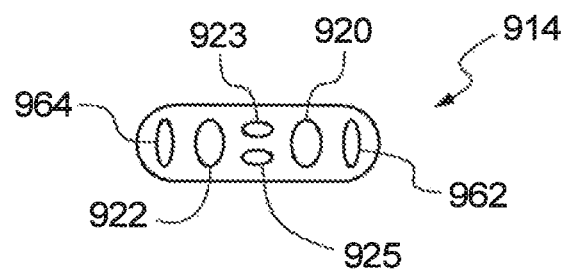
FIG. 33 is a plan view of a fixation device forming part of the implant construction device shown in FIG. 32.

The manipulating elements 927 and 927' each extending through an aperture of the fixation device 914, and suitably extend through different apertures. FIG. 33 is a plan view of a fixation device, in the form of a button such as an Endobutton™, which has a use in forming the implant construction device 900, and optionally other implant construction devices and implant assemblies disclosed in this document. The illustrated fixation device 912 comprises first and second apertures 920 and 922 which are spaced apart along a length of the device. Third and fourth apertures 923 and 925 are also provided, which are at generally common positions along the length of the fixation device 914, but which are spaced apart in a transverse direction, suitably in a direction which is generally perpendicular to a longitudinal axis of the fixation device, disposed on opposite sides of the axis. As will be described below, the various apertures 920, 922, 923 and 925 receive the flexible elongate element 914, and the first and second manipulating elements 927 and 927', to form the implant construction device 900 and so the resultant implant assembly. Further apertures 962 and 964 may be provided, which can receive parts of an implant assembly as described above, and/or pulling and flipping sutures used to draw the implant assembly along a bone tunnel and to position the fixation device 912.

In the illustrated embodiment, a portion 937 of the manipulating element 927 comprising a first end 929 of the element extends from the aperture 920 at a bone facing surface 916 of the fixation device 912. A portion 939 of the manipulating element 927 comprising a second end 931 extends from the aperture 920 at the outer surface 918 of the fixation device 912. In a similar fashion, a portion 937' of the manipulating element 927' comprising a first end 929' of the element extends from the aperture 922 at the bone facing surface 916 of the fixation device 912. A portion 939' of the manipulating element 927' comprising a second end 931' extends from the aperture 922 at the outer surface 918 of the fixation device 912.

The flexible elongate element 914 passes through the apertures 920, 925, 923 and 922 of the fixation device 912 so that a bone-side loop 928 is formed which extends from the aperture 925 at the bone facing surface 916 of the fixation device 912 to the aperture 923 at the bone facing surface. A first knot fixation loop 932 is formed which extends from the aperture 920 at the outer surface 918 of the fixation device 912 to the aperture 925 at the outer surface. A second knot fixation loop 984 is also formed, which extends from the aperture 923 at the outer surface 918 of the fixation device 912 to the aperture 922 at the outer surface. A portion 941 of the flexible elongate element 914 comprising a first end 924, and a portion 943 of the flexible elongate element comprising a second end 926, each extend from apertures at the bone facing surface of the fixation device (the apertures 920 and 922, respectively).

An adjustable knot 934 is formed which is positionable on the outer surface 918 of the fixation device 912. The adjustable knot 934 is formed by a portion 939 of the first manipulating element 927 extending from the aperture 920 and comprising its second end 931, and a portion 939' of the second manipulating element 927' extending from the aperture 922 and comprising its second end 931'. In a similar fashion to the implant construction device 800 shown in FIGS. 27 to 31, the knot 934 is formed by directing the portion 939 of the first manipulating element 927 in a first direction through eyes 976 and 986 of the fixation loops 932 and 984, and the portion 939' of the second manipulating element 927' in a second opposition direction through the eyes. The knot 934 which is thus formed is positioned between the outer surface 918 of the fixation device 912 and the two fixation loops 932 and 984, so that the knot can be clamped in a similar way to the knot 34 shown in FIG. 11C. However, other procedures can be used to form the knot, such as that shown in FIGS. 5 to 11 and described above.

FIG. 32 shows the implant construction device 900 in an assembled state, ready for use by a surgeon or other skilled operator in a procedure which involves constructing an implant assembly using the construction device. In this embodiment, construction of the implant assembly is achieved by positioning the first end 924 of the flexible elongate element 914 through a capturing loop 933 of the first manipulating element 927. In a similar fashion, the second end 926 of the flexible elongate element 914 is positioned through a capturing loop 933' of the second manipulating element 927'. The manipulating elements can then be manipulated to draw the first and second ends 924, 926 of the flexible elongate element 914 through the fixation device 912 to its outer surface 918, and through the adjustable knot 934. This forms two further bone-side loops (not shown in FIG. 32) and completes the implant assembly.

Since the first end 924 of the flexible elongate element 914 extends through a capturing loop 933 of the first manipulating element 927 (which passes through the same aperture 920 as the elongate element portion 941), the bone-side loop that is thereby formed extends from a single aperture of the fixation device 912. This is also true of the bone-side loop formed using the second manipulating element 927', which extends from the aperture 922. However, the first end 924 can be fed along the fixation device 912 and through the capturing loop 933' of the second manipulating element 927' to form a bone-side loop which extends from one aperture to another (from aperture 920 to aperture 922). Similarly, the second end 926 can be fed along the fixation device 912 and through the capturing loop 933 of the first manipulating element 927 to form a bone-side loop which extends from one aperture to another (from aperture 922 to aperture 920)

Typically, drawing of the ends 924 and 926 through the fixation device 912 will be carried out one at a time, but it is conceivable that both could be drawn through at the same time (which may require assistance from another operator). When drawing through, the portion 939 of the adjustable knot 934 formed by the first manipulating element 927 is replaced by the portion 941 of the flexible elongate element 914 comprising its first end 924. Similarly, the portion 939' of the adjustable knot 934 formed by the second manipulating element 927' is replaced by the portion 943 of the flexible elongate element 914 comprising its second end 926.

Figure 34:
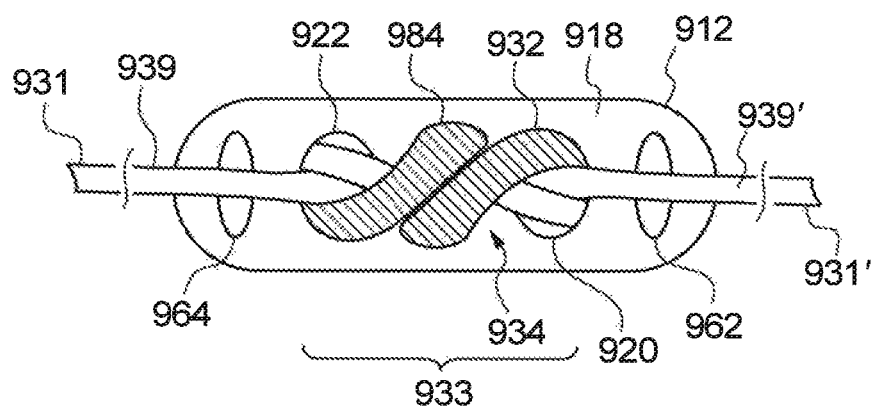
FIG. 34 is an enlarged plan view of the implant construction device shown in FIG. 32, in the fully assembled state.

The adjustable knot 934 forms part of an adjustable knot arrangement 933 comprising the adjustable knot, a first leg extending from the knot and a second leg extending from the knot. The portion 939 of the first manipulating element 927 and the 939' of the second manipulating element 927' forming the knot 934 also form the first and second knot legs. When the completed implant assembly is tensioned (via the two further bone-side loops), the fixation loops 932 and 984 securely clamp the knot arrangement 933 to the fixation device 912, passing across the leg 939, knot 934 and leg 939', as shown in the enlarged plan view FIG. 34, in which parts of the flexible elongate element 914 forming the fixation loops 932 and 984 have been cross-hatched.

Figure 35:
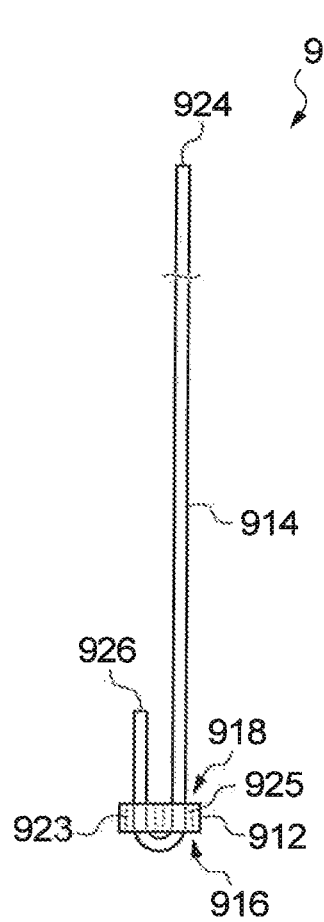
FIGS. 35 to 38 are front views of the implant construction device of FIG. 32, illustrating steps in a method of forming the device.
Figure 36:
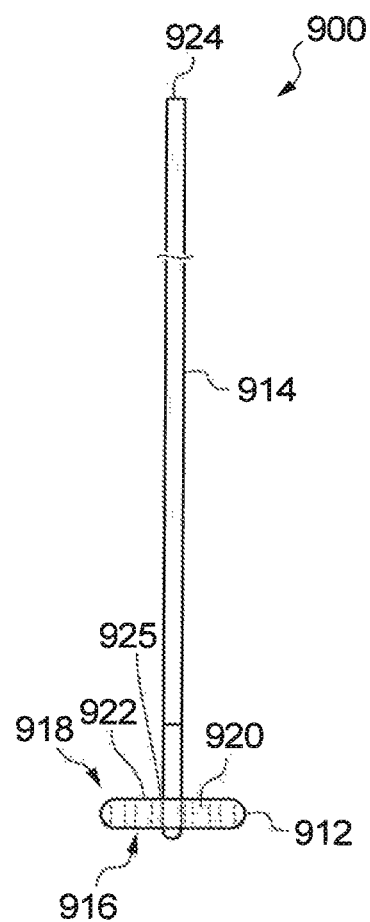
Figure 37:
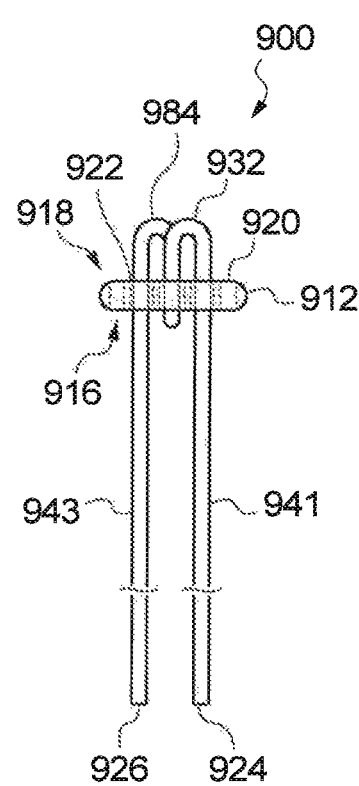
Figure 38:
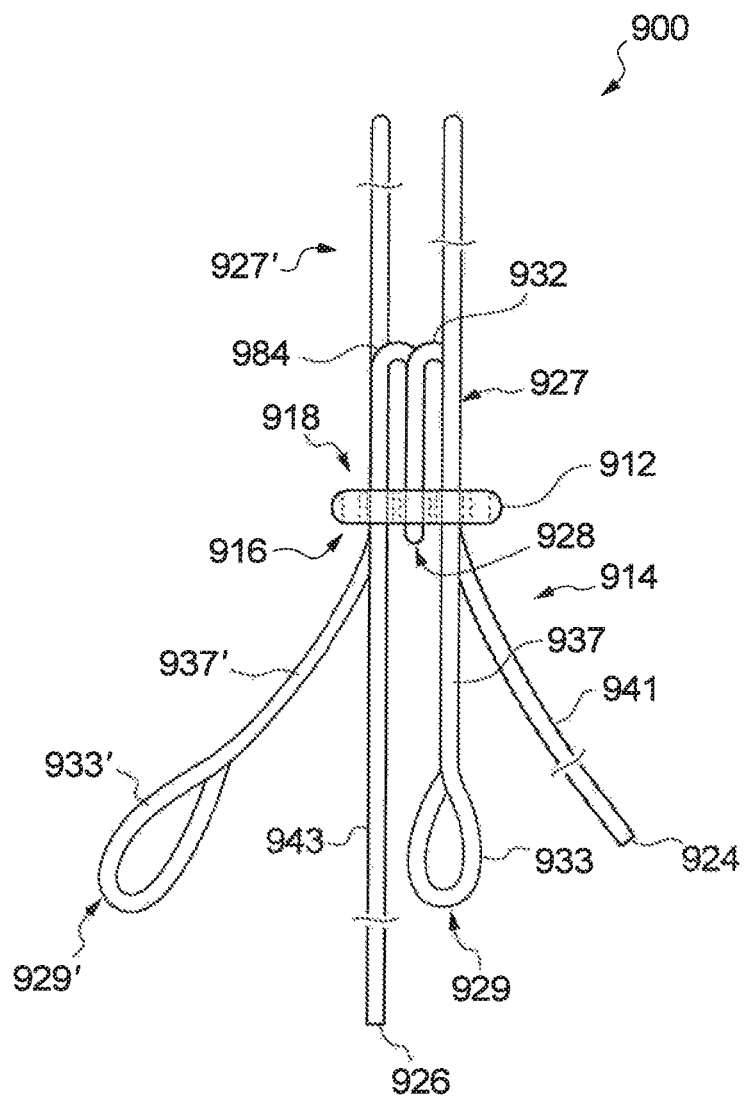

Steps in a procedure for forming the implant construction device 900 are shown in the end view of FIG. 35, and the front views of FIGS. 36 to 38. The flexible elongate element 914 is arranged so that it follows a path which extends continuously through relevant apertures in the fixation device 914 to form the bone-side loop 928, one of the fixation loops 932, 984 and the other fixation loop.

FIGS. 35 and 36 show a first step, which involves feeding the flexible elongate element 914 down through the fixation device 912 from its outer surface 918 side and through the aperture 925 (although it could be fed through another aperture, such as the aperture 923). The element 914 is then turned and passed back up through the aperture 923 of the fixation device (although this could be another aperture) to form the locking-type bone side loop 928. The element 914 is fed through these apertures 925 and 923 so that a sufficient working length of the element 914 is provided on the outer surface side of the fixation device 912.

The first end 924 is then fed down through the aperture 920 (although it could be fed through another aperture such as the aperture 922) so that it resides on the bone-facing surface 916 side. The second end 926 is then fed down through the aperture 922 (although it could be fed through another aperture such as the aperture 920) so that it also resides on the bone-facing surface 916 side. This serves to form the two fixation loops 932 and 984. These steps are shown in FIG. 37.

The two manipulating elements 927 and 927' can then be fed down through the apertures 920 and 922 respectively (although they could be fed through different apertures), as shown in FIG. 38. The adjustable knot 934 is then formed, as shown in FIG. 39. The free ends 924 and 926 of the flexible elongate element 914 are then fed respectively through the capturing loops 933 and 933'. The first and second manipulating elements 927 and 927' are then manipulated to form the further bone-side loops and to draw the elongate element portions 941 and 943 through the knot 934 to replace the manipulating elements (which can then be dispensed with), forming the implant assembly.

Optionally, and as shown in the front view of FIG. 39, an adjusting element such as a suture 51 can be coupled to the bone-side loop 928, so that a length of the loop can be adjusted in situ. This may enable a length of each of the bone-side loops of the completed implant assembly to be adjusted in situ, by loosening the adjustable knot 934, and pulling on suture 51 to feed material from the knot legs into the bone-side loops. To this end, the suture 51 may have a length which is sufficient to span the bone tunnel or channel in which the implant assembly is located, so that the suture can be gripped to carry out such adjustment.

In a similar fashion to the implant construction device 800, a plug such as a bone plug can be coupled to the implant construction device 900, so that it forms part of the finished implant assembly. Steps in a method of feeding a bone plug on to the construction device 900 are shown sequentially in the front views of FIGS. 40 to 42, which commence with the device as shown in the position of FIG. 32.

A bone plug 945 is shown which is coupled to a prosthetic implant 57, for example by locating the plug in a pocket in a tubular structure of the implant, following the teachings of WO-89/10101. In a first step, the first and second manipulating elements 927 and 927' are fed through a passage 947 in the bone plug 945 so that at least part of their capturing loops 933 and 933' (and optionally the entire loops) protrude from the passage. This is shown in FIG. 40.

The first end 924 of the elongate element 914 is then fed through the first capturing loop 933, and the second end 926 fed through the second capturing loop 933' (or vice-versa), as described above. The first and second manipulating elements 927 and 927' are then drawn back up through the bone plug passage 947, suitably by pulling on the portions 939 and 939' of the manipulating elements, as shown by the arrows 'A' in FIG. 41. This serves to draw the first and second ends 924 and 926 of the elongate element 914 (located in the capturing loops 933 and 933') up through the plug passage, as again shown in FIG. 41.

The first and second manipulating elements 927 and 927' are then drawn back up through the fixation device 912 and through the knot 934, so that they are replaced in the knot by the portions 941 and 943 of the flexible elongate element 914, as described above. This is shown in FIG. 42. This serves to form two further bone-side loops 930 and 982, which each extend from a single aperture of the fixation device 912 (apertures 920 and 922, respectively). As can be seen from FIG. 42, the bone-side loops 930 and 982 that are thereby formed pass through the bone plug passage 947 and so mount the plug 945 (and the trailing implant 57) to the fixation device 912 via the bone-side loops.

Variations on this plug mounting technique may involve first forming one of more of the bone-side loops 928, 930 and 982, and then passing one or more of said loops through the plug passage 947, and using a manipulating element or elements to form a further bone-side loop passing through said loop or loops to secure the bone plug 945, following the technique shown in FIGS. 30 and 31 and described above.

Various modifications may be made to the foregoing without departing from the spirit or scope of the present invention.

For example, the flexible elongate element may be a monofilament. The flexible elongate element may be a fabric element, and may comprise or be formed of a woven material. This may provide good tensile strength (in a direction along warp fibres of the fabric), whilst facilitating tissue ingrowth into apertures between the warp and weft fibres.

Numerous different embodiments and aspects of the invention are disclosed in this document. Further embodiments and/or aspects may comprise one or more feature selected from one of more embodiments/aspects of the invention.

Methods of repairing damaged connective tissue are disclosed herein, which tissue may comprise a ligament or tendon. Methods of repairing a damaged ACL and a damaged syndesmotic joint have been shown in the drawings and discussed above. The implant assembly of the invention may have a use in other surgical methods, including but not restricted to repair of a damaged acromioclavicular joint (ACJ). Methods of repairing a damaged ACJ which may employ the implant assembly of the present invention are disclosed in prior International patent application no. PCT/GB2016/052202 (published as WO-2017/013431), in which the present applicant is a joint applicant, and the disclosure of which is incorporated herein by this reference.

The features of one or more of the implant assemblies, implant construction devices and methods disclosed in this document may be combined to form further embodiments or aspects of the invention. Such embodiments and aspects may comprise one or more feature taken from one of more embodiment or aspect disclosed in this document.

Different knots to the ones shown and described in this document may be employed (an overhand knot and a constrictor knot being particularly mentioned). In principle, any type of knot which can be adjusted to form the implant assemblies/construction devices may be employed.

The invention claimed is:

1. An implant assembly for use in tissue repair, the implant assembly having an adjustable length and comprising:
   a fixation device comprising a bone facing surface, an outer surface opposite the bone facing surface, and a plurality of apertures; the plurality of apertures comprising a first aperture extending through the fixation device from the outer surface to the bone facing surface, and at least a second aperture extending through the fixation device from the outer surface to the bone facing surface;
   a flexible elongate element secured to the fixation device, the flexible elongate element having a first free end and a second free end, in which the flexible elongate element passes through at least two of the plurality of apertures of the fixation device so that:
   at least two bone-side loops are formed which each extend from at least one of the plurality of apertures at the bone facing surface of the fixation device, at least one of the bone-side loops forming a support loop adapted to be located at least partly within a bone tunnel;
   at least one fixation loop is formed which extends from one of the plurality of apertures at the outer surface of the fixation device to another one of the plurality of apertures at the outer surface of the fixation device; and
   an adjustable knot arrangement is formed, comprising the fixation loop and an adjustable knot which is separate from the fixation loop; the adjustable knot being positionable on the outer surface of the fixation device, between the outer surface of the fixation device and the fixation loop; a first leg extending from the knot to the first free end of the elongate element and a second leg extending from the knot to the second free end of the elongate element;
   in which the flexible elongate element is securable to the fixation device by the fixation loop, the fixation loop extending from said one of the plurality of apertures and passing over at least part of the adjustable knot arrangement to said another one of the plurality of apertures, to clamp the adjustable knot to the fixation device, between the outer surface of the fixation device and the fixation loop, when the bone-side loops are tensioned relative to the fixation device;
   so as to allow a length of each of the bone-side loops to be adjusted.

2. An implant assembly as claimed in claim 1, in which the adjustable knot assembly is an overhand knot assembly comprising an overhand knot.

3. An implant assembly as claimed in claim 1, in which the flexible elongate element is arranged so that it follows a path which extends continuously through at least two of the plurality of apertures in the fixation device to form the at least two bone-side loops, the at least one fixation loop, and the adjustable knot.

4. An implant assembly as claimed in claim 3, in which the flexible elongate element is arranged so that it successively forms a first one of the bone-side loops, the fixation loop, a second one of the bone-side loops, and the adjustable knot.

5. An implant assembly as claimed in claim 1, in which the adjustable knot and the fixation loop together form a self-locking knot assembly which self-locks under load.

6. An implant assembly as claimed in claim 1, in which the adjustable knot is positioned between the outer surface of the fixation device and the fixation loop.

7. An implant assembly as claimed in claim 1, comprising at least one further bone-side loop which extends from one of the plurality of apertures at the bone facing surface of the fixation device to another one of the plurality of apertures at the bone facing surface.

8. An implant assembly as claimed in claim 1, in which the implant assembly comprises at least one further fixation loop which extends from one of the plurality of apertures at the outer surface of the fixation device to another one of the plurality of apertures at the outer surface of the fixation device, the further fixation loop passing over at least part of the adjustable knot arrangement.

9. An implant assembly as claimed in claim 1, in which the implant assembly is an implant fixation assembly for fixing an implant within a tunnel in a bone, the at least one bone-side loop forming an implant support loop adapted to receive the implant, for suspending the implant in the bone tunnel from the fixation device.

10. An implant assembly as claimed in claim 1, in which the at least one bone-side loop forming a support loop defines at least part of an implant which serves to replicate the function of damaged tissue.

11. An implant assembly as claimed in claim 1, in which:
the bone-side loops each have a first loop portion extending from one of the plurality of apertures to an apex of the loop, and a second loop portion extending from another one of the plurality of apertures to the apex of the loop;
the fixation loop has a first loop portion extending from one of the plurality of apertures to an apex of the loop, and a second loop portion extending from another one of the plurality of apertures to the apex of the loop;
the adjustable knot has a first knot portion extending from one side of the knot to one of the plurality of apertures, and a second knot portion extending from the other side of the knot to another one of the plurality of apertures;
the first loop portion of one of the bone-side loops extends from one side of the knot, and the second loop portion of the first bone-side loop extends from one of the first and second loop portions of the fixation loop; and
the first loop portion of the other bone-side loop extends from the other side of the knot, and the second loop portion of the other bone-side loop extends from the other one of the first and second loop portions of the fixation loop.

12. An implant assembly as claimed in claim 1, in which the fixation device is a first fixation device, and the assembly comprises a second fixation device comprising a bone facing surface, an outer surface opposite the bone facing surface, and a second plurality of apertures; the second plurality of apertures comprising a first-third aperture extending through the second fixation device from the outer surface to the bone facing surface, and at least a second fourth aperture extending through the second fixation device from the outer surface to the bone facing surface.

13. An implant assembly as claimed in claim 12, in which the first fixation device is adapted to be secured relative to a surface of a first bone of a joint and the second fixation device relative to a surface of a second bone of the joint, at least one of the bone-side loops adapted to extend along a bone tunnel between the fixation devices to maintain the bones in their proper position, a length of the loop being selected to define a desired distance between the two fixation devices.

14. An implant assembly as claimed in claim 12, in which the flexible elongate element also passes through one of the second plurality of apertures of the second fixation device and then back through another one of the second plurality of apertures of the second fixation device.

15. An implant assembly as claimed in claim 14, in which the second fixation device is arranged so that its bone facing surface faces towards the bone facing surface of the first fixation device, the second fixation device being located at a position which is spaced along a length of said bone-side loop from the first fixation device.

16. An implant assembly as claimed in claim 15, in which portions of said bone-side loop extending between the bone facing surfaces of the first and second fixation devices define an implant adapted to be located in a bone tunnel.

17. An implant assembly as claimed in claim 1, in which one or more of the bone-side loops forms a first implant and the implant assembly comprises a further implant coupled directly to the fixation device and tensionable independently of the first implant.

18. An implant assembly as claimed in claim 17, in which the fixation device is a first fixation device, and the assembly comprises a second fixation device comprising a bone facing surface, an outer surface opposite the bone facing surface, and a second plurality of apertures; the second plurality of apertures comprising a first-third aperture extending through the fixation device from the outer surface to the bone facing surface, and at least a second-fourth aperture extending through the fixation device from the outer surface to the bone facing surface and in which the further implant is coupled to the second fixation device.

19. An implant assembly as claimed in claim 1, comprising a tubular sheath positioned around the bone-side loop forming a support loop adapted to be located in the bone tunnel.

20. An implant assembly as claimed in claim 1, in which the fixation loop is arranged so that it passes: over the adjustable knot; over one of the first and second legs;
and/or over both the first and second legs, to clamp the knot arrangement to the fixation device when the bone-side loops are tensioned.

21. An implant assembly as claimed in claim 1, in which at least one bone-side loop forms a locking loop which is drawn into contact with the bone-facing surface of the fixation device, said bone-side loop cooperating with the fixation loop and the knot assembly to secure the flexible elongate element to the fixation device.

22. An implant assembly as claimed in claim 21, in which the bone-side loops each have a first loop portion extending from one of the plurality of apertures to an apex of the loop, and a second loop portion extending from another one of the plurality of apertures to the apex of the loop, and in which:
a length of the support loop is adjustable by applying tension to the loop portion which extends from one side of the knot; and
the length of the support loop is locked by applying tension to the other loop portion, which extends from the fixation loop.

23. An implant assembly as claimed in claim 22, comprising a knot-adjusting element for adjusting the knot, the knot-adjusting element being coupled to the loop portion which extends from said side of the knot.

24. An implant assembly as claimed in claim 1, in which the flexible elongate element is braided, comprising:
a first set of fibres passing in a first direction around a circumference of the elongate element, and a second set of fibres passing in a second direction around a circumference of the elongate element, the first fibres disposed transverse to the second fibres and transverse to a longitudinal axis of the elongate element;
and in which a braid angle is defined between the fibres and the longitudinal axis.

25. An implant assembly as claimed in claim 24, in which the braid angle is between around 15° and around 30°.

26. An implant assembly as claimed in claim 1, in which one or more of the bone-side loops that are formed extends from one of the plurality of apertures at the bone facing surface of the fixation device to another one of the plurality of apertures at the bone facing surface.

27. An implant assembly as claimed in claim 1, in which one or more of the bone-side loops that are formed extends from a same one of the plurality of apertures at the bone facing surface of the fixation device.

28. A method of manufacturing an implant assembly for use in tissue repair, the method comprising the steps of:
providing a fixation device comprising a bone facing surface, an outer surface opposite the bone facing surface, and a plurality of apertures; the plurality of apertures comprising a first aperture extending through the fixation device from the outer surface to the bone facing surface, and at least a second aperture extending through the fixation device from the outer surface to the bone facing surface;
coupling a flexible elongate element to the fixation device by passing the elongate element through at least two of the plurality of apertures of the fixation device to form:
at least two bone-side loops which each extend from at least one of the plurality of apertures at the bone facing surface of the fixation device, at least one of the bone-side loops forming a support loop adapted to be located at least partly within a bone tunnel;
at least one fixation loop which extends from one of the plurality of apertures at the outer surface of the fixation device to another one of the plurality of apertures at the outer surface of the fixation device; and
an adjustable knot arrangement comprising the fixation loop and an adjustable knot which is separate from the fixation loop; a first leg extending from the knot to a first free end of the elongate element and a second leg extending from the knot to a second free end of the elongate element;
and arranging the fixation loop so that it extends from the one of the plurality of said apertures and passes over at least part of the adjustable knot arrangement to said another one of the plurality of apertures, so that the adjustable knot can be clamped to the fixation device, between the outer surface of the fixation device and the fixation loop, when the bone-side loops are tensioned relative to the fixation device.

29. A method as claimed in claim 28, comprising a step A of:
directing the flexible elongate element through the first aperture of the fixation device and through the second of the plurality of apertures, so that a portion of the flexible elongate element including the first free end and a portion of the flexible elongate element including the second free end both extend from the first aperture and said second of the plurality of apertures on an outer surface side of the fixation device, to form one of the bone-side loops.

30. A method as claimed in claim 29, comprising a step B of:
directing the portion of the flexible elongate element which extends from the first aperture on the outer surface side of the fixation device through another of the plurality of apertures, so that said portion extends from said another aperture of the plurality of apertures on the bone facing surface side of the fixation device, to form the fixation loop.

31. A method as claimed in claim 30, comprising a step C of:
directing the portion of the flexible elongate element which extends from said another aperture of the plurality of apertures on the bone facing surface side of the fixation device through a different one of the plurality of apertures, so that the portions of the flexible elongate element including the first and second free ends both extend from the outer surface side of the fixation device, to form the other one of the bone-side loops.

32. A method as claimed in claim 31, comprising a step D of:
manipulating the portions of the flexible elongate element to form the adjustable knot.

33. A method as claimed in claim 32, comprising a step E of:
manipulating the adjustable knot so that it is positioned between the outer surface of the fixation device and the fixation loop, by directing at least one of the portions of the flexible elongate element through an eye of the fixation loop.

34. A method as claimed in claim 33, comprising a step F of:
manipulating the fixation loop to clamp the adjustable knot arrangement to the fixation device and thereby secure the flexible elongate element to the fixation device.

35. A method as claimed in claim 34, in which steps E and F are carried out by tensioning the bone-side loops.

36. A method as claimed in claim 34, in which the steps A to F are carried out sequentially.

37. A method as claimed in claim 31 comprising a step C2 which is carried out following step C, step C2 comprising:
directing the portion of the flexible elongate element which extends from the first aperture on the outer surface side of the fixation device back through any of the plurality of apertures of the fixation device, so that said portion extends from the bone facing surface side of the fixation device, to form a further fixation loop.

38. A method as claimed in claim 37 comprising a step C3 which is carried out following step C2, step C3 comprising:
directing the portion of the flexible elongate element which extends from said any of the plurality of apertures of the fixation device on the bone facing surface side through a different any of the plurality of apertures, so that the portions of the flexible elongate element including the first and second free ends again both extend from the outer surface side of the fixation device, to form a further bone-side loop.

39. A method as claimed in claim 29, in which:
the fixation device is a first fixation device, and the method comprises providing a second fixation device comprising a bone facing surface, an outer surface opposite the bone facing surface, and a second plurality of apertures; the second plurality of apertures comprising a third aperture extending through the further fixation device from the outer surface to the bone facing surface, and at least a fourth aperture extending through the further fixation device from the outer surface to the bone facing surface; and
the method, in step A, comprises directing the flexible elongate element through the first third and fourth apertures of the second fixation device so that the second fixation device is disposed on the bone-side loop that is formed in step A.

40. A method as claimed in claim 28, comprising drawing one of the bone-side loops into contact with the bone-facing surface of the fixation device by shortening the loop, said bone-side loop cooperating with the fixation loop and the knot assembly to secure the flexible elongate element to the fixation device.

41. A method as claimed in claim 40, in which the support loop comprises a first loop portion extending from one of the plurality of apertures to an apex of the loop, and a second loop portion extending from another one of the plurality of apertures to the apex of the loop, and in which the method comprises:

adjusting a length of the support loop by applying tension to the loop portion which extends from one side of the knot.

42. A method as claimed in claim 28, comprising directing the free ends of the flexible elongate element from the outer surface side of the fixation device and through the fixation device.

43. A method as claimed in claim 41, in which the method is a method of repairing damaged connective tissue.

44. A method as claimed in claim 28, in which one or more of the bone-side loops that are formed extends from one of the plurality of apertures at the bone facing surface of the fixation device to another one of the plurality of apertures at the bone facing surface.

45. A method as claimed in claim 28, in which one or more of the bone-side loops that are formed extends from a same one of the plurality of aperture at the bone facing surface of the fixation device.

46. A method of carrying out tissue repair involving the fixation of an implant within a tunnel in a bone, the method comprising use of the implant assembly of claim 1 to locate an implant in a tunnel in a bone.

\* \* \* \* \*